(12) United States Patent
Kerfeld et al.

(10) Patent No.: US 10,480,003 B2
(45) Date of Patent: Nov. 19, 2019

(54) CONSTRUCTS AND SYSTEMS AND METHODS FOR ENGINEERING A $CO_2$ FIXING PHOTORESPIRATORY BY-PASS PATHWAY

(71) Applicant: The Regents of the University of California, Oakland, CA (US)

(72) Inventors: Cheryl A. Kerfeld, Walnut Creek, CA (US); Patrick Shih, Berkeley, CA (US); Jan Zarzycki, Marburg (DE); Krishna K. Niyogi, Oakland, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 2 days.

(21) Appl. No.: 15/230,332

(22) Filed: Aug. 5, 2016

(65) Prior Publication Data
US 2017/0088850 A1   Mar. 30, 2017

Related U.S. Application Data

(63) Continuation of application No. PCT/US2015/014929, filed on Feb. 6, 2015.

(60) Provisional application No. 61/936,788, filed on Feb. 6, 2014.

(51) Int. Cl.
*C12N 15/82* (2006.01)

(52) U.S. Cl.
CPC ..... *C12N 15/8269* (2013.01); *C12N 15/8243* (2013.01); *Y02P 60/247* (2015.11)

(58) Field of Classification Search
CPC .................................................. C12N 15/8269
See application file for complete search history.

(56) References Cited

U.S. PATENT DOCUMENTS

| 8,349,587 B2 | 1/2013 | Fischer et al. |
| 2012/0210459 A1 | 8/2012 | Kerfeld et al. |

FOREIGN PATENT DOCUMENTS

| WO | WO 2010/012796 A1 | 2/2010 | |
| WO | WO 2011/095528 A1 | 8/2011 | |
| WO | WO 2013/130934 | * 2/2013 | ............... C12N 1/00 |
| WO | WO 2013/130394 A1 | 9/2013 | |
| WO | WO-2013130394 A1 * | 9/2013 | ......... C12N 15/8261 |

OTHER PUBLICATIONS

Shih, P. et al. The Journal of Biological Chemistry; 2014, vol. 298, No. 14, pp. 9493-9500.*
Zarzycki, J. et al., Sep. 2011; Applied and Environmental Microbiology, vol. 77, No. 7, pp. 6181-6188+suupl; 14 pages.*
Zarzycki, J. el al., Sep. 2011; Applied and Environmental Microbiology, vol. 77, No. 7, pp. 6181-6188.*
Batzer, et al. Enhanced evolutionary PCR using oligonucleotides with inosine at the 3'-terminus. Nucleic Acid Res. 19:5081 (1991).
Ohtsuka, et al. An Alternative Approach to Deoxyoligonucleotides as Hybridization Probes by Insertion of Deoxyinosine at Ambiguous Codon Positions. J. Biol. Chem., 260:2605-2608 (1985).
Rossolini, et al.Use of deoxyinosine-containing primers vs degenerate primers for polymerase chain reaction based on ambiguous sequence information. Mol. Cell. Probes, 8:91-98 (1994).
Su, et al. (2004) Biotechnol Bioeng 85:610-9.
Fetter, et al. Interactions between Plasma Membrane Aquaporins Modulate Their Water Channel Activity. (2004) Plant Cell 16:215-28).
Bolte, et al. The N-myristoylated Rab-GTPase m-Rabmc is involved in post-Golgi trafficking events to the lytic vacuole in plant cells. (2004) J. Cell Science 117:943-54.
Kato, et al. Spectral Profiling for the Simultaneous Observation of Four Distinct Fluorescent Proteins and Detection of Protein-Protein Interaction via Fluorescence Resonance Energy Transfer in tobacco Leaf Nuclei[1] (2002) Plant Physiol 129:931-42.
Savir, et al. (2010) Cross-species analysis traces adaptation of Rubisco toward optimality in a low-dimensional landscape. Proc. Natl. Acad. Sci. U. S. A. 107, 3475-3480.
Tcherkez, et al. (2006) Despite slow catalysis and confused substrate specificity, all ribulose bisphosphate carboxylases may be nearly perfectly optimized. Proc. Natl. Acad. Sci. U. S. A. 103, 7246-7251.
Kebeish, et al. (2007) Chloroplastic photorespiratory bypass increases photosynthesis and biomass production in *Arabidopsis thaliana*. Nat. Biotechnol. 25, 593-599.
Pellicer, et al. (1996) glc locus of *Escherichia coli*: characterization of genes encoding the subunits of glycolate oxidase and the glc regulator protein. J. Bacteriol. 178, 2051-2059.
Maier, et al. (2012) Transgenic introduction of a glycolate oxidation cycle into *A. thaliana* chloroplasts improves biomass production. Front Plant Sci 3, 38.
Nogales, et al. (2012) Detailing the optimality of photosynthesis in cyanobacteria through systems biology analysis. Proc Natl Acad Sci 109, 2678-2683.
Blankenship, et al. (2011) Comparing photosynthetic and photovoltaic efficiencies and recognizing the potential for improvement. Science 332, 805-809.

(Continued)

*Primary Examiner* — Russell Kallis
(74) *Attorney, Agent, or Firm* — Knobbe, Martens, Olson & Bear, LLP

(57) ABSTRACT

Methods and compositions to introduce a synthetic pathway based on the 3-hydroxypropionate bicycle into an organism such as the model cyanobacterium, *Synechococcus elongatus* sp. PCC 7942. The heterologously expressed pathway acts as a photorespiratory bypass as well as an additional carbon fixation cycle orthogonal to the endogenous Calvin-Benson cycle. We demonstrate the function of all six introduced enzymes, which not only has implications on increasing net-photosynthetic productivity, but also key enzymes in the pathway are involved in high-value products that are of biotechnological interest, such as 3-hydroxypropionate.

Figure 1A:
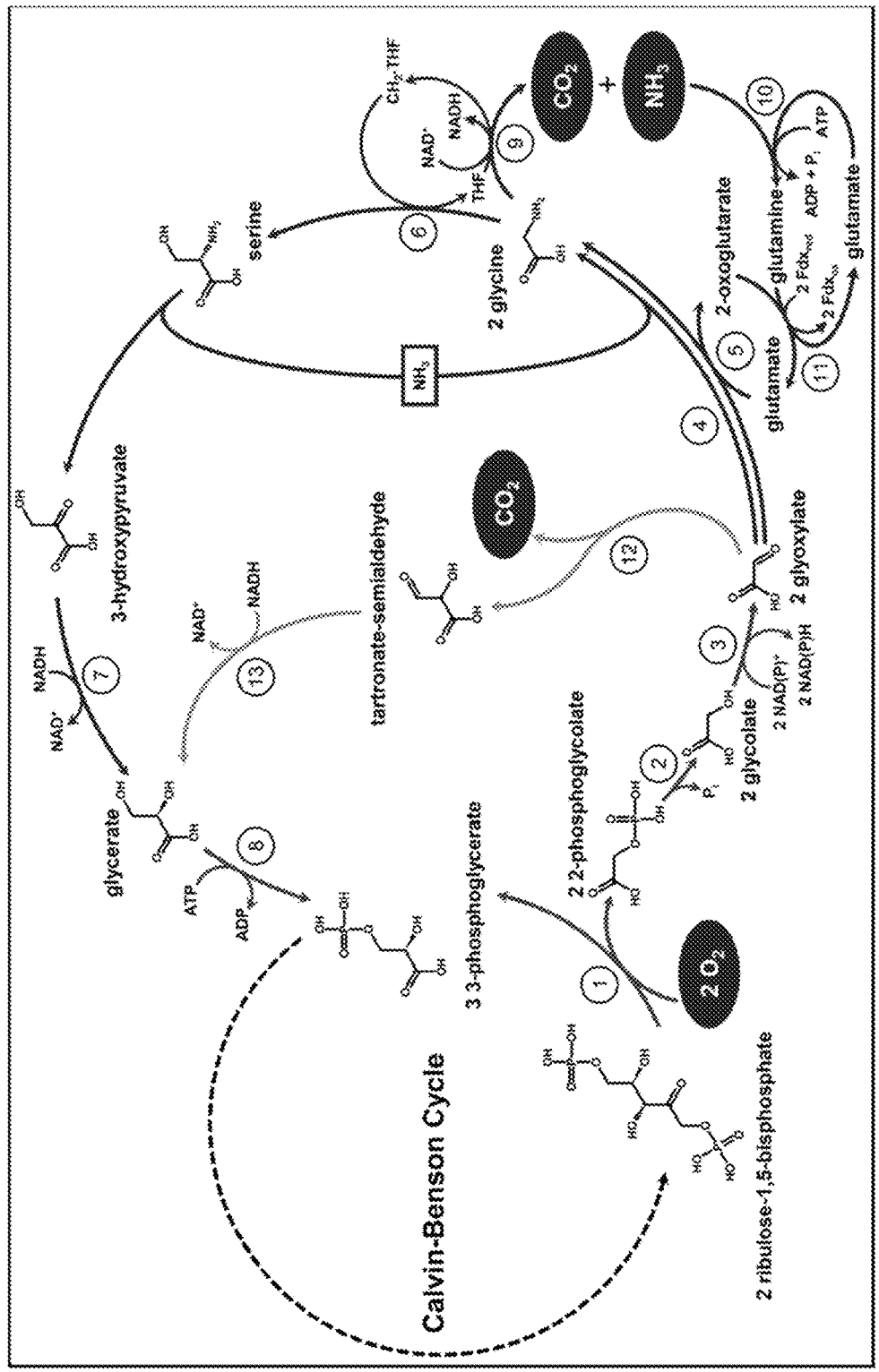

20 Claims, 6 Drawing Sheets
Specification includes a Sequence Listing.

(56) References Cited

OTHER PUBLICATIONS

Fuchs, G. (2011) Alternative pathways of carbon dioxide fixation: Insights into the early evolution of life? Annu. Rev. Microbiol. 65, 631-658.

Zarzycki, et al. (2009) Identifying the missing steps of the autotrophic 3-hydroxypropionate $CO_2$ fixation cycle in Chloroflexus aurantiacus. Proc Natl Acad Sci 106, 21317-21322.

Mattozzi, et al. (2013) Expression of the sub-pathways of the Chloroflexus aurantiacus 3-hydroxypropionate carbon fixation bicycle in E. coli: Toward horizontal transfer of autotrophic growth. Metab Eng 16, 130-139.

Anderson, et al. (2010) BglBricks: A flexible standard for biological part assembly. J Biol Eng 4, 1.

Mackey, et al. (2007) Detection of rhythmic bioluminescence from luciferase reporters in cyanobacteria. in Circadian Rhythms (Rosato, E. ed.), Methods in Molecular Biology, vol. 362, pp. 115-129.

Niederholtmeyer, et al. (2010) Engineering cyanobacteria to synthesize and export hydrophilic products. Appl. Environ. Microbiol. 76, 6023-6023.

Zarzycki, et al. (2013) The crystal structures of the tri-functional Chloroflexus aurantiacus and bi-functional Rhodobacter sphaeroides malyl-CoA lyases and comparison with CitE-like superfamily enzymes and malate synthases. BMC Struct, Biol. 13, 28.

Hügler, et al. (2002) Malonyl-coenzyme A reductase from Chloroflexus aurantiacus, a key enzyme of the 3-hydroxypropionate cycle for autotrophic $CO_2$ fixation. J. Bacteriol. 184, 2404-2410.

Alber, et al. (2002) Propionyl-Coenzyme A Synthase from Chloroflexus aurantiacus, a key enzyme of the 3-hydroxypropionate cycle for autotrophic $CO_2$ fixation. J. Biol. Chem. 277, 12137-12143.

Ducat, et al. (2011) Rewiring hydrogenase-dependent redox circuits in cyanobacteria. Proc Natl Acad Sci 108, 3941-3946.

Clerico, et al. (2007) Specialized techniques for site-directed mutagenesis in cyanobacteria. in Circadian Rhythms (Rosato, E. ed.), Methods in Molecular Biology, vol. 362, pp. 155-171.

Lipscomb, et al. (2012) Metabolic engineering of recombinant E. coli for the production of 3-hydroxypropionate. in Engineering Complex Phenotypes in Industrial Strains, John Wiley & Sons, Inc. pp. 185-200.

Horswill, et al. (2001) Studies of propionate toxicity in *Salmonella enterica* identify 2-methylcitrate as a potent inhibitor of cell growth. J. Biol. Chem. 276, 19094-19101.

Keasling, et al. (2010) Manufacturing molecules through metabolic engineering. Science 330, 1355-1358.

Garcia Martín, et al. (2006) Metagenomic analysis of two enhanced biological phosphorus removal (EBPR) sludge communities. Nat. Biotechnol. 24, 1263-1269.

Hesselmann, et al. (1999) Enrichment, phylogenetic analysis and detection of a bacterium that performs enhanced biological phosphate removal in activated sludge. Syst. Appl. Microbiol. 22, 454-465.

Zarzycki, et al. (2011) Coasslmilation of organic substrates via the autotrophic 3-hydroxypropionate bi-cycle in Chloroflexus aurantiacus. Appl. Environ. Microbiol. 77, 6181-6188.

Hu, et al. (2010) Anaerobic Digestion of Lignocellulosic Wastes by Rumen Microorganisms: Chemical and Kinetic Analyses. in Environmental Anaerobic Technology: Applications and New Developments (Fang, H. H.P. ed.), Imperial College Press, London. pp. 259-278.

Sharkey, T. D. (1988) Estimating the Rate of Photorespiration in Leaves. Physiol. Plant 73, 147-152.

Sasaki, et al. (1995) The Compartmentation of Acetyl-Coenzyme A Carboxylase in Plants. Plant Physiol 108, 445-449.

Eisenhut, et al. (2008) The photorespiratory glycolate metabolism is essential for cyanobacteria and might have been conveyed endosymbiontically to plants. Proc Natl Acad Sci 105, 17199-17204.

Zarzycki, et al. (2012) Cyanobacterial-based approaches to improving photosynthesis in plants. J. Exp. Bot. 64, 787-798.

Eisenhut, et al. (2006) The plant-like C2 glycolate cycle and the bacterial-like glycerate pathway cooperate in phosphoglycolate metabolism in cyanobacteria. Plant Physiol 142, 333-342.

Wang, et al. Biosynthetic Pathway for Poly(3-Hydroxypropionate) in Recombinant *Escherichia coli*. J. Microbiol. 2012, vol. 50, No. 4, pp. 693-697.

International Search Report & Written Opinion dated Aug. 25, 2015 in PCT/US2015/014929.

International Preliminary Report on Patentability dated Aug. 9, 2016 in PCT/US2015/014929.

\* cited by examiner

FIG.2F

| Transformant strain | Spec. activities of introduced enzymes at 37 °C [nmol × min$^{-1}$ × mg$_{(protein)}$$^{-1}$] | | |
|---|---|---|---|
| | MCR | PCS | MCL (whole route)* |
| PCS/PMS4570 | 1320 | 25 | 870 (<1)§ |
| PCS/PMS4591 | 330 | 25 | 480 (>450) |
| PCS/PMS4749 | 450 | 24 | 470 (>450) |

US 10,480,003 B2

CONSTRUCTS AND SYSTEMS AND METHODS FOR ENGINEERING A CO$_2$ FIXING PHOTORESPIRATORY BY-PASS PATHWAY

CROSS-REFERENCE TO RELATED APPLICATIONS

This application is continuation and non-provisional application of and claims priority to International Patent Application No. PCT/US2015/014929, filed on Feb. 6, 2015, which claims priority to U.S. Provisional Patent Application No. 61/936,788, filed on Feb. 6, 2014, both of which are hereby incorporated by reference in their entirety.

STATEMENT OF GOVERNMENTAL SUPPORT

This invention was made with government support under Contract No. DE-AC02-05CH11231 awarded by the U.S. Department of Energy, under Grant No. MCB0851054 awarded by the National Science Foundation. The government has certain rights in the invention.

REFERENCE TO SEQUENCE LISTING AND TABLES

This application also incorporates by reference the attached Tables 1-4 found in paper form.

A sequence listing is submitted concurrently with the specification and is part of the specification and is hereby incorporated in its entirety by reference herein. This application also incorporates by reference the sequence listing found in computer-readable form in a *.txt file entitled, "2013-020-03_SeqListing_ST25.txt", created on Aug. 5, 2016.

BACKGROUND OF THE INVENTION

Field of the Invention

The present invention relates to synthetic biology, especially using operons and synthetic constructs to produce a non-natural or engineered cyclic by-pass of the photorespiration pathway in organisms such as plants, cyanobacteria and microbes.

Related Art

Oxygenic photosynthesis is the primary source of nearly all biological energy. In this process, light is converted into chemical energy which is used to fix $CO_2$ in the CB cycle through the enzyme RuBisCO. The carboxylase activity of RuBisCO results in the addition of one molecule of $CO_2$ to one molecule of ribulose-1,5-bisphosphate to create two molecules of 3-phosphoglycerate, thus fixing inorganic $CO_2$ into triose phosphates. However, the competing oxygenase activity of RuBisCO results in the loss of fixed carbon through a process termed photorespiration. One of the 'holy grails' of photosynthesis research has been to engineer RuBisCO to improve $CO_2$ fixation and reduce photorespiration; however, these attempts have been met with limited success. It has been shown that biochemical constraints as well as abiotic factors are crucial considerations in addressing the protein engineering of RuBisCO (1,2). Given this complexity, a more promising approach may be to accept the inherent 'flaws' of RuBisCO and improve net photosynthetic rates through engineered photorespiration bypasses.

The role of photorespiration is highly debated, as it consumes much more energy and cellular resources than its carboxylase counterpart reaction. The fixed $O_2$ from RuBisCO results in the toxic intermediate, 2-phosphoglycolate, which continues through the photorespiratory pathway (C2 cycle). This pathway is costly, because the 2-phosophoglycolate must be metabolized in order to detoxify the cell through an elaborate pathway involving more than a dozen enzymes (CHECK). Furthermore, the glycine decarboxylase conversion of glycine to serine, in the C2 cycle, releases both an ammonia and a $CO_2$ molecule, resulting in a net loss of carbon and nitrogen. Previous work has bypassed the C2 cycle by introducing the glycolate catabolic pathway from *Escherichia coli* into *Arabidopsis thaliana* chloroplasts resulting in improved growth rates (2). The pathway introduced by Kebeish et al circumvented the loss of nitrogen; however, the glyoxylate carboligase decarboxylates glyoxylate, losing one $CO_2$ molecule and thus still resulting in a net loss in carbon. Although the irrelevance of photorespiration can be inferred from this work, genome-scale metabolic modeling of cyanobacteria has suggested that photorespiration is essential for optimal photosynthesis (3).

Photorespiration produces the toxic intermediate 2-phosphoglycolate, which is recycled through the photorespiratory $C_2$ cycle (FIG. 1A). This pathway is costly, requiring ATP and reducing equivalents in an elaborate reaction sequence involving more than a dozen enzymes and transporters. Furthermore, the reaction catalyzed by glycine decarboxylase, converting two glycine molecules into one serine in the $C_2$ cycle, releases both $NH_3$ and $CO_2$, resulting in a net loss of carbon and nitrogen. To date, only two studies have attempted to experimentally decrease the negative impacts of the photorespiratory $C_2$ cycle by expression of alternative glycolate metabolic pathways. Kebeish et al. (3) attempted to bypass most of the $C_2$ cycle by introducing the glycolate catabolic pathway from *E. coli* (4) into *Arabidopsis thaliana* chloroplasts. This pathway circumvents the loss of nitrogen, but the glyoxylate carboligase reaction results in the release of one $CO_2$ per two glyoxylate molecules (FIG. 1A). Although increased biomass was reported, interestingly, transformants expressing only the first enzyme of that pathway, glycolate dehydrogenase, showed similar results, rendering the approach controversial. In a second study, Maier et al. (5) introduced a glycolate oxidation cycle into *Arabidopsis* chloroplasts; however this pathway results in the release of even more $CO_2$ than the heterologously expressed glycolate catabolism pathway. In both cases, $CO_2$ release occurs in the chloroplast, where it can potentially be refixed by RuBisCO. The challenges associated with designing experimental approaches to mitigate the losses associated with photorespiration are likewise underscored by results from systems-level genome-scale metabolic modeling that suggests photorespiration is essential for optimal photosynthesis (6)

Introduction of additional, synthetic $CO_2$ fixation pathways provide an approach to increasing photosynthesis, which circumvents the complexities associated with manipulating the $C_2$ cycle (7). Of the six known $CO_2$ fixation cycles in nature, only the 3-hydroxypropionate (3OHP) bi-cycle is completely oxygen insensitive (8,9), a key consideration when engineering pathways into oxygenic photoautotrophs. The 3OHP bi-cycle from the thermophilic anoxygenic phototroph *Chloroflexus aurantiacus* offers an attractive starting point for engineering efforts (10), because all of the necessary enzymes have been characterized (9). In this bi-cyclic pathway, bicarbonate is fixed by biotin-dependent acetyl-CoA carboxylase and propionyl-CoA carboxylase. The primary $CO_2$ fixation product resulting from the first cycle is glyoxylate, which is then fed into the second cycle, in which another bicarbonate is fixed and pyruvate is generated as the final product (9).

Independent of photorespiration, various synthetic carbon fixation pathways have been proposed as a potential way to increase net photosynthetic yield (4). Of the six known carbon fixation cycles that exist in nature, only the Calvin-Benson cycle and the 3-hydroxypropionate bicycle lack enzymes that are oxygen sensitive (5), a key factor to consider when engineering pathways into oxygenic photoautotrophs. Further studies have expanded upon natural carbon fixation pathways to predict novel carbon fixation pathways by mining enzyme databases and building cycles in silico (6).

Carbon and carbon dioxide ($CO_2$) fixation in cyanobacteria proceeds via the reductive pentosephospate cycle (Calvin-Benson cycle). The key carboxylase of that $CO_2$ fixation cycle is ribulose-1,5-bisphosphate carboxylase/oxygenase (RuBisCO). The oxygenase side reaction of RuBisCO results in the formation of a toxic compound (2-phosphoglycolate), which has to be removed or ideally recycled. In cyanobacteria and plants this is achieved in a series of reactions (photorespiration) involving the loss of $CO_2$ and $NH_3$, which both have to be re-assimilated at the cost of additional energy.

Cyanobacteria convert $CO_2$ into biomass using solar energy. The rate limiting step in this process is the fixation of $CO_2$ by enzyme RuBisCO. RuBisCO is a very inefficient catalyst, because it has relatively low affinity to its substrates and is not able to discriminate between $CO_2$ and $O_2$. The use of $O_2$ instead of $CO_2$ leads to photorespiration. Phosphoglycolate produced from the oxygenase side reaction of RuBisCO is toxic to cells, because it completely inhibits triosephosphate isomerase at micro molar levels. Therefore, 2-phosphoglycolate is recycled to 3-phosphoglycerate via a series of reactions (FIG. 1). This leads to the release of $CO_2$ and $NH_3$, which both have to be re-fixed consuming extra energy.

Others have described different methods of increasing photosynthetic carbon fixation. For example, Kebeish, Rashad et al. describe a method for increasing photosynthetic carbon fixation in rice in WO2010012796 A1, hereby incorporated by reference. Kreuzaler, Fritz et al. describe a method for increasing photosynthetic carbon fixation using glycolate dehydrogenase multi-subunit fusion protein in WO2011095528 A1, also hereby incorporated by reference. However, there is a need for other compositions and methods that provide more energetically and metabolically desirable approaches.

BRIEF SUMMARY OF THE INVENTION

The present invention provides for constructs and systems and methods for producing and expressing in an organism a synthetic carbon fixation cycle that also acts as a photorespiratory bypass based on half of the 3-hydroxypropionate bicycle characterized from *Chloroflexus aurantiacus* (*Chloroflexus*) (7). Bicarbonate is fixed through Acetyl CoA Carboxylase, and glyoxylate is inputted as a photorespiratory byproduct, resulting in a net gain in carbon through the generation of pyruvate.

In order to examine the potential and consequences of introducing carbon fixation pathways into oxygenic photoautotrophs, a synthetic pathway based on the 3-hydroxypropionate bicycle was introduced into the model cyanobacterium, *Synechococcus elongatus* sp. PCC 7942. The heterologously expressed pathway acts as a photorespiratory bypass as well as an additional carbon fixation cycle orthogonal to the endogenous Calvin-Benson cycle. The examples herein demonstrate the function of all six introduced enzymes, which not only has implications on increasing net-photosynthetic productivity, but also key enzymes in the pathway are involved in high-value products that are of biotechnological interest, such as 3-hydroxypropionate.

In one embodiment, the present invention provides for a construct or an expression cassette comprising a heterologous polynucleotide encoding a cluster of enzymes, wherein the cluster comprising a set of genes necessary for the expression of a synthetic photorespiratory bypass pathway in a host cell.

The expression cassette can be used to provide a cell comprising in its genome at least one stably incorporated expression cassette, where the expression cassette comprising a heterologous nucleotide sequence or a fragment thereof operably linked to a promoter that drives expression in the cell and operably linked to a ribosomal binding site that controls expressions efficiency in the cell.

The present invention further describes methods for production of a photorespiratory bypass in plant, cyanobacterial, algae, and other host organisms.

Figure 1B:
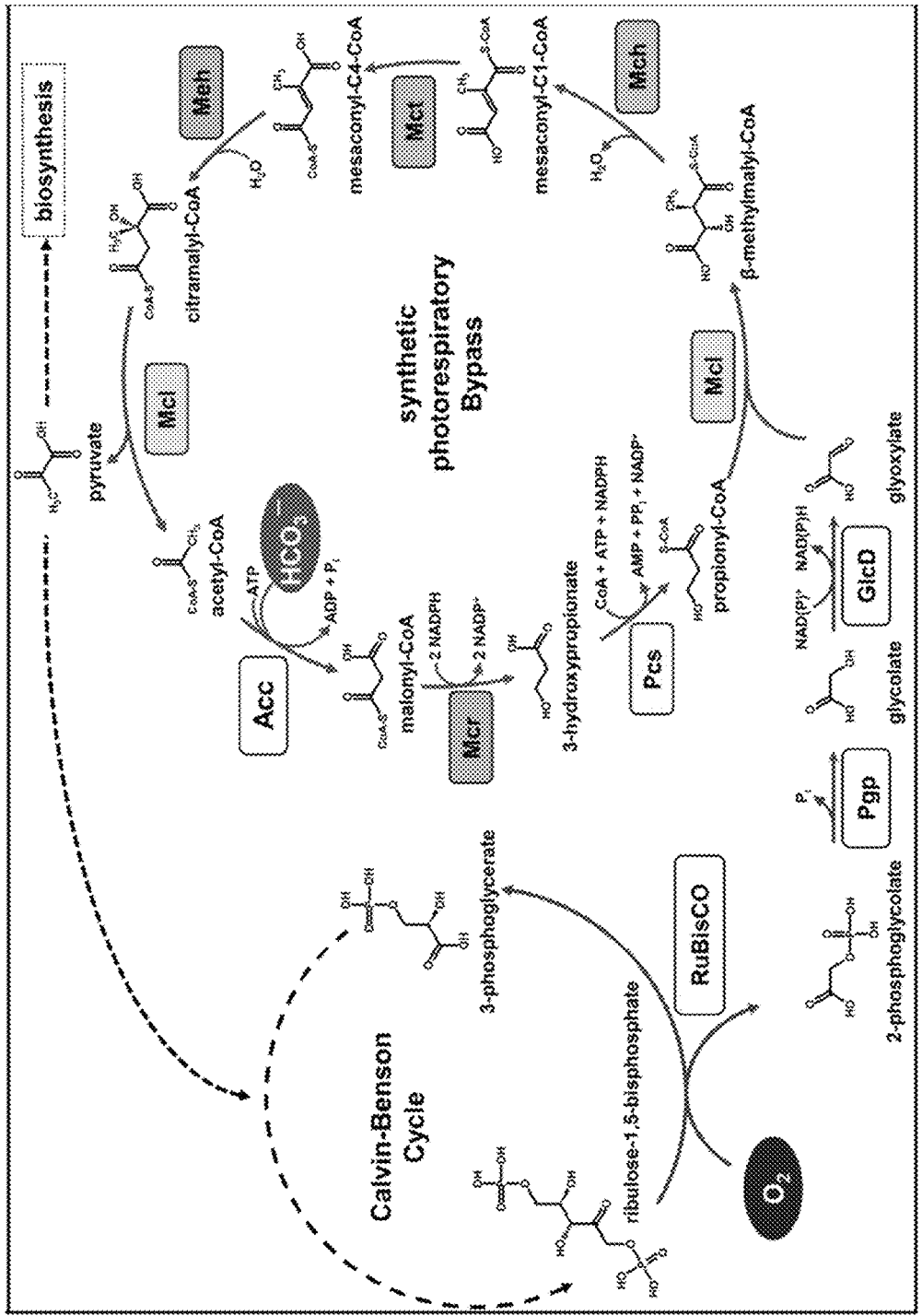

In one embodiment, a $CO_2$-fixing synthetic photorespiratory bypass based on the 3OHP bi-cycle (FIG. 1B). To experimentally validate the design, a set of six genes encoding the mcr, mcl, mch, mct, meh and pcs enzymes, were encoded in assembled DNA constructs spanning more than 16 kbp, to reassimilate the photorespiratory byproduct glyoxylate in the cyanobacterium *S. elongatus* PCC7942. Activity for all of the gene products was demonstrated and identification made of metabolic bottlenecks to be addressed. In comparison to the conventional $C_2$ cycle, the synthetic bypass described herein not only prevents the loss of $NH_3$ but also results in a net gain in carbon fixation rather than a net loss, thus demonstrating a metabolically and energetically favorable result.

Herein described are methods for enhancing metabolic activity in an organism. In one embodiment, a method comprising introducing into an organism at least one expression cassette operably linked to a promoter that drives expression in the organism, where the expression cassette comprising a cluster of photorespiratory bypass enzymes derived from a bacteria, wherein the cluster comprising a set of photorespiratory bypass genes necessary for the expression of a synthetic photorespiratory bypass pathway to provide the non-native organism enhanced metabolic activity.

In other embodiments, methods for increasing improving the efficiency of photosynthesis by introduction of an expression cassette comprising a cluster of photorespiratory bypass genes in a photosynthetic organism.

In another embodiment, methods for increasing photosynthetic carbon fixation in a photosynthetic organism or plant.

BRIEF DESCRIPTION OF THE SEQUENCES

SEQ ID NOS:1-18 are nucleotide sequences used for cloning.

SEQ ID NO:19 is the enzyme sequence for propionyl-CoA synthase (PCS), *Chloroflexus aurantiacus* J-10-fl, having GenBank Accession No. AAL47820.2.

SEQ ID NO:20 is the enzyme sequence for (MCR) malonyl-CoA reductase in *Chloroflexus aurantiacus* J-10-fl, having GenBank Accession No. AAS20429.1.

SEQ ID NO:21 is the enzyme sequence for HpcH/HpaI aldolase (MCL) in *Chloroflexus aurantiacus* J-10-fl, having GenBank Accession No. ABY33428.1

SEQ ID NO:22 is the enzyme sequence for MaoC domain protein dehydratase (MCH) in *Chloroflexus aurantiacus* J-10-fl, having GenBank Accession No. ABY33427.1.

SEQ ID NO:23 the enzyme sequence for L-carnitine dehydratase/bile acid-inducible protein F (MCT) in *Chloroflexus aurantiacus* J-10-fl, having GenBank Accession No. ABY33429.1.

SEQ ID NO:24 is the enzyme sequence for MEH in *Chloroflexus aurantiacus* J-10-fl, having GenBank Accession No. ABY33434.1.

SEQ ID NO:25 is the enzyme sequence for MCR homolog, NAD-dependent epimerase/dehydratase:Short-chain dehydrogenase/reductase SDR in *Erythrobacter* sp. *NAP*1, having GenBank Accession No. EAQ29650.1.

SEQ ID NO:26 is the enzyme sequence for PCS homolog, acetyl-coenzyme A synthetase in *Erythrobacter* sp. *NAP*1, having GenBank Accession No. EAQ29651.1.

SEQ ID NO:27 is the enzyme sequence for MCL homolog HpcH/HpaI aldolase in *Candidatus Accumulibacter phosphatis clade IIA str. UW*-1, having GenBank Accession No. ACV35795.1.

SEQ ID NO:28 is the enzyme sequence for MCH homolog, MaoC domain protein dehydratase (MCH) in *Candidatus Accumulibacter phosphatis clade IIA str. UW*-1, having GenBank Accession No. ACV35796.1.

SEQ ID NO:29 is the enzyme sequence for MCT homolog, acyl-CoA transferase/carnitine dehydratase-like protein in *Candidatus Accumulibacter phosphatis clade IIA str. UW*-1, having GenBank Accession No. ACV35794.1.

SEQ ID NO:30 is the enzyme sequence for MEH homolog in *Candidatus Accumulibacter phosphatis clade IIA str. UW*-1, having GenBank Accession No. ACV35791.1.

SEQ ID NO:31 is the DNA sequence of the PMS4570 construct.

SEQ ID NO:32 is the DNA sequence of the PMS4591 construct.

SEQ ID NO:33 is the DNA sequence of the PMS4749 construct.

SEQ ID NO:34 is the DNA sequence of the PCS construct.

SEQ ID NO:35 is the DNA sequence of the pAM1573PMS construct.

SEQ ID NO:36 is the DNA sequence of the pNS3 construct.

BRIEF DESCRIPTION OF THE DRAWINGS AND TABLES

FIG. 1. A) Schematic of the conventional photorespiratory $C_2$ cycle (black) in cyanobacteria and the glycerate bypass (gray), adapted from Zarzycki et al. (29). Reactions that take part in both pathways are colored purple. Ribulose-1,5-bisphosphate carboxylase/oxygenase (1), phosphoglycolate phosphatase (2), glycolate dehydrogenase (3), serine/glyoxylate aminotransferase (4), glutamate/glyoxylate aminotransferase (5), serine hydroxymethyl-transferase (6), glycine decarboxylase (7), hydroxypyruvate reductase (8), glycerate kinase (9), glutamine synthetase (10), glutamine oxoglutarate aminotransferase (11), glyoxylate carboligase (12), tartronate-semialdehyde reductase (13). tetrahydrofolate (THF), methylenetetrahydrofolate ($CH_2$-THF), reduced ferredoxin ($Fdx_{red}$), oxidized ferredoxin ($Fdx_{ox}$). FIG. 1B) Engineering a synthetic cyclic photorespiratory bypass based on part of the 3OHP bi-cycle, which also fixes bicarbonate. Overview of the design and its intersection with the CB cycle. Enzymes in white boxes are present in cyanobacteria and plants. The six additional enzymes required to establish this $CO_2$ fixing photorespiratory bypass are in colored boxes. One bicarbonate molecule is fixed while one glyoxylate is consumed to form pyruvate, which can be used for biosynthesis or to replenish the CB cycle. Acc—acetyl-CoA carboxylase, Mcr—malonyl-CoA reductuse; Pcs—propionyl-CoA synthase, Mcl—malyl-CoA lyase, Mch—mesaconyl-C1-CoA hydratase, Mct—mesaconyl-CoA C1:C4 CoA transferase, Meh—mesaconyl-C4-CoA hydratase, Pgp—2-phosphoglycolate phosphatase, GlcD—glycolate dehydrogenase, RuBisCO—ribulose-1,5-bisphosphate carboxylase/oxygenase.

Figure 2A:
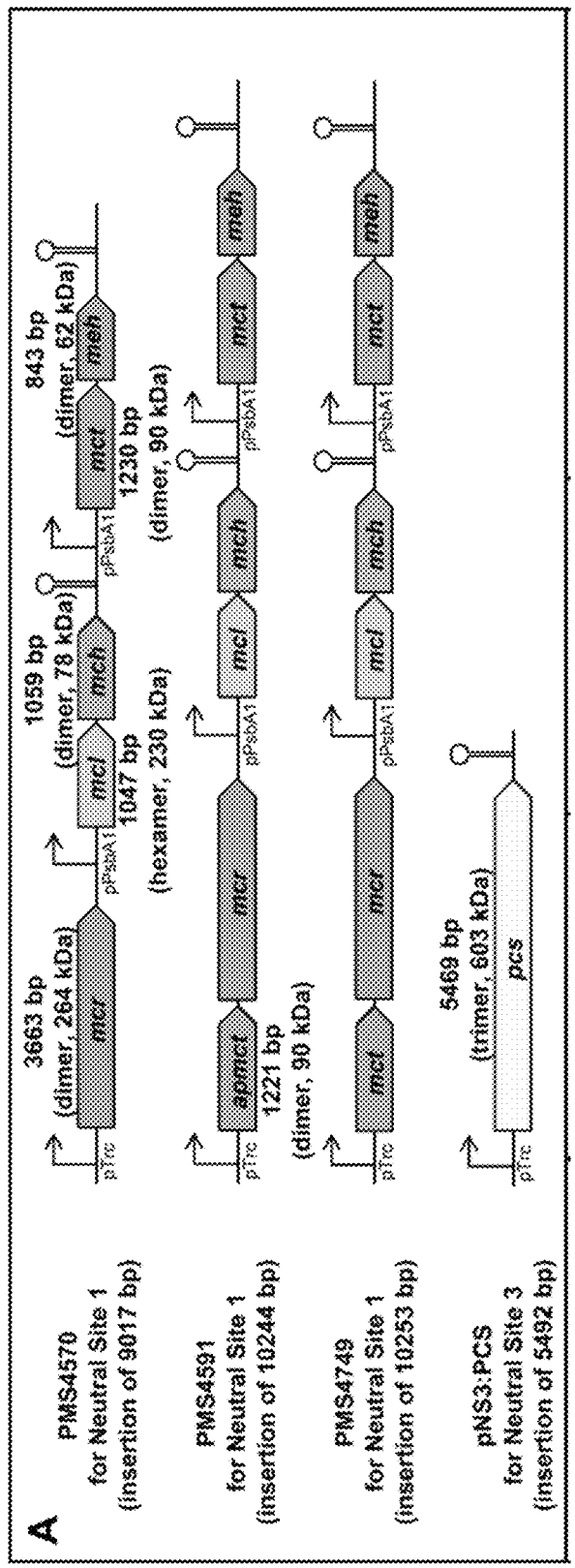
Figure 2B:
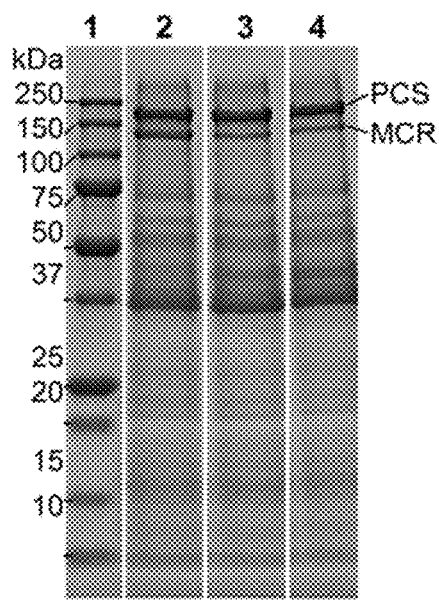
Figure 2C:
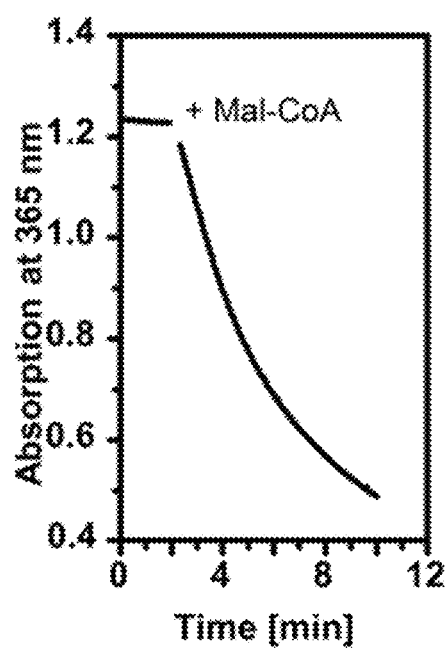
Figure 2D:
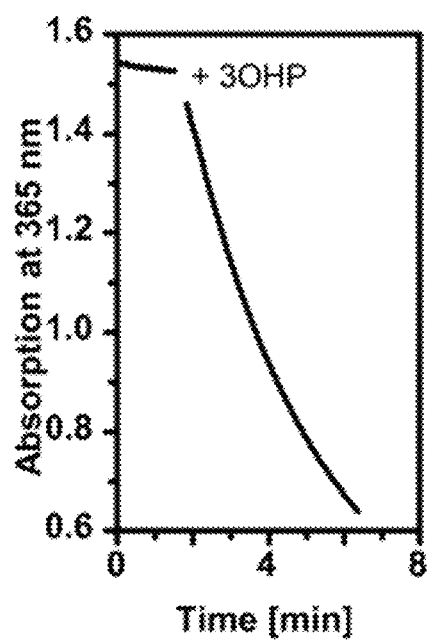
Figure 2E:
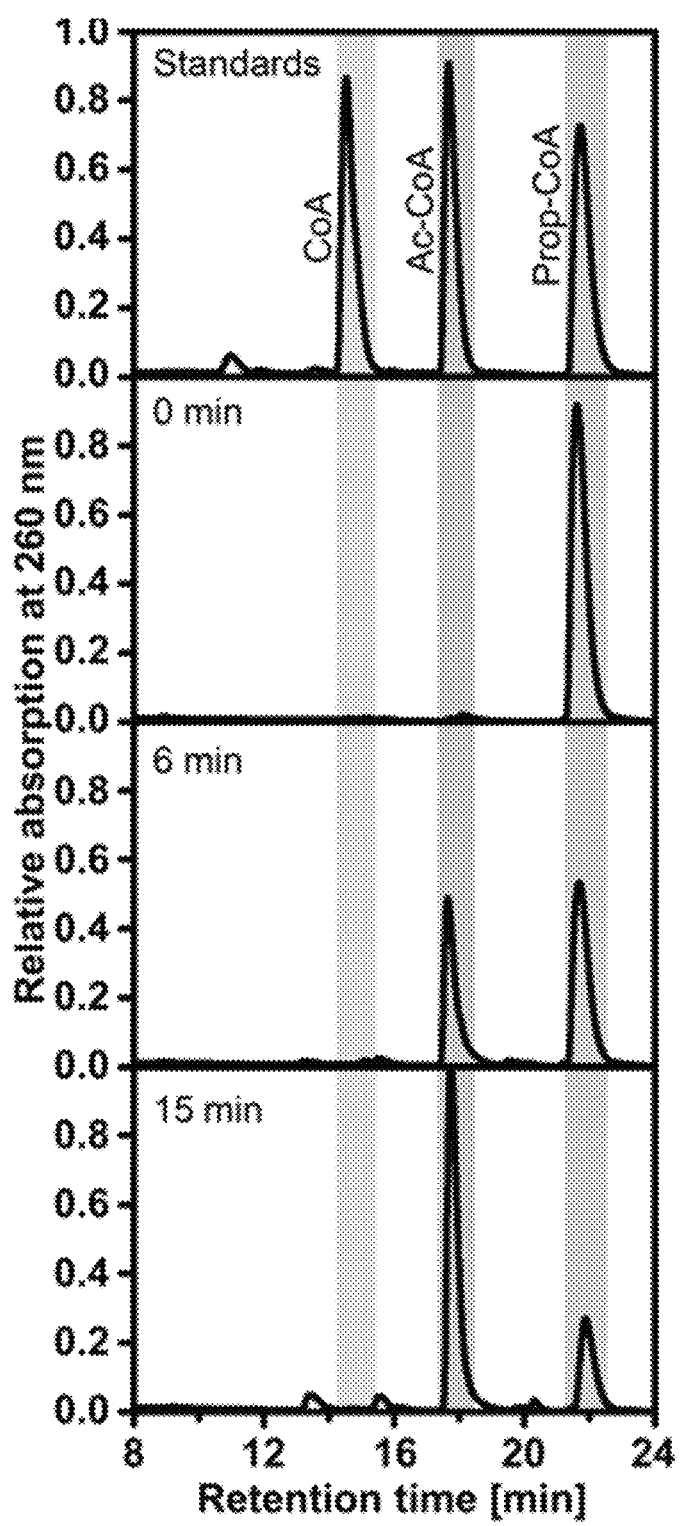

FIG. 2A) Schematic of assembled constructs and introduced genes integrated into the *S. elongatus* genome for generation of the PCS/PMS4570, PCS/PMS4591, and PCS/PMS4749 double transformants. Promoters and terminators are indicated by arrows and hairpins, respectively. Gene sizes and molecular weights of the functional enzymes are provided. Genes are colored as the corresponding enzymes in FIG. 1B. FIG. 2B) SDS-PAGE (coomassie stained) showing expression of the two large enzymes, MCR (malonyl-CoA reductase) and PCS (propionyl-CoA synthase). Lane 1—mass standards, lanes 2-4—cell extracts (25 µg protein each) of transformants PCS/PMS4570, PCS/PMS4591, PCS/PMS4749, respectively. FIG. 2C) Photometric assay for MCR activity monitoring the malonyl-CoA-dependent reduction of NADPH in transformant cell extract. FIG. 2D) Photometric assay for PCS activity monitoring the 3OHP-dependent reduction of NADPH in transformant cell extract. FIG. 2E) HPLC based assay demonstrating the disproportionation of glyoxylate and propionyl-CoA to pyruvate and acetyl-CoA by the coupled activity of MCL, MCH, MCT, and MEH in cell extracts of transformant PCS/PMS4749. FIG. 2F) Mean values (deviations <20%) were obtained from at least two independent measurements in cell extracts of replicate cultures. *Refers to the whole disproportionation of propionyl-CoA and glyoxylate to acetyl-CoA and pyruvate. Reaction sequence stalls at mesaconyl-C1-CoA due to very low MCT activity.

DETAILED DESCRIPTION OF THE PREFERRED EMBODIMENT

Introduction

Global photosynthetic productivity is limited by the enzymatic assimilation of $CO_2$ into organic carbon compounds. Ribulose-1,5-bisphosphate carboxylase/oxygenase (RuBisCO), the carboxylating enzyme of the Calvin-Benson (CB) cycle, poorly discriminates between $CO_2$ and $O_2$, leading to photorespiration and the loss of fixed carbon and nitrogen. With the advent of synthetic biology, it is now feasible to design, synthesize and introduce biochemical pathways in vivo. We engineered a synthetic photorespiratory bypass based on the 3-hydroxypropionate bi-cycle into the model cyanobacterium, *Synechococcus elongatus* sp. PCC 7942. The heterologously expressed cycle is designed to function as both a photorespiratory bypass and an additional $CO_2$-fixing pathway, supplementing the CB cycle. We demonstrate the function of all six introduced enzymes and identify bottlenecks to be targeted in subsequent bioengineering. These results have implications for efforts to improve photosynthesis, and for the "green" production of high-value products of biotechnological interest.

Herein is further described a synthetic pathway for $CO_2$ fixation using photorespiratory bypass based on the 3-hydroxypropionate bi-cycle in a heterologous host environment.

Definitions

An "expression vector" or "expression cassette" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

By "host cell" is meant a cell that contains an expression vector and supports the replication or expression of the expression vector. Host cells may be prokaryotic cells including but not limited to, cyanobacteria including but not limited to, *Synechococcus elongatus*, plants, or eukaryotic cells including but not limited to, algae, yeast, insect, amphibian, or mammalian cells such as CHO, HeLa and the like, e.g., cultured cells, explants, and cells in vivo.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Amino acid polymers may comprise entirely L-amino acids, entirely D-amino acids, or a mixture of L and D amino acids. The use of the term "peptide or peptidomimetic" in the current application merely emphasizes that peptides comprising naturally occurring amino acids as well as modified amino acids are contemplated.

Any "gene" is meant to refer to the polynucleotide sequence that encodes a protein, i.e., after transcription and translation of the gene a protein is expressed. As understood in the art, there are naturally occurring polymorphisms for many gene sequences. Genes that are naturally occurring allelic variations for the purposes of this invention are those genes encoded by the same genetic locus.

Any "bacterial microcompartment gene", "microcompartment gene" as referred to herein is meant to include any polynucleotide that encodes a Pfam00936 domain or Pfam03319 domain protein or variants thereof. When referring to the bacterial compartments or microcompartments, it is meant to include any number of proteins, shell proteins or enzymes (e.g., dehydrogenases, aldolases, lyases, etc.) that comprise or are encapsulated in the compartment.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. The term "purified" denotes that a nucleic acid or protein gives rise to essentially one band in an electrophoretic gel.

The terms "identical" or percent "identity," in the context of two or more polypeptide sequences (or two or more nucleic acids), refer to two or more sequences or subsequences that are the same or have a specified percentage of amino acid residues or nucleotides that are the same e.g., 60% identity, preferably 65%, 70%, 75%, 80%, 85%, 90%, 91%, 92%, 93%, 94%, 95%, 96%, 97%, 98%, 99% or 100% identity over a specified region (such as the first 100 amino acids of SEQ ID NOS:19-30), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are typically used.

The terms "nucleic acid" and "polynucleotide" are used interchangeably herein to refer to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, polypeptide-nucleic acids (PNAs). Unless otherwise indicated, a particular nucleic acid sequence also encompasses "conservatively modified variants" thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., *J. Biol. Chem.*, 260:2605-2608 (1985); Rossolini et al., *Mol. Cell. Probes*, 8:91-98 (1994)). The term nucleic acid can be used interchangeably with gene, cDNA, mRNA, oligonucleotide, and polynucleotide.

A "label" or "detectable label" is a composition detectable by spectroscopic, photochemical, biochemical, immunochemical, or chemical means. For example, useful labels include radioisotopes (e.g., $^3H$, $^{35}S$, $^{32}P$, $^{51}Cr$, or $^{125}I$), fluorescent dyes, electron-dense reagents, enzymes (e.g., alkaline phosphatase, horseradish peroxidase, or others commonly used in an ELISA), biotin, digoxigenin, or haptens and proteins for which antisera or monoclonal antibodies are available (e.g., proteins can be made detectable, e.g., by incorporating a radiolabel into the protein, and used to detect antibodies specifically reactive with the protein).

Detailed Description

In one embodiment, a synthetic metabolic pathway is selected to be synthesized and/or engineered in a host cell. A polynucleotide encoding the enzymes in the metabolic pathway can be inserted into a host organism and if needed, expressed using an inducible expression system.

In some embodiments, naturally existing or synthetic bacterial microcompartment operons which express microcompartment or shell proteins may be included. Prior strategies to produce microcompartment shells in heterologous hosts have transformed the host system with the natural operon sequences of the original organism. However, in a natural organism, the required shell proteins may not be placed together on the chromosome, they may be intermixed with enzymes or other proteins, and the ordering and regulatory mechanisms may not be useful in a new host organism.

In one embodiment, polynucleotides encoding enzymatic proteins in the photorespiratory by-pass pathway, are cloned into an appropriate plasmid, inserted into an expression vector, and used to transform cells from any host organism. Suitable host organisms include, but are not limited to, bacteria such as *E. coli, B. subtilis, S. cerevisiae*, cyanobacteria such as *S. elongatus*, plants such as *Nicotiana tabacum* and *Camelina sativa*, algae, fungi, or other eukaryotic organisms.

In one embodiment, the polynucleotides are in an inducible expression system which maintains the expression of the inserted genes silent unless an inducer molecule (e.g., IPTG) is added to the medium containing the host cell. The expression vector or construct may be a vector for coexpression or in some embodiments, it may be a neutral site vector for insertion in a host genome such as *Synechococcous elongatus*. The construct may include either inducible transcription elements or may be constitutively expressed in the host organism Bacterial colonies are allowed to grow after gene expression has begun, or if required, after induction of gene expression. Thus, in some embodiments, expression vectors comprising a promoter operably linked to a heterologous nucleotide sequence or a fragment thereof, that encodes a microcompartment RNA or proteins are further provided. The expression vectors of the invention find use in generating transformed plants, plant cells, microorganisms, algae, fungi, and other eukaryotic organisms as is known in the art and described herein. The expression vector will include 5' and 3' regulatory sequences operably linked to a polynucleotide of the invention. "Operably linked" is intended to mean a functional linkage between two or more elements. For example, an operable linkage between a polynucleotide of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The vector may additionally contain at least one additional gene to be co-transformed into the organism. Alternatively, the additional gene(s) can be provided on multiple expression vectors or cassettes. Such an expression vectors is provided with a plurality of restriction sites and/or recombination sites for insertion of the polynucleotide that encodes a microcompartment RNA or polypeptide to be under the transcriptional regulation of the regulatory regions. The expression vector may additionally contain selectable marker genes.

The expression vector will include in the 5'-3' direction of transcription, a transcriptional initiation region (i.e., a promoter), a cluster of bacterial compartment genes each preceded by a translational initiation site (RBS) specific to the organism and type of shell protein and followed by a translation termination signal (stop codon), and, optionally, a transcriptional termination region functional in the host organism. The regulatory regions (i.e., promoters, transcriptional regulatory regions, ribosomal binding sites and translational termination regions) and/or any targeting sequences may be native/analogous to the host cell or to each other. Alternatively, the regulatory regions and/or the targeting regions may be heterologous to the host cell or to each other. As used herein, "heterologous" in reference to a sequence that originates from a foreign species, or, if from the same species, is modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

In some embodiments, the selected photorespiratory pathway genes are placed onto the construct using the strategies described herein and shown in FIG. 2. In the first construct, the mcr gene is followed by the mcl, mch, mct and the meh genes. In a second construct, the pcs gene is provided. Therefore, in various embodiments, two expression vectors comprising a transcription start site sequence, the pathway constructs along with ribosomal binding site sequences that are specific for the host cell, are introduced to the non-native host cell. In some embodiments, the mcr, mcl, mch, mct, meh and pcs enzymes are SEQ ID NOS: 19-24 and/or their homologs SEQ ID NOS:25-30 and variants thereof.

In various embodiments, the synthetic operon contains the gene constructs as shown in FIG. 2 and described in SEQ ID NOS: 31-36.

TABLE 1

List of plasmids/strains generated.

| Construct | Host | Description | Insert Length | Reference |
|---|---|---|---|---|
| pAM1573 | S. elongatus | Neutral Site 2 genomic integration vector | | (12) |
| pAM1573PMS | S. elongatus | BglBrick modified pAM1573 vector | | this work |
| pNS3 | S. elongatus | Neutral site 3 genomic integration vector | | (13) |
| pNS3:PCS | S. elongatus | pTrc:PCS | 5492 bp | this work |
| PMS4032 | S. elongatus | pPsbA1::rbs.mcl::rbs.mch::pPsbA1::rbs.mct::rbs.meh | 5331 bp | this work |
| PMS4570 | S. elongatus | pTrc::rbs.mcr::pPsbA1::rbs.mcl::rbs.mch::pPsbA1::rbs.mct::rbs.meh | 9017 bp | this work |
| PMS4591 | S. elongatus | pTrc::rbs.ApMct::rbs.mcr::pPsbA1::rbs.mcl::rbs.mch::pPsbA1::rbs.mct::rbs.meh | 10244 bp | this work |

TABLE 1-continued

List of plasmids/strains generated.

| Construct | Host | Description | Insert Length | Reference |
|---|---|---|---|---|
| PMS4749 | S. elongatus | pTrc::rbs.mct::rbs.mcr::pPsbA1::rbs.mcl::rbs.mch::pPsbA1::rbs.mct::rbs.meh | 10253 bp | this work |
| pET16b | E. coli | IPTG inducible expression vector | | Novagen |
| pMct_Ap_JZ33 | E. coli | IPTG inducible Candidatus 'Accumulibacter phosphatis' mct | 855 bp | this work |

In other embodiments, the photorespiratory bypass pathway genes or constructs can be incorporated into multiple expression vectors and/or under multiple promoter control.

Where appropriate, the polynucleotides may be optimized for increased expression in the transformed organism. For example, the polynucleotides can be synthesized using preferred codons for improved expression.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression vector can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16-215-28), cyan florescent protein (CYP) (Bolte et al. (2004) *J. Cell Science* 117:943-54 and Kato et al. (2002) *Plant Physiol* 129:913-42), and yellow fluorescent protein (PhiYFP™ from Evrogen, see, Bolte et al. (2004) *J. Cell Science* 117:943-54). The above list of selectable marker genes is not meant to be limiting. Any selectable marker gene can be used in the present invention.

In another embodiment, it may be beneficial to express the gene from an inducible promoter, particularly from an inducible promoter. The gene product may also be co-expressed with a targeting polypeptide or fragment thereof, such that the polypeptide is in the C-terminal or N-terminal region of any other gene in the construct.

In various embodiments, the photorespiratory bypass is produced from another organism in a non-native bacterial host cell, such as *E. coli*, by construction of a synthetic operon as described herein. As described in the Examples, in one embodiment, the enzymes from *Chloroflexus aurantiacus J-10-fl* are used to create the photorespiratory bypass pathway is engineered to be produced in *S. elongatus*.

In one embodiment, an in-vitro transcription/translation system (e.g., Roche RTS 100 *E. coli* HY) can be used to produce cell-free expression products.

In some embodiments, the photorespiratory bypass may be expressed inside a microcompartment in the non-native host organism to provide the host organism enhanced enzymatic activity that is sequestered to encapsulate reactions that would otherwise be toxic to the cell but however, be non-toxic or have low toxicity levels to humans, animals and plants or other organisms that are not the target.

In some embodiments, the metabolic pathway is preferably incorporated into the genome of the host microorganism or eukaryote (e.g., plant, algae, yeast/fungi) to provide the new or enhanced metabolic activity described herein of enhanced carbon fixation.

Genes which encode the enzymes or proteins to carry out these enhanced reactions or activities and which will be encapsulated by the microcompartment may be targeted to the microcompartment by adding encapsulation tags specific for the microcompartment shell. Methods and compositions describing this in greater detail are described previously by some of the inventors in U.S. application Ser. No. 13/367,260 filed on Feb. 6, 2012, published as US-2002/02104590-A1 ("Design and Implementation of Novel and/or Enhanced Bacterial Microcompartments for Customizing Metabolism") and hereby incorporated by reference in its entirety. Such encapsulation tags and the genes encoding the proteins to be encapsulated may be incorporated in the expression vector itself or by co-expression of such encapsulation tagged genes which are on a second vector added to the host cell.

Example 1: Design and Construction of a Synthetic Operon for Expression Expression of a Synthetic Photorespiratory Bypass in *Synechococcus elongatus* sp. PCC 7942

We express a synthetic carbon fixation cycle that also acts as a photorespiratory bypass based on half of the 3-hydroxypropionate bicycle characterized from *Chloroflexus aurantiacus* (*Chloroflexus*) (7). Bicarbonate is fixed through Acetyl CoA Carboxylase, and glyoxylate is inputted as a photorespiratory byproduct, resulting in a net gain in carbon through the generation of pyruvate.

We designed a $CO_2$-fixing synthetic photorespiratory bypass based on the 3OHP bi-cycle (FIG. 1B). To experimentally validate the design, we introduced the requisite six genes, encoded in assembled DNA constructs spanning more than 16 kbp, to reassimilate the photorespiratory byproduct glyoxylate in the cyanobacterium *S. elongatus* PCC7942. We demonstrate activity for all of the gene products and identify metabolic bottlenecks to be addressed. In comparison to the conventional $C_2$ cycle, the synthetic bypass not only prevents the loss of $NH_3$ but also results in a net gain in carbon fixation rather than a net loss.

To implement the proposed cycle shown in FIG. 1B, we first tested the constitutive expression and activity of the first four *Chloroflexus* enzymes required, beginning where glyoxylate enters the cycle (i.e. enzymes [malyl-CoA lyase (MCL), mesaconyl-C1-CoA hydratase (MCD), mesaconyl-CoA C1-C4 transferase (MCT), and mesaconyl-C4-CoA hydratase (MEH)]). The reactions catalyzed by this sequence of enzymes result in the formation of acetyl-CoA and pyruvate (FIG. 1B) from propionyl-CoA and glyoxylate. Dicistronic operons were assembled to express mcl with mch and mct together with meh (FIG. 2A). Both dicistrons were driven by the previously characterized psbA1 promoter (17). The cassette expressing all four genes (referred to as PMS4032) was integrated into the *S. elongatus* genome at Neutral Site 1 (NS1) (18). The resulting transformants were assayed for activity of all four enzymes. Soluble cell extracts from the tranformants were incubated with propionyl-CoA and glyoxylate, and the expected disproportionation into acetyl-CoA and pyruvate was confirmed, indicating activity of all four enzymes; the rate of catalysis, however, was low The intermediates involved in the last two steps needed to complete the pathway in *S. elongatus*, MCR and PCS, are toxic to cells. Accumulation of 3OHP, the product of MCR, can lead to organic acid toxicity (19); propionyl-CoA, the product of PCS inhibits both pyruvate dehydrogenase and citrate synthase (20). The potential toxicity in conjunction with the difficulty of successfully reconstituting multi-step metabolic pathways (21) presented major challenges. Moreover, both MCR and PCS are large multi-domain enzymes, potentially presenting difficulty in proper folding and expression. For these reasons, mcr and pcs were driven by the IPTG-inducible promoter, pTrc (FIG. 2A). The mcr gene was assembled upstream of the PMS4032 cassette to generate PMS4570 and integrated into NS1 without an additional terminator downstream of mcr, whereas pcs alone was inserted into Neutral Site 3 (NS3) (13). Double transformants (PCS/PMS4570) containing all six genes integrated into both NS1 and NS3, were generated and tested for expression and enzyme activity in response to varying IPTG concentrations. MCR activity was confirmed spectrophotometrically by measuring the malonyl-CoA dependent oxidation of NADPH. PCS activity was measured by spectrophotometrically, by monitoring the 3OHP-dependent oxidation of NADPH and by following the formation of propionyl-CoA by HPLC. Both MCR and PCS were copiously expressed (FIG. 2B) and found to be active in the cell extracts (FIGS. 2C and 2D, respectively). An IPTG concentration of 20 µM yielded the highest enzyme activities; further increases in IPTG concentrations did not result in higher activities. Furthermore, the addition of the pTrc promoter upstream of mcr also increased the expression of the two downstream genes mcl and mch, as deduced from the results of enzyme activity assays. However, the conversion of propionyl-CoA and glyoxylate to acetyl-CoA and pyruvate was stalled at the mesaconyl-C1-CoA intermediate (see FIG. 1). Addition of purified recombinant MCT to the assay resulted in immediate conversion of mesaconyl-C1-CoA to acetyl-CoA and pyruvate, indicating that mct expression was the bottleneck, whereas the meh gene downstream of mct was adequately expressed (FIG. 2E).

To relieve the bottleneck, a second copy of mct, driven by the IPTG-inducible pTrc promoter, was added upstream of mcr. We tested two strategies for introducing the additional mct gene: 1) adding a duplicate *Chloroflexus* mct to generate PMS4749 and 2) introducing a synthetic mct homolog (referred to as ApMCT) from the β-proteobacterium '*Candidatus Accumulibacter* phosphatis' (22,23) resulting in PMS4591 (FIG. 2A). ApMCT is the most closely related mesophilic homolog to the *Chloroflexus* MCT (24). We confirmed its function by expressing in *E. coli* and purifying a recombinant $His_{10}$-tagged version of the ApMCT, which catalyzed the expected intramolecular CoA transfer reaction within mesaconyl-CoA with a specific activity of 37±6 µmol $min^{-1}$ $(mg\ protein)^{-1}$ at 37° C., corresponding to a turnover number ($k_{cat}$) of 58 $s^{-1}$ per dimer. Its apparent $K_m$ value for mesaconyl-C1-CoA was determined to be 1.49±0.22 mM, which was surprisingly high. In comparison the $K_m$ value of the *Chloroflexus* MCT is only 0.24 mM (9). Moreover, the specific activity of the *Chloroflexus* MCT is much higher, 520 µmol $min^{-1}$ $(mg\ protein)^{-1}$ at 55° C. (9), even assuming the reaction would be halved each 10° C. the temperature is decreased. Therefore, the overall efficiency of the ApMCT would be much lower.

Nevertheless, the double transformants encoding either a second mct gene from *Chloroflexus* or the Accumulibacter gene (PCS/PMS4749 or PCS/PMS4591, respectively) were generated (FIG. 2A) and assayed for all enzyme activities. In both cases the MCT activity was substantially increased, and the activity of all six enzymes engineered into *S. elongatus* was confirmed (FIGS. 2C, 2D, 2E, & 2F). However, introduction of the additional mct gene upstream of mcr apparently led to a decrease in MCR, MCL and MCH expression (FIG. 2B) and activity (FIG. 2F).

In order to estimate if the resulting enzyme activities were high enough to allow the functioning of the synthetic photorespiratory bypass, we calculated the carbon assimilation rate of a *S. elongatus* wild-type culture using the equation $dS/dt=(\mu/Y) \times X$ (25), which correlates the specific substrate consumption (dS) over time (dt) with the specific growth rate (µ). The established growth yield (Y) corresponds to a bacterial cell dry mass of 1 g formed per 0.5 g of carbon fixed (approx. 50% of bacterial cell dry mass is carbon). Although X usually refers to the concentration of living cells, in this case it is used to account for the amount of total protein per 1 g cell dry mass (in bacteria approx. 50% of cell dry mass is protein). We assumed a typical doubling time of 8 h for a wild-type culture under laboratory conditions with ambient $CO_2$, which corresponds to a p of 0.087 $h^{-1}$. This would require a net carbon assimilation rate of 121 nmol $min^{-1}$ $(mg\ protein)^{-1}$. Taking into account an estimated loss of up to 25% of the fixed carbon due to photorespiration (26) results in 80 nmol $min^{-1}$ $(mg\ protein)^{-1}$ for the oxygenase activity of RuBisCO and the production of glycolate. To efficiently reassimilate glycolate in the synthetic bypass the minimal specific activities of the involved enzymes need to be at least as high as the rate of glycolate generation. Based on that estimate all but one of the introduced enzymes were well above the required threshold (FIG. 2F). Only the specific activity of PCS (~25 nmol $min^{-1}$ $(mg\ protein)^{-1}$) in the transformant cell extracts was lower than the calculated threshold, despite very high expression (FIG. 2B).

This study is, to our knowledge, the first successful effort to express a synthetic $CO_2$-fixing photorespiratory bypass in a photoautotrophic organism, the cyanobacterium *S. elongatus* PCC7942. Unlike previous studies, our pathway differs by directly avoiding the net loss of nitrogen and carbon in the photorespiratory $C_2$ cycle, which actually results in a net gain in carbon fixation through the enzyme acetyl-CoA carboxylase (ACC).

The unique feature of our pathway is the additional carbon fixation, which must be accounted for in energy balance comparisons to other proposed photorespiratory bypasses. Therefore we have assumed the stoichiometrically correct values for the formation of two glycolate molecules per $CO_2$ released in the $C_2$ cycle (see Table 3). Thus, to reassimilate two glycolate molecules our cyclic bypass requires 6 ATP equivalents and 4 NAD(P)H, while fixing two additional molecules of bicarbonate, the form of inorganic carbon concentrated in the cytoplasm of cyanobacteria, and circumventing the loss of $NH_3$. Note that if pyruvate, which derives from our bypass, is to be used for replenishing the CB cycle two more ATP equivalents are required per pyruvate molecule in gluconeogenesis by pyruvate phosphate dikinase, because it is AMP-forming. Nevertheless, the synthetic bypass compares favorably over the canonical photorespiratory $C_2$ cycle of cyanobacteria in terms of energy demand: the combined function of the $C_2$ cycle and CB cycle requires 11 ATP equivalents, 4 NAD(P)H, and 2 reduced ferredoxins to first refix the lost $CO_2$ and $NH_3$, as well as additionally fix two more $CO_2$ molecules to arrive at the same level of net carbon fixation as the synthetic bypass (see FIG. 1 and Table 3 comparison of photorespiratory pathways).

Whereas the vast majority of metabolic engineering efforts focus on introducing linear pathways for the anabolic production of molecules of interest, our approach introduces a self-sustaining metabolic cycle that fixes $CO_2$ when glycolate/glyoxylate is available.

We demonstrate that concomitant expression and activity of all six enzymes necessary to reconstitute the synthetic bypass can be achieved. This required heterologous expression of ~16 kbp of DNA and functional assembly of six multimeric enzymes ranging in molecular mass from 62-600 kDA.

However, an obvious physiological phenotype was not observed during growth experiments. The transformants exhibited only slight delay in growth when liquid cultures in air were inoculated from agar plates, but they reached the same doubling times and optical densities as the wild type.

Our results immediately suggest next steps toward improvement. For example, our initial design used enzymes derived from the thermophile *Chloroflexus* which are evolved to function at higher temperatures than the mesophilic growth conditions of plants and most cyanobacteria. This may underlie the low measured activity of heterologous PCS despite its strong overexpression in our transformants (FIG. 2B). Synthesis and assembly of such a large enzyme (~600 kDa) might impose a considerable stress on the transformant strains. Substitution by a PCS homolog from a mesophile may improve assembly and function of this trimeric enzyme in *S. elongatus*. Mining genome databases for mesophilic homologs of the six enzymes that may exhibit faster enzyme kinetics at lower temperatures could greatly improve flux through the cycle. However, characterization of these mesophilic alternatives is necessary, as our results with the much less efficient ApMCT homolog demonstrate. Nevertheless, mesophilic enzymes may still be advantageous in terms of expression and correct folding at ambient temperatures.

Likewise, an increase in ACCase activity may be required. Our present design relies on the native enzyme to fix bicarbonate. ACCase is required for fatty acid biosynthesis and endogenous levels of the enzyme may be insufficient to support optimal flux through the heterologously expressed cycle. However, overexpression of up to four separate subunits of the prokaryotic ACCases will significantly complicate DNA assembly and cloning strategies. Suitable alternatives may be eukaryotic ACCases, which have undergone gene fusion events creating one large single multi-functional gene (27).

In addition to the $C_2$ cycle, cyanobacteria can make use of two other strategies, the decarboxylation and glycerate pathways (28,29) that consume glyoxylate; they potentially compete with the synthetic bypass for substrate. In contrast, plants contain only the $C_2$ cycle, thus simplifying the fate of glyoxylate. With the localization of all six genes of our pathway to the chloroplast, only one additional enzyme, glycolate dehydrogenase, would be necessary to convert glyoxlate and bicarbonate to pyruvate. In fact, glycolate dehydrogenase has already been successfully targeted and expressed in chloroplasts of *Arabidopsis* (3).

Our results have implications beyond the optimization of photorespiration in plants and cyanobacteria. The successful introduction of half of the 3OHP bi-cycle into *S. elongatus* provides a platform in which to express the other half to attain the full bi-cyclic $CO_2$ fixation pathway. Given that $CO_2$ fixation limits the light-saturated rate of photosynthesis, the presence of two orthogonal $CO_2$ fixation pathways is expected to significantly enhance the conversion of solar energy into biomass. Although appealing, introducing the whole 3OHP bi-cycle will result in substantial carbon flux towards pyruvate, which could be detrimental to organisms that have evolved carbon metabolism based on sugar phosphates.

On the other hand, pyruvate or intermediates in the synthetic bypass could be redirected for biotechnological applications, such as biofuels or replacements for chemical feedstocks that are currently petroleum-derived (19). For example, we have shown that 3OHP, a precursor for bioplastics, can be derived from malonyl-CoA by the heterologous expression of MCR in cyanobacteria. Developing cyanobacteria as production strains requires increasing their tolerance to higher concentrations of 3OHP; this has been accomplished in *E. coli* (19). Likewise the production of propionyl-CoA by the combined function of MCR and PCS in the synthetic bypass could be useful for the production of diverse polyhydroxyalkanoates like polyhydroxyvalerate, polyhydroxymethylvalerate or co-polymers.

Improving photosynthesis holds promise for increasing the sustainable production of food and biofuel crops to meet the challenges of global climate change and population growth, but introducing new pathways and cycles constitutes a daunting challenge. The synthetic photorespiratory bypass reported in this study provides both a precedent and a platform for future bioengineering efforts.

The vast majority of metabolic engineering efforts focus on introducing linear pathways to generate products of interest; however, our proposed pathway is specifically aimed at introducing a self-sustaining metabolic cycle that fixes $CO_2$. Because of this inherent difference, optimization of expression levels adds a level of complexity. This is observed as increased expression of MCR and PCS with higher amounts of IPTG reduces growth (FIG. 3A).

In order to further characterize the effects of our pathway on growth, both the functional (pms4591) and non-functional (pms4570) pathways were introduced into a carboxysome mutant background (AK-0) which presumably produces more glyoxylate, as the carboxysome is involved decreasing RuBisCO oxygenase activity via the cyanobacterial CCM (15). In the mutant background, we demonstrate that transformants with the functional pathway display higher growth rates than transformants expressing the non-functional pathway (FIG. 3B).

One target for downstream enzyme that will need to be examined more closely in future work will be the role of acetyl-CoA carboxylase, as the cycle utilizes the endogenous copy to fix bicarbonate. As the cell is accustomed to solely using this enzyme for the producing malonyl-CoA, the primary building block for fatty acid biosynthesis, increased flux through this step may be necessary to optimize the heterologously expressed cycle. Furthermore, as demonstrated with the ApMCT homolog, mining genome databases for variants of the six enzymes which exhibits faster enzyme kinetics will also greatly improve the cycle. Finally, as we have now successfully introduced half of the 3-hydroxypropionate bicycle into Synechococcus, we now have a platform to express the other half and introduce the full bicycle, which would result in two truly separate and orthogonal carbon fixation pathways being expressed. Although appealing, given the concerns brought up by downstream metabolites produced from synthetic carbon fixation pathways, introducing the whole pathway may result in more pyruvate being generated, which could be detrimental to a cell that has not evolved to base its central carbon metabolism around pyruvate, rather than triose phosphates.

3-hydroxypropionate is an attractive chemical feedstock that may be used to replace chemicals that are currently petroleum-derived (11). One potential modification that can be made to our pathway is controlling the flux between MCR and PCS, where higher flux through MCR would result in an increase concentration of 3-hydroxypropionate in the cell, while still sustaining the orthogonal carbon fixation cycle. Generation of cyanobacterial strains that are more tolerant to higher concentrations of 3-hydroxypropionate, as has been done in E. coli (11), would facilitate this biotechnological use of generating bioplastics from a photoautotrophic source.

The conventional photorespiratory C2 cycle found in cyanobacteria in plants requires 10 ATP for the net fixation of two $CO_2$ molecules; however, during this process there is a net loss of one $CO_2$ and one ammonia molecule (refs). Comparatively, our engineered cycle requires six ATP for the net fixation of two bicarbonate molecules, with no net loss of carbon or nitrogen. Our results show that soluble expression and proper activity of all six genes necessary to reconstitute our pathway can be achieved; however, further studies are needed to optimize this pathway to yield higher growth rates in algae and plants. Concerning cyanobacteria, other than the C2 cycle, there are two other pathways, the decarboxylation and glycerate pathway, which use glyoxylate as a substrate, thus potentially competing with our pathway to use glyoxylate molecule in vivo. Plants only contain the C2 cycle, thus simplifying the fate of glyoxylate. With the localization of all six genes of our pathway to the chloroplast, only the addition of one enzyme, glycolate dehydrogenase, would be necessary to convert glyoxlate to pyruvate within the chloroplast, which has already been successfully targeted and expressed glycolate dehydrogenase to the chloroplast of Arabidopsis (2).

Materials and Methods:
Materials:

3-Hydroxypropionate was synthesized chemically from β-propiolactone. A solution (6 ml) of 5 M NaOH in water was stirred at room temperature and 1.25 ml β propiolactone was added drop-wise (0.025 mol). The solution was lyophilized and the dry powder was stored at room temperature.

Cloning, Strains, Growth Conditions:

All constructs were cloned using the BglBrick assembly format (11) in E. coli and subsequently cloned into various neutral site destination vectors, which allow for genomic integration into the S. elongatus genome by previously described transformation protocols (12,13). Plasmids, strains and primers that were generated and used are summarized in Tables 1 and 2.

S. elongatus strains were maintained in BG-11 medium under appropriate selection with constant light at 30 or 37° C.

Cloning, Heterologous Expression of Recombinant Enzymes in E. coli, and Purification—

The cloning, expression, and purification of the mesaconyl-C1-CoA hydratase (MCH) and mesaconyl-CoA C1:C4 CoA transferase (MCT) from C. aurantiacus was performed as previously described (9). Cloning, expression, and purification of the malyl-CoA lyase (MCL) from C. aurantiacus was described previously (14).

Heterologous Expression in E. coli, and Purification of ApMCT—

Competent E. coli BL21(DE3) cells were transformed with the plasmid pMct_Ap_JZ33, and 1 liter cultures were grown at 37° C. in LB medium with 100 μg ampicillin ml$^{-1}$. At an $OD_{600\ nm}$ of 0.6, the expression was induced with 1 mM IPTG. The cells were harvested after 4 h of growth and stored at −80° C. until use.

E. coli cells containing recombinant N-terminal $His_{10}$-tagged ApMCT were suspended in a two-fold volume of 50 mM Tris/HCl pH 7.5, 250 mM NaCl (buffer A). Cells were lysed by sonication (W-220F, Branson Ultrasonics) and the lysate was centrifuged for 40 min (40,000×g) at 4° C. A 1 ml HisTrap HP column (GE Healthcare) was equilibrated with buffer A. The cell extracts (40,000×g supernatants) were applied to the column at a flow rate of 1 ml min$^{-1}$. The column was washed with buffer A containing 100 mM imidazole to remove nonspecifically bound proteins. Recombinant His-tagged ApMCT was eluted with 500 mM imidazole in buffer A.

Cell Extracts.

Cells were harvested during exponential phase by centrifugation at 6000×g. The cell pellets were resuspended in a 2 fold volume of 200 mM MOPS/KOH buffer (pH 7.5). The cell suspensions were sonicated and the cell lysates were centrifuged at 20,000×g and 4° C. for 30 min. The supernatants were either used directly for enzyme assays or stored at −80° C.

High Performance Liquid Chromatography (HPLC).

A Waters 2695e system (Waters, Milford, Mass.) with a photo diode array detector (Waters 2998) was used. Reaction products and standard compounds were detected by UV absorbance at 260 nm. A reversed phase C18 column (SymmetryShield 4.6×250, Waters) was equilibrated at a flow rate of 0.6 ml min$^{-1}$ with 4% acetonitrile in 40 mM $K_2HPO_4$/HCOOH buffer (pH 4.2). A gradient of 26 min from 4 to 16% acetonitrile was applied. CoA-thioesters and free CoA were identified by retention times and UV spectra.

Enzyme Assays.

Malonyl-CoA reductase was measured using a spectrophotometric assay described previously (Hügler 2002), which was modified. The malonyl-CoA dependent oxidation of NADPH was montitored at 30° C. at a wavelength of 365 nm ($\varepsilon_{365}$=3,400 M$^{-1}$ cm$^{-1}$) (Dawson 1986). The assay mixture (400 μl) contained 200 mM MOPS/KOH buffer (pH 7.5), 5 mM MgCl2, 0.4 mM NADPH, 1 mM malonyl-CoA, and cell extract. The reaction was started by addition of malonyl-CoA. Notably, two NADPH molecules are oxidized per one malonyl-CoA molecule that is reduced to 3-hydroxypropionate.

Propionyl-CoA synthase activity was either monitored spectrophotometrically or in an HPLC based assay. (i) The photometric assay described by Alber and Fuchs (Alber 2002) was slightly modified. The reaction mixture (400 μl) contained 200 mM MOPS/KOH buffer (pH 7.5), 0.4 mM NADPH, 5 mM 3-hydroxypropionate, 100 mM KCl, 2 mM ATP, 0.5 mM CoA, and cell extract. The reaction was started by addition of 3-hydroxypropionate and carried out at 30° C. (ii) The same reaction mixture was used for the HPLC based assay only with 1 mM of NADPH instead. Samples of 100 µl were withdrawn after different time points and stopped by addition of 10 µl formic acid. The samples were kept on ice before precipitated protein was removed by centrifugation at 16,000×g. The supernatants were subjected to HPLC analysis to confirm propionyl-CoA formation.

The concerted function of the malyl-CoA/β-methylmalyl-CoA/citramalyl-CoA lyase, mesaconyl-C1-CoA hydratase, mesaconyl-CoA C1:C4 CoA transferase, and mesaconyl-C4-CoA hydratase was demonstrated in an HPLC based assay. The reaction mixture (400 µl) contained 200 mM MOPS/KOH buffer (pH 7.5), 5 mM MgCl$_2$, 0.5 mM propionyl-CoA, 5 mM glyoxylate, and cell extract. The reaction started by addition of glyoxylate was carried out at 30° C. Samples of 100 µl volume were withdrawn after different time points and treated as described above and subjected to HPLC analysis to confirm the formation of acetyl-CoA or other CoA-thioester intermediates.

MCT activity was measured in an HPLC-based assay.

photoautotrophic growth by genetic engineering of synthetic carbon fixations may provide a solution. This study sets a precedent and platform for future engineering efforts. Table 3 attached shows an energy balance comparison of photorespiratory pathways to achieve the same level carbon gain as the presently described 3OHP bypass.

REFERENCES

1. Savir, Y., Noor, E., Milo, R., and Tlusty, T. (2010) Cross-species analysis traces adaptation of Rubisco toward optimality in a low-dimensional landscape. *Proc. Natl. Acad. Sci. U.S.A.* 107, 3475-3480
2. Tcherkez, G. G., Farquhar, G. D., and Andrews, T. J. (2006) Despite slow catalysis and confused substrate specificity, all ribulose bisphosphate carboxylases may be nearly perfectly optimized. *Proc. Natl. Acad. Sci. U.S.A.* 103, 7246-7251
3. Kebeish, R., Niessen, M., Thiruveedhi, K., Bari, R., Hirsch, H. J., Rosenkranz, R., Stabler, N., Schonfeld, B., Kreuzaler, F., and Peterhansel, C. (2007) Chloroplastic photorespiratory bypass increases photosynthesis and biomass production in *Arabidopsis thaliana*. *Nat. Biotechnol.* 25, 593-599

TABLE 2

DNA oligonucleotides used for cloning.

| ID | SEQ ID NO: | Name | Oligonucleotide |
|---|---|---|---|
| PS307 | 1 | psbA1 promoter | GCATAGAATTCATGAGATCTGTTTAGTGCGATCGC GGCAG |
| PS308 | 2 | psbA1 promoter | CTAGGGGATCCGGGCAAGAGTCTTAGTTAAAAACT CTTG |
| PS300 | 3 | Chloroflexus MCL | GCATAGAATTCATGAGATCTCTTGGAGGAATCCAT TAATGCGCAAGCTAGCTCACAACTTC |
| PS284 | 4 | Chloroflexus MCL | CTAGGGGATCCTCACAGACCATACGCCTGGGC |
| PS301 | 5 | Chloroflexus MCH | GCATAGAATTCATGAGATCTCTTGGAGGAATCCAT TA ATGAGCGCTAAAACCAATCCCGG |
| PS286 | 6 | Chloroflexus MCH | CTAGGGGATCCTCATCCCCGACGCGGCATC |
| PS302 | 7 | Chloroflexus MCT | GCATAGAATTCATGAGATCTCTTGGAGGAATCCAT TAATGAAGGGTATTCTCCACGGATTGC |
| PS288 | 8 | Chloroflexus MCT | CTAGGGGATCCCTACGCTGCCCGATCTGGCC |
| PS304 | 9 | Chloroflexus MEH | GCATAGAATTCATGAGATCTCTTGGAGGAATCCAT TAATGGCGTGGAGCCACCCG |
| PS290 | 10 | Chloroflexus MEH | CTAGGGGATCCTCATCCCCCCAACTCAACCGTC |
| PS299 | 11 | Chloroflexus MCR | GCATAGAATTCATGAGATCTCTTGGAGGAATCCAT TAATGAGCGGAACAGGACGACTGGC |
| PS292 | 12 | Chloroflexus MCR | CTAGGGGATCCTTACACGGTAATCGCCCGTCCG |
| PS740 | 13 | Chloroflexus PCS | CTAGCTAGCATATGATCGACACTGCGCCCCT |
| PS741 | 14 | Chloroflexus PCS | CTAGCTAAAGCTTCTACCGCTCGCCGGCCG |
| PS430 | 15 | Accumulibacter MCT | ATATATATACATATGGATGGCATTCTGAAGGG |
| PS431 | 16 | Accumulibacter MCT | ATATACTCGAG TTATGTCGGACCTGCCACC |
| JZ33F | 17 | pMct_Ap_JZ33 | ATATATATACATATGGATGGCATTCTGAAGGG |
| JZ33R | 18 | pMct_Ap_JZ33 | ATATACTCGAGTTATGTCGGACCTGCCACC |

With the growing attention on global warming and an emphasis on green technologies, the potential for improving 4. Pellicer, M. T., Badia, J., Aguilar, J., and Baldomà, L. (1996) glc locus of *Escherichia coli*: characterization of genes encoding the subunits of glycolate oxidase and the glc regulator protein. *J. Bacteriol.* 178, 2051-2059

5. Maier, A., Fahnenstich, H., Von Caemmerer, S., Engqvist, M. K. M., Weber, A. P. M., Fl,gge, U.-I., and Maurino, V. G. (2012) Glycolate oxidation in *A. thaliana* chloroplasts improves biomass production. *Front Plant Sci* 3, 38

6. Nogales, J., Gudmundsson, S., Knight, E. M., Palsson, B. O., and Thiele, I. (2012) Detailing the optimality of photosynthesis in cyanobacteria through systems biology analysis. *Proc Natl Acad Sci* 109, 2678-2683

7. Blankenship, R. E., Tiede, D. M., Barber, J., Brudvig, G. W., Fleming, G., Ghirardi, M., Gunner, M. R., Junge, W., Kramer, D. M., Melis, A., Moore, T. A., Moser, C. C., Nocera, D. G., Nozik, A. J., Ort, D. R., Parson, W. W., Prince, R. C., and Sayre, R. T. (2011) Comparing photosynthetic and photovoltaic efficiencies and recognizing the potential for improvement. *Science* 332, 805-809

8. Fuchs, G. (2011) Alternative pathways of carbon dioxide fixation: Insights into the early evolution of life? *Annu. Rev. Microbiol.* 65, 631-658

9. Zarzycki, J., Brecht, V., Müller, M., and Fuchs, G. (2009) Identifying the missing steps of the autotrophic 3-hydroxypropionate $CO_2$ fixation cycle in *Chloroflexus aurantiacus*. *Proc Natl Acad Sci* 106, 21317-21322

10. Mattozzi, M., Ziesack, M., Voges, M. J., Silver, P. A., and Way, J. C. (2013) Expression of the sub-pathways of the *Chloroflexus aurantiacus* 3-hydroxypropionate carbon fixation bicycle in *E. coli*: Toward horizontal transfer of autotrophic growth. *Metab Eng* 16, 130-139

11. Anderson, J. C., Dueber, J., Leguia, M., Wu, G., Goler, J., Arkin, A., and Keasling, J. (2010) BglBricks: A flexible standard for biological part assembly. *J Biol Eng* 4, 1

12. Mackey, S. R., Ditty, J. L., Clerico, E. M., and Golden, S. S. (2007) Detection of rhythmic bioluminescence from luciferase reporters in cyanobacteria. in *Circadian Rhythms* (Rosato, E. ed.), Humana Press. pp 115-129

13. Niederholtmeyer, H., Wolfstädter, B. T., Savage, D. F., Silver, P. A., and Way, J. C. (2010) Engineering cyanobacteria to synthesize and export hydrophilic products. *Appl. Environ. Microbiol.* 76, 6023-6023

14. Zarzycki, J., and Kerfeld, C. A. (2013) The crystal structures of the tri-functional *Chloroflexus aurantiacus* and bi-functional *Rhodobacter sphaeroides* malyl-CoA lyases and comparison with CitE-like superfamily enzymes and malate synthases. *BMC Struct. Biol.* 13, 28

15. Hugler, M., Menendez, C., Schägger, H., and Fuchs, G. (2002) Malonyl-coenzyme A reductase from *Chloroflexus aurantiacus*, a key enzyme of the 3-hydroxypropionate cycle for autotrophic $CO_2$ fixation. *J. Bacteriol.* 184, 2404-2410

16. Alber, B. E., and Fuchs, G. (2002) Propionyl-Coenzyme A Synthase from *Chloroflexus aurantiacus*, a key enzyme of the 3-hydroxypropionate cycle for autotrophic $CO_2$ fixation. *J. Biol. Chem.* 277, 12137-12143

17. Ducat, D. C., Sachdeva, G., and Silver, P. A. (2011) Rewiring hydrogenase-dependent redox circuits in cyanobacteria. *Proc Natl Acad Sci* 108, 3941-3946

18. Clerico, E. M., Ditty, J. L., and Golden, S. S. (2007) Specialized techniques for site-directed mutagenesis in cyanobacteria. in *Circadian Rhythms* (Rosato, E. ed.), Humana Press. pp 155-171

19. Lipscomb, T. W., Lipscomb, M. L., Gill, R. T., and Lynch, M. D. (2012) Metabolic engineering of recombinant *E. coli* for the production of 3-hydroxypropionate. in *Engineering Complex Phenotypes in Industrial Strains*, John Wiley & Sons, Inc. pp 185-200

20. Horswill, A. R., Dudding, A. R., and Escalante-Semerena, J. C. (2001) Studies of propionate toxicity in *Salmonella enterica* identify 2-methylcitrate as a potent inhibitor of cell growth. *J. Biol. Chem.* 276, 19094-19101

21. Keasling, J. D. (2010) Manufacturing molecules through metabolic engineering. *Science* 330, 1355-1358

22. García Martin, H., Ivanova, N., Kunin, V., Warnecke, F., Barry, K. W., McHardy, A. C., Yeates, C., He, S., Salamov, A. A., Szeto, E., Dalin, E., Putnam, N. H., Shapiro, H. J., Pangilinan, J. L., Rigoutsos, I., Kyrpides, N. C., Blackall, L. L., McMahon, K. D., and Hugenholtz, P. (2006) Metagenomic analysis of two enhanced biological phosphorus removal (EBPR) sludge communities. *Nat. Biotechnol.* 24, 1263-1269

23. Hesselmann, R. P., Werlen, C., Hahn, D., van der Meer, J. R., and Zehnder, A. J. (1999) Enrichment, phylogenetic analysis and detection of a bacterium that performs enhanced biological phosphate removal in activated sludge. *Syst. Appl. Microbiol.* 22, 454-465

24. Zarzycki, J., and Fuchs, G. (2011) Coassimilation of organic substrates via the autotrophic 3-hydroxypropionate bi-cycle in *Chloroflexus aurantiacus*. *Appl. Environ. Microbiol.* 77, 6181-6188

25. Hu, Z.-H., Yue, Z.-B., Liu, S.-Y., G.-P., S., and Yu, H.-Q. (2010) Anaerobic Digestion of Lignocellulosic Wastes by Rumen Microorganisms: Chemical and Kinetic Analyses. in *Environmental Anaerobic Technology: Applications and New Developments* (Fang, H. H. P. ed.), Imperial College Press, London. pp 259-278

26. Sharkey, T. D. (1988) Estimating the Rate of Photorespiration in Leaves. *Physiol. Plant* 73, 147-152

27. Sasaki, Y., Konishi, T., and Nagano, Y. (1995) The Compartmentation of Acetyl-Coenzyme A Carboxylase in Plants. *Plant Physiol* 108, 445-449

28. Eisenhut, M., Ruth, W., Haimovich, M., Bauwe, H., Kaplan, A., and Hagemann, M. (2008) The photorespiratory glycolate metabolism is essential for cyanobacteria and might have been conveyed endosymbiontically to plants. *Proc Natl Acad Sci* 105, 17199-17204

29. Zarzycki, J., Axen, S. D., Kinney, J. N., and Kerfeld, C. A. (2013) Cyanobacterial-based approaches to improving photosynthesis in plants. *J. Exp. Bot.* 64, 787-798

30. Eisenhut, M., Kahlon, S., Hasse, D., Ewald, R., Lieman-Hurwitz, J., Ogawa, T., Ruth, W., Bauwe, H., Kaplan, A., and Hagemann, M. (2006) The plant-like C2 glycolate cycle and the bacterial-like glycerate pathway cooperate in phosphoglycolate metabolism in cyanobacteria. *Plant Physiol* 142, 333-342

The above examples are provided to illustrate the invention but not to limit its scope. Other variants of the invention will be readily apparent to one of ordinary skill in the art and are encompassed by the appended claims. All accessions, publications, databases, and patents cited herein are hereby incorporated by reference for all purposes.

TABLE 3

Energy balance comparison of photorespiratory pathways to achieve the same level carbon gain as the 3OHP bypass

|  | 3OHP bypass (this study) | $C_2$ (glycolate) cycle (30) + Calvin cycle | glycerate bypass (3) + Calvin cycle | glycolate oxidation (5) + Calvin Cycle |
|---|---|---|---|---|
| glycolate dehydrogenase (cyanobacteria) | +2NAD(P)H | +2NAD(P)H | +2NAD(P)H |  |
| glycine decarboxylase |  | +1NADH −1$CO_2$ −1$NH_3$ |  |  |
| glutamine synthetase |  | −1ATP +$NH_3$ |  |  |
| glutamine oxoglutarate aminotransferase |  | −2Fdx$_{(red)}$ |  |  |
| hydroxypyruvate |  | −NADH |  |  |
| glycerate kinase |  | −1ATP | −1ATP |  |
| tartronic semialdehyde reductase |  |  | −1NADH |  |
| glyoxylate carboligase |  |  | −1$CO_2$ |  |
| malic enzyme |  |  |  | +NADPH −1$CO_2$ |
| pyruvate dehydrogenase |  |  |  | +NADH −1$CO_2$ |
| phosphoglycerate kinase |  | −6ATP | −6ATP | −8ATP |
| glyceraldehyde 3-phosphate dehydrogenase |  | −6NADPH | −6NADPH | +8NADPH |
| ribulose phosphate kinase |  | −3ATP | −3ATP | −4ATP |
| RubisCO |  | +3$CO_2$ | +3$CO_2$ | +4$CO_2$ |
| acetyl-CoA carboxylase | −2ATP +2$HCO_3^-$ |  |  |  |
| malonyl-CoA reductase | −4NADPH |  |  |  |
| propionyl-CoA synthase (AMP forming) | −4ATP equiv. −2NADPH |  |  |  |
| pyruvate phosphate dikinase (amp forming)* | −4ATP equiv. |  |  |  |
| BALANCE | +2$HCO_3^-$ −6ATP (−10ATP)* −4NAD(P)H | +2$CO_2$ −11ATP −4NAD(P)H −2 Fdx$_{(red)}$ | +2$CO_2$ −10ATP −5NAD(P)H | +2$CO_2$ −12ATP −6NAD(P)H |

*If pyruvate is used for the regeneration of 3-phosphoglycerate 2 more ATP equivalents are required per pyruvate molecule by pyruvate phosphate dikinase (AMP-forming). Only 6 ATP are required if pyruvate is channeled into other biosyntheses pathways than gluconeogenesis.

TABLE 4

JIB-3345US(2013-020-03)

PCS, *Chloroflexus aurantiacus* J-10-f1
>gi|29126583|gb|AAL47820.2|AF445079_1 propionyl-CoA synthase
[*Chloroflexus aurantiacus*]

SEQ ID NO: 19

MIDTAPLAPPRAPRSNPIRDRVDWEAQRAAALADPGAFHGAIARTVIHWYDPQHHCWIRFNESSQRWEGL

DAATGAPVTVDYPADYQPWQQAFDDSEAPFYRWFSGGLTNACFNEVDRHVTMGYGDEVAYYFEGDRWDNS

LNNGRGGPVVQETITRRRLLVEVVKAAQVLRDLGLKKGDRIALNMPNIMPQIYYTEAAKRLGILYTPVFG

GFSDKTLSDRIHNAGARVVITSDGAYRNAQVVPYKEAYTDQALDKYIPVETAQAIVAQTLATLPLTESQR

QTIITEVEAALAGEITVERSDVMRGVGSALAKLRDLDASVQAKVRTVLAQALVESPPRVEAVVVRHTGQ

EILWNEGRDRWSHDLLDAALAKILANARAAGFDVHSENDLLNLPDDQLIRALYASIPCEPVDAEYPMFII

YTSGSTGKPKGVIHVHGGYVAGVVHTLRVSFDAEPGDTIYVIADPGWITGQSYMLTATMAGRLTGVIAEG

SPLFPSAGRYASIIERYGVQIFKAGVTFLKTVMSNPQNVEDVRLYDMHSLRVATFCAEPVSPAVQQFGMQ

IMTPQYINSYWATEHGGIVWTHFYGNQDFPLRPDAHTYPLPWVMGDVWVAETDESGTTRYRVADFDEKGE

IVITAPYPYLTRTLWGDVPGFEAYLRGEIPLRAWKGDAERFVKTYWRRGPNGEWGYIQGDFAIKYPDGSF

TLHGRSDDVINVSGHRMGTEEIEGAILRDRQITPDSPVGNCIVVGAPHREKGLTPVAFIQPAPGRHLTGA

DRRRLDELVRTEKGAVSVPEDYIEVSAFPETRSGKYMRRFLRNMMLDEPLGDTTTLRNPEVLEEIAAKIA

TABLE 4-continued

JIB-3345US(2013-020-03)

EWKRRQRMAEEQQIIERYRYFRIEYHPPTASAGKLAVVTVTNPPVNALNERALDELNTIVDHLARRQDVA

AIVFTGQGARSFVAGADIRQLLEEIHTVEEAMALPNNAHLAFRKIERMNKPCIAAINGVALGGGLEFAMA

CHYRVADVYAEFGQPEINLRLLPGYGGTQRLPRLLYKRNNGTGLLRALEMILGGRSVPADEALELGLIDA

IATGDQDSLSLACALARAAIGADGQLIESAAVTQAFRHRHEQLDEWRKPDPRFADDELRSIIAHPRIERI

IRQAHTVGRDAAVHRALDAIRYGIIHGFEAGLEHEAKLFAEAVVDPNGGKRGIREFLDRQSAPLPTRRPL

ITPEQEQLLRDQKELLPVGSPFFPGVDRIPKWQYAQAVIRDPDTGAAAHGDPIVAEKQIIVPVERPRANQ

ALIYVLASEVNFNDIWAITGIPVSRFDEHDRDWHVTGSGGIGLIVALGEEARREGRLKVGDLVAIYSGQS

DLLSPLMGLDPMAADFVIQGNDTPDGSHQQFMLAQAPQCLPIPTDMSIEAAGSYILNLGTIYRALFTTLQ

IKAGRTIFIEGAATGTGLDAARSAARNGLRVIGMVSSSSRASTLLAAGAHGAINRKDPEVADCFTRVPED

PSAWAAWEAAGQPLLAMFRAQNDGRLADYVVSHAGETAFPRSFQLLGEPRDGHIPTLTFYGATSGYHFTF

LGKPGSASPTEMLRRANLRAGEAVLIYYGVGSDDLVDTGGLEAIEAARQMGARIVVVTVSDAQREFVLSL

GFGAALRGVVSLAELKRRFGDEFEWPRTMPPLPNARQDPQGLKEAVRRFNDLVFKPLGSAVGVFLRSADN

PRGYPDLIIERAAHDALAVSAMLIKPFTGRIVYFEDIGGRRYSFFAPQIWVRQRRIYMPTAQIFGTHLSN

AYEILRLNDEISAGLLTITEPAVVPWDELPEAHQAMWENRHTAATYVVNHALPRLGLKNRDELYEAWTAG

ER

MCR, *Chloroflexus aurantiacus* J-10-fl
>gi|42561982|gb|AAS20429.1| malonyl-CoA reductase
[*Chloroflexus aurantiacus*]
SEQ ID NO: 20

MSGTGRLAGKIALITGGAGNIGSELTRRFLAEGATVIISGRNRAKLTALAERMQAEAGVPAKRIDLEVMD

GSDPVAVRAGIEAIVARHGQIDILVNNAGSAGAQRRLAEIPLTEAELGPGAEETLHASIANLLGMGWHLM

RIAAPHMPVGSAVINVSTIFSRAEYYGRIPYVTPKAALNALSQLAARELGARGIRVNTIFPGPIESDRIR

TVFQRMDQLKGRPEGDTAHHFLNTMRLCRANDQGALERRFPSVGDVADAAVFLASAESAALSGETIEVTH

GMELPACSETSLLARTDLRTIDASGRTTLICAGDQIEEVMALTGMLRTCGSEVIIGFRSAAALAQFEQAV

NESRRLAGADFTPPIALPLDPRDPATIDAVFDWGAGENTGGIHAAVILPATSHEPAPCVIEVDDERVLNF

LADEITGTIVIASRLARYWQSQRLTPGARARGPRVIFLSNGADQNGNVYGRIQSAAIGQLIRVWRHEAEL

DYQRASAAGDHVLPPVWANQIVRFANRSLEGLEFACAWTAQLLHSQRHINEITLNIPANISATTGARSAS

VGWAESLIGLHLGKVALITGGSAGIGGQIGRLLALSGARVMLAARDRHKLEQMQAMIQSELAEVGYTDVE

DRVHIAPGCDVSSEAQLADLVERTLSAFGTVDYLINNAGIAGVEEMVIDMPVEGWRHTLFANLISNYSLM

RKLAPLMKKQGSGYILNVSSYFGGEKDAAIPYPNRADYAVSKAGQRAMAEVFARFLGPEIQINAIAPGPV

EGDRLRGTGERPGLFARRARLILENKRLNELHAALIAAARTDERSMHELVELLLPNDVAALEQNPAAPTA

LRELARRFRSEGDPAASSSSALLNRSIAAKLLARLHNGGYVLPADIFANLPNPPDPFFTRAQIDREARKV

RDGIMGMLYLQRMPTEFDVAMATVYYLADRNVSGETFHPSGGLRYERTPTGGELFGLPSPERLAELVGST

VYLIGEHLTEHLNLLARAYLERYGARQVVMIVETETGAETMRRLLHDHVEAGRLMTIVAGDQIEAAIDQA

ITRYGRPGPVVCTPFRPLPTVPLVGRKDSDWSTVLSEAEFAELCEHQLTHHFRVARKIALSDGASLALVT

PETTATSTTEQFALANFIKTTLHAFTATIGVESERTAQRILINQVDLTRRARAEEPRDPHERQQELERFI

EAVLLVTAPLPPEADTRYAGRIHRGRAITV

MCL, *Chloroflexus aurantiacus* J-10-fl
>gi|163667062|gb|ABY33428.1| HpcH/HpaI aldolase
[*Chloroflexus aurantiacus* J-10-fl]
SEQ ID NO: 21

MRKLAHNFYKPLAIGAPEPIRELPVRPERVVHFFPPHVEKIRARIPEVAKQVDVLCONLEDAIPMDAKEA

ARNGFIEVVKATDFGDTALWVRVNALNSPWVLDDIAEIVAAVGNKLDVIMIPKVEGPWDIHFVDQYLALL

TABLE 4-continued

JIB-3345US(2013-020-03)

EARHQIKKPILIHALLETAQGMVNLEEIAGASPRMHGFSLGPADLAASRGMKTTRVGGGHPFYGVLADPQ

EGQAERPFYQQDLWHYTIARMVDVAVAHGLRAFYGPFGDIKDEAACEAQFRNAFLLGCTGAWSLAPNQIP

IAKRVFSPDVNEVLFAKRILEAMPDGSGVAMIDGKMQDDATWKQAKVIVDLARMIAKKDPDLAQAYGL

```
MCH, Chloroflexus aurantiacus J-10-fl
>gi|163667061|gb|ABY33427.1| MaoC domain protein dehydratase
[Chloroflexus aurantiacus J-10-fl]
                                                       SEQ ID NO: 22
```
MSAKTNPGNFFEDFRLGQTIVHATPRTITEGDVALYTSLYGSRFALTSSTPFAQSLGLERAPIDSLLVFH

IVFGKTVPDISLNAIANLGYAGGRFGAVVYPGDTLSTTSKVIGLRQNKDGKTGVVYVHSVGVNQWDEVVL

EYIRWVMVRKRDPNAPAPETVVPDLPDSVPVTDLTVPYTVSAANYNLAHAGSNYLWDDYEVGEKIDHVDG

VTIEEAEHMQATRLYQNTARVHFNLHVEREGRFGRRIVYGGHIISLARSLSFNGLANALSIAAINSGRHT

NPSFAGDTIYAWSEILAKMAIPGRTDIGALRVRTVATKDRPCHDFPYRDAEGNYDPAVVLDFDYTVLMPR

RG

```
MCT, Chloroflexus aurantiacus J-10-fl
>gi|163667063|gb|ABY33429.1| L-carnitine dehydratase/bile acid-
inducible protein F [Chloroflexus aurantiacus J-10-fl]
                                                       SEQ ID NO: 23
```
MKGILHGLRVVEGSAFVAAPLGGMTLAQLGADVIRFDPIGGGLDYKRWPVTLDGKHSLFWAGLNKGKRSI

AIDIRHPRGQELLTQLICAPGEHAGLFITNFPARGWLSYDELKRHRADLIMVNLVGRRDGGSEVDYTVNP

QLGLPFMTGPVTTPDVVNHVLPAWDIVTGQMIALGLLAAERHRRLTGEGQLVKIALKDVGLAMIGHLGMI

AEVMINDTDRPRQGNYLYGAFGRDFETLDGKRVMVVGLTDLQWKALGKATGLTDAFNALGARLGLNMDEE

GDRFRARHEIAALLEPWFHARTLAEVRRIFEQHRVTWAPYRTVREAIAQDPDCSTDNPMFAMVEQPGIGS

YLMPGSPLDFTAVPRLPVQPAPRLGEHTDEILLEVLGLSEAEVGRLHDEGIVAGPDRAA

```
MEH, Chloroflexus aurantiacus J-10-fl
>gi|163667068|gb|ABY33434.1| conserved hypothetical protein
[Chloroflexus aurantiacus J-10-fl]
                                                       SEQ ID NO: 24
```
MSSADWMAWIGRTEQVEDDICLAQAIAAAATLEPPSGAPTADSPLPPLWHWFYFLPRAPQSLSSDGHPQ

RGGFIPPIPYPRRMFAGARIRFHHPLRIGQPARREGVIRNITQKSGRSGPLAFVTVGYQIYQHEMLCIEE

EQDIVYREPGAPVPAPTPVELPPVHDAITRTVVPDPRLLFRFSALTFNAHRIHYDRPYAQHEEGYPGLVV

HGPLVAVLLMELARHHTSRPIVGFSFRSQAPLFDLAPFRLLARPNGDRIDLEAQGPDGATALSATVELGG

```
Homologs:
MCR homolog, Erythrobacter sp. NAP1
>gi|85689647|gb|EAQ29650.1| NAD-dependent epimerase/dehydratase:
Short-chain dehydrogenase/reductase SDR [Erythrobacter sp. NAP1]
                                                       SEQ ID NO: 25
```
MSKEGNAAKGRLEGKVALITGAAGNLGNEISRAFAREGAFVVMTGRTEERISAAREQLIADTGVAPERID

TAVLDGGNPDSIRAAMAKLRKEYGRIDILINNAGSAGPKQPLHNVPLSPQEMEACGDTETVRDAMLNILG

VTWNMARIVAPMMPVGGAMVNISTIFSHTRYYGRTAYVVPKAALNALSNQLASELGPRGIRVNTVFPGPI

ESDRIRTVFAAMDEVQSQPKDTTANYFTGRMALTRSVNGKVDGKPLPNPKDIAGTCLFLASEEAAGIAGE

EVDVTHGLSANRTSASTYMTRPSMRSLDGAGLNIFIVSGENWDDALVAAHTLIGSGAKVRLGLARNADVA

QANARLKAQGIGEELTVTRFNRAEPDAMEDALAAFSGDVDGAITGAIILPVKPSGHFTGSLLAADDDTVT

KFMDTELVGAIAVSRSLARYWHGREDLQSPPRCVFMTNPGDPLGNSFASVLSAGITQLIRIWRDEERVQA

GNGSTEHAVWSNQIVRHTNTEDENTRFASGHATRVLFREQHIAEIDLKLPANISEETGSRKAMVGFAENI

TGLHLGKVAFITGGSAGIGGQVARLLALAGAKVMMVARRESELVAARDRIVGELQDIGFAGVERRVKYMA

DIDVSDFASLDKAVDATLEEFGRIDYLINNAGVAGAEDMVIDMEPEAWRFTLDANLISNYHLMQRVVPLM

KEQGSGYVLNVSSYFGGEKFLAVAYPNRADYGLSKAGQRAMVEAFSPFLGPEVQCNAIAPGPVDGDRLSG

TABLE 4-continued

JIB-3345US(2013-020-03)

TGGKPGLFQRRAKLILENKRLNAVYSAVIHAIREGGDAAKILTRLSRNSTSTLSHDAEAPEELRKLALDF

ASQGDGLCTWDQYLLTDAMAQRLLVRLQLGGFLLGSNEWASLSSSEQTWLKLSPPDDKPFLPAAQVDKVA

NGVGKGVISQLHLGAMPTEAEVAQATVFFLADRAVSGETFMPSGGLRVERSNTEREMFGSPKQERIDKMK

GKTVWIIGEHLSDYVAATIEELVSGCGVAKVVLIAKDKSGEKAVRDQLPNDLSKDALEVLIAGDGLEEAM

DEALGHWGKPTTVLSMPGEPLPDHLFEGGNPLSTKDFAHMVEANITRHYRVTRKASLYDGCQVVLVSPDV

PYGSDGPGVALANFVKTSLHAFTATVAVENERLVHDVPVNQINLTRRVSSEEPRDADEHAEELRRFTRAV

LLVGAPLPDAQDSRYRSKIYRGTSMTV

PCS homolog, *Erythrobacter* sp. NAP1
>gi|85689648|gb|EAQ29651.1| acetyl-coenzyme A synthetase
[*Erythrobacter* sp. NAP1]
SEQ ID NO: 26

MIGEGDDIGSSNNLEKQSHGLRISDRDHFQRLREECRSDPGEFHGRLAKREICWLIEGPGGNPAWAFYDD

AAETWTGWDASSAAPITLDLPESFEPWERAFNDDDPPNWRWFEGGLTSTAFNEVDRHVLSGHGDEAAMIF

EGDRWNMASEGGRGGPVDSEVISRRKLLLESAKCALALKALGLEAGDRIALNMPSIPEQIYWTEGAKRMG

IVYTPVFGGFSDKTLSDRIADAGARVVVTADGSYRNAQMVPFKPSYTDPALDNFIAVPVAMELLGQALED

GELVVAPEHAGLIRSEVAGLLDGEVTVERSDVMRGVGKALTAIASGEAAGGAMTPRQAAQLRIAIASALV

DSPPRVDAVVVVKHTAQPDLPWNEARDHWSHDLTAAAGEELLKAARDAGFDVADEEALLALSDTEFVRAI

WAGAPVLAVDAEYPNFIIYTSGSTGKPKGVVHVHGGYASGVAATMPAAFGAEPGDVMYVVADPGWITGQS

YQIAASLLSRVTTVITEGSPVFPHAGRFASIIERYGVNVFKAGVTFLKSVMQNPENLKDIQRYDLSSLKV

ATFCAEPVSPAVQAFAMEHITHRYINSYWATEHGGMVWTHFADADGFPLEADAHTYPLPWIMGDVWVEDA

DGSSNGPVEYERDTGTGGAPWRVAEDGEKGEIVIALPYPYLTRTIWGDVENFTVEHVGNLARVAGGWRGD

EVRYADTYWRRWKGAWAYTQGDFAMRHPDGSFSLHGRSDDVINVSGHRIGTEEIEGAILRDKALDPNSPV

GNVIVIGAPHSQKGVTPIAFVTPVEGRRLTQDDKRRLTDLVRTEKGAVAVPQDFIELSEFPETRSGKYMR

RMVRAVVEGGEVGDASTLRNPESLDELARAVDGWKRRQSLSDTQALFERYRFFTIQYNLVAPGKRVATVT

VKNPPVNALNERALDELVIIAEHLARKDDVAAVVFTGSGTASFVAGADIRQMLEEVNSVEEAKALPDNAQ

LAFRTIEEMDKPCIAAIQGVALGGGMEFALACHYRVAEPKARFGQPEINLRLLPGYGGTQRLPRLLADGG

GETGLRDALDLILGGRAIDADAALAVGAVDALADGSDNALSHAHAMVREFVRSGDDSALGKAFAARKTQT

QSWHEPASIDLDAVLEDEFLQRILNQLEWAGRDKAGERALDAVRTGWTQGMTAGLECEAQRFAEAIIDPE

GGKTGIQQFMDKQSPPLPVRRDGVWEDDQHEATKTALIEAGDLLPLGAPFYPGVTAIPPKQLAFGIARDP

DTGAPRFGPPETHERELVVNTPKPGANEALIYLLSSEVNFNDIWALTGIPVSPFDAHDEDVQITGSGGLA

LVAALGSELKEEGRLQVGDLVSVYSGTSELLSPLAGDDPMYAGFAIQGYETKTGSHAQFLTVQGPQLHRP

PADLTLEQAGAYTLNLGTVARCLFTTLEIQAGKTAFVEGSATGTGLDALKSSVRTGLAVTGLVSSEDRAE

FVKSHGSVGAINRKDPEIADCFTPVPDDPDEARQWEADGEKLLDAYRETNGGKLADYVVSHAGERAFPRS

FQLLAEGGRLAFYGASSGYHFSFMGKGGEARPDEMLARANLRGGESVLLYYGPGSHELADEKGLEMVEAA

RLMKARMVIVTTSDGQREFLQSLGLEDAVEGIVSIEGLKRRLSDFHWPDTLPRLPDARTDIENFKIGVRA

YQQNTMKPFGTAVGKLLRSPGNPRGVPDLVIERAGQDTLGVSTSLVKPFGGRVIYAEEMAGRRYTFYAPQ

VWTRQRRIYMPSAEIFGTHLCNAYEVTMMNEMVAAGLLDVTEPTMVPWEGLPEAHQAMWDNRHSGATYVV

NHALPAMGLITKDELLEYWVAAQSDTGETS

TABLE 4-continued

JIB-3345US(2013-020-03)

MCL homolog, *Candidatus 'Accumulibacter phosphatis'*
>gi|257046607|gb|ACV35795.1| HpcH/HpaI aldolase [*Candidatus Accumulibacter phosphatis* clade IIA str. UW-1]
SEQ ID NO: 27

MKLPVHFYKPLAIGAPQPLRELPVRPERMIHFFPPHIDKIRAKAPETARQCDVMCGNLEDAIPIEAKDAA

RAGFIDLLAAHDFGDTAMWVRVNALNSPWVLDDLNEIIKHVGNKVDVIMIPKVEGPWDIHFVDQYVSLLE

AKYAIRKPILLHALLETAQGVTNVEAICGASPRMHGLSLGPADLAASRGMKTTRVGGGHPGYGVLADPEA

GQDGGEKQRAFFQQDLWHYTVARMVDAAVAHGLRSFYGPFGDLKDEAACEAQFRNAFLMGCSGAWSLAPN

QIAIAKRVFSPDVKEVLFAKRILEAMPDGSGVATIDGKMQDDATWKQAKVIVDLARLVARRDPELAAAYG

W

MCH homolog, *Candidatus 'Accumulibacter phosphatis'*
>gi|257046608|gb|ACV35796.1| MaoC domain protein dehydratase [*Candidatus Accumulibacter phosphatis* clade IIA str. UW-1]
SEQ ID NO: 28

MSEKTRLGNFFEDFQIGQTIAHATPRTISEGDVALYTALTGSRFAITSSDTFAYSLGFPRAPVDNLLAFN

VVFGKTVPDISLNAVANLGYAAGRFGHRVFVGDTLTADSTVIGLKENRDGQTGIVYVRSCGINQHQQIAL

DYCRWVMVRKREPKSPAPPACVPDLPEAVAAGDLIVPAGIRVDQYDCTLSGNPDLWDDYEVGERIDHVDG

MTIEESEHMMATRLYQNTARVHFNQQAESAGRFGRRIIYGGCIISLARSLSFNGLANAFLVAAINGGRHV

TPTFAGDTIYAWSEVVDKMVLPGRNDLGALRLRTVATKDRPCADFPCKTADGSYDPSVVLDFDYTTLIPR

RA

MCT homolog, *Candidatus 'Accumulibacter phosphatis'*
>gi|257046606|gb|ACV35794.1| acyl-CoA transferase/carnitine dehydratase-like protein [*Candidatus Accumulibacter phosphatis* clade IIA str. UW-1]
SEQ ID NO: 29

MDGILKGLRVVEGSAFVAAPLGGMTLAQLGADVIRFDPIGGGLDYRRWPLTLDGRHSLFWAGLNKGKRSI

AVDLRLPRGQELLTQLICAPGDHAGLFSTNFPAKGWLAYEALQAHRQDLIMVNLTGRRDGGSEVDYTLNP

QLGLPLMTGPTSSPEVVNHVFPAWDFISGQMIALGLLAAERHRRLTGEGQLVRLALKDVALAMLGNFGML

AEAMVNGADRPRQGNYLYGAFGRDFGTLDGRRLMVVGLTGMQWRRLVKATGLREPISELAARLGLDFDDE

GNRYRARQEIARLFEPWFHARTLAEAALTLDAHGVTWGPYRSVREEVAADPDCSTDNPMFTLTEQPGIGR

YLMPSTPLDFAGVPRLPAMPAPRLGEHTDQILLDILGLSEAEVGRLHDARVVAGPT

MEH homolog, *Candidatus 'Accumulibacter phosphatis'*
>gi|257046603|gb|ACV35791.1| conserved hypothetical protein [*Candidatus Accumulibacter phosphatis* clade IIA str. UW-1]
SEQ ID NO: 30

MTESRIPYTQWIGRHEITDDDLGLAPALAAAATFDDTVTPLGNGSALPPLWHWFYFLPKTPQALLGVDGH

PQRGGFMPPIPYPRRMFAGARLRFHRPLIIGQPARREAVIRDIKEKSGRSGSLAFVSVLCRFYQDGALCI

EEEQDIVYREPGPAVACPRVIDWPPLPSCVWSRIVEPEPRLLFRFSALTFNAHRIHYDRPYAINEEGYPG

LVVHGPLTAVLLMELLRRETAQAVLDYSFRGLAPLFDLAPFRLVGTLVDGRVSLEAQGPDGAAAMRASAE

LAPA

>PMS4570
SEQ ID NO: 31 gatctcttggaggaatccattaATGagcggaacaggacgactggcaggaaagattgcgttaattaccggt ggcgccggcaatatcggcagtgaattgacacgtcgctttctcgcagagggagcgacggtcattattagtg gacggaatcgggcgaagttgaccgcactggccgaacggatgcaggcagaggcaggagtgccggcaaagcg catcgatctcgaagtcatggatgggagtgatccggtcgcggtacgtgccggtatcgaagcgattgtggcc cgtcacggccagatcgacattctggtcaacaatgcaggaagtgccggtgcccagcgtcgtctggccgaga ttccactcactgaagctgaattaggccctggcgccgaagagacgcttcatgccagcatcgccaatttact TABLE 4-continued

JIB-3345US(2013-020-03)

tggtatgggatggcatctgatgcgtattgcggcacctcatatgccgtaggaagtgcggtcatcaatgtc
tcgaccatcttttcacgggctgagtactacgggcggattccgtatgtcacccctaaagctgctcttaatg
ctctatctcaacttgctgcgcgtgagttaggtgcacgtggcatccgcgttaatacgatctttcccggccc
gattgaaagtgatcgcatccgtacagtgttccagcgtatggatcagctcaaggggcggcccgaaggcgac
acagcgcaccatttttgaacaccatgcgattgtgtcgtgccaacgaccagggcgcgcttgaacgtcggt
tcccctccgtcggtgatgtggcagacgccgctgtctttctggccagtgccgaatccgccgctctctccgg
tgagacgattgaggttacgcacggaatggagttgccggcctgcagtgagaccagcctgctggcccgtact
gatctgcgcacgattgatgccagtggccgcacgacgctcatctgcgccggcgaccagattgaagaggtga
tggcgctcaccggtatgttgcgtacctgtgggagtgaagtgatcatcggcttccgttcggctgcggcgct
ggcccagttcgagcaggcagtcaatgagagtcggcggctggccggcgcagactttacgcctcccattgcc
ttgccactcgatccacgcgatccggcaacaattgacgctgtcttcgattgggggccggcagaataccg
gcgggattcatgcagcggtgattctgcctgctaccagtcacgaaccggcaccgtgcgtgattgaggttga
tgatgagcgggtgctgaattttctggccgatgaaatcaccgggacaattgtgattgccagtcgcctggcc
cgttactggcagtcgcaacggcttaccccggcgcacgtgcgcgtgggccgcgtgtcattttctctcga
acggtgccgatcaaaatgggaatgtttacggacgcattcaaagtgccgctatcggtcagctcattcgtgt
gtggcgtcacgaggctgaacttgactatcagcgtgccagcgccgccggtgatcatgtgctgccgccggta
tgggccaatcagattgtgcgcttcgctaaccgcagccttgaagggttagaatttgcctgtgcctggacag
ctcaattgctccatagtcaacgccatatcaatgagattaccctcaacatccctgccaacattagcgccac
caccggcgcacgcagtgcatcggtcggatgggcggaaagcctgatcgggttgcatttggggaaagttgcc
ttgattaccggtggcagcgccggtattggtgggcagatcgggcgcctcctggctttgagtggcgcgcgcg
tgatgctggcagcccgtgatcggcataagctcgaacagatgcaggcgatgatccaatctgagctggctga
ggtggggtataccgatgtcgaagatcgcgtccacattgcaccgggctgcgatgtgagtagcgaagcgcag
cttgcggatcttgttgaacgtaccctgtcagcttttggcaccgtcgattatctgatcaacaacgccggga
tcgccggtgtcgaagagatggttatcgatatgccagttgagggatggcgccatacccttcttcgccaatct
gatcagcaactactcgttgatgcgcaaactggcgccgttgatgaaaaaacagggtagcggttacatcctt
aacgtctcatcatactttggcggtgaaaaagatgcggccattccctaccccaaccgtgccgattacgccg
tctcgaaggctggtcagcgggcaatggccgaagtctttgcgcgcttccttggcccggagatacagatcaa
tgccattgcgccgggtccggtcgaaggtgatcgcttgcgcggtaccggtgaacgtcccggcctctttgcc
cgtcgggcgcggctgattttggagaacaagcggctgaatgagcttcacgctgctcttatcgcggctgcgc
gcaccgatgagcgatctatgcacgaactggttgaactgctcttacccaatgatgtggccgcactagagca
gaatcccgcagcacctaccgcgttgcgtgaactggcacgacgttttcgcagcgaaggcgatccggcggca
tcatcaagcagtgcgctgctgaaccgttcaattgccgctaaattgctggctcgtttgcataatggtggct
atgtgttgcctgccgacatctttgcaaacctgccaaacccgcccgatcccttcttcacccgagcccagat
tgatcgcgaggctcgcaaggttcgtgacggcatcatgggatgctctacctgcaacggatgccgactgag
tttgatgtcgcaatggccaccgtctattaccttgccgaccgcaatgtcagtggtgagacattccacccat
caggtggtttgcgttacgaacgcacccctaccggtggcgaactcttcggcttgccctcaccggaacggct
ggcggagctggtcggaagcacggtctatctgataggtgaacatctgactgaacaccttaacctgcttgcc
cgtgcgtacctcgaacgttacggggcacgtcaggtagtgatgattgttgagacagaaaccggggcagaga
caatgcgtcgcttgctccacgatcacgtcgaggctggtcggctgatgactattgtggccggtgatcagat

TABLE 4-continued

JIB-3345US(2013-020-03)

cgaagccgctatcgaccaggctatcactcgctacggtcgcccagggccggtcgtctgtacccccttccgg ccactgccgacggtaccactggtcgggcgtaaagacagtgactggagcacagtgttgagtgaggctgaat ttgccgagttgtgcgaacaccagctcacccaccatttccgggtagcgcgcaagattgccctgagtgatgg tgccagtctcgcgctggtcactcccgaaactacggctacctcaactaccgagcaatttgctctggctaac ttcatcaaaacgacccttcacgcttttacggctacgattggtgtcgagagcgaaagaactgctcagcgca ttctgatcaatcaagtcgatctgacccggcgtgcgcgtgccgaagagccgcgtgatccgcacgagcgtca acaagaactggaacgttttatcgaggcagtcttgctggtcactgcaccactcccgcctgaagccgatacc cgttacgccgggcggattcatcgcggacgggcgattaccgtgtaaGGATCTGTTTAGTGCGATCGCGGCA

GGACTTAACTGAGCTTCAGAGAAGACGCAGGGACTTCATCCCAAGAAGCCACTGTCCGCAATTGGGCACG

CCAGCCGTTGGCCCGCTGTTCTGGTGTCAGATTGCGCTCAAAGGACTCATGGCAGTCGCGAGCCTGCTGC

TCGTCGCAAGTCGCAATGCACGAGTAAAGAATGCCCGCCGGGTCGAATTGTTCATTTACCCAAATCACTT

TGTCGGTTGCCATAGGGGGTTGCTCCTACGCTCAGCTGGATTTAGCGTCTTCTAATCCAGTGTAGACAGT

AGTTTTGGCTCCGTTGAGCACTGTAGCCTTGGGCGATCGCTCTAAACATTACATAAATTCACAAAGTTTT

CGTTACATAAAAATAGTGTCTACTTAGCTAAAAATTAAGGGTTTTTTACACCTTTTTGACAGTTAATCTC

CTAGCCTAAAAAGCAAGAGTTTTTAACTAAGACTCTTGCCCGGATCTcttggaggaatccattaatgcgc aagctagctcacaacttctacaaaccgttggccatcggtgctccggagccgatccgcgagctgccggttc gcccagagcgggtcgtccacttttttccgccccacgtggaaaagattcgcgcccgtattcccgaagtcgc caaacaggttgatgtgctgtgcggcaatctggaagacgcgattccgatggacgccaaagaggccgcccgc aacggctttatcgaggtagtcaaagcaaccgatttcggcgataccgcgctctgggtgcgggtcaatgcgc tcaacagcccatgggtgctcgacgatattgccgagattgtggccgcggtgggcaataaactcgatgtgat tatgatcccgaaggtcgaggggccgtgggacattcacttcgttgatcagtatctggcgctgctcgaagcc cgccaccagatcaaaaagccgattctgatccatgctctgctagaaaccgcccagggcatggtcaatctgg aagaaattgccggtgccagcccccgcatgcacggcttcagtctggggccggctgatctcgccgcttcgcg tggcatgaagaccacccgtgtcggcggtgggcaccccttctacggcgtgctggccgaccgcaagaaggt caggccgagcggccattctatcagcaagacctctggcactacacgattgcgcggatggttgatgtggcag ttgcccatggcctgcgcgccttctacggcccttcggcgacatcaaggatgaagccgcctgcgaagccca attccgcaacgccttcctcctcggctgcaccggtgcgtggtcgctcgcgcccaaccagattcccatcgcc aagcgcgtcttcagcccggacgtgaacgaggtgctcttcgccaaacgcatcctggaggcgatgcccgatg gttcgggggtggcgatgattgacggcaagatgcaagacgatgcgacctggaagcaggcgaaggtgatcgt tgatctggcgcggatgattgcgaagaaagaccccgacctggcccaggcgtatggtctgtgaGGATCTctt ggaggaatccattaatgagcgctaaaaccaatcccggcaacttcttcgaggattttcggcttggtcagac gattgtccacgccacgccgcgcacgattaccgaaggcgacgttgccctctacacgtcgctgtacggttcc cgctttgcgcttacctcatcaaccccctttgcgcaatcgttggggctggagcgagcgccgattgatagcc tgctggtgtttcatatcgtcttcggtaagacggtacccgacatctcgctcaacgcgattgccaatctcgg ctacgccggtggacgctttggcgcagtggtctaccccggcgacacccttccaccacttcaaaggtgatc ggtttgcgcagaacaaagacggcaaaaccggtgtggtgtatgtccactcggtgggggtgaaccaatggg acgaggtcgtgctcgaatacatccgctgggtgatggtgcggaagcgcgacccgaacgcaccggcaccgga gacggttgtccccgacctgcccgactcggtaccggtcaccgatttgaccgtcccgtacaccgtatcggcg gcgaactacaatctggcccacgccggcagcaactacctctgggacgattacgaggtgggtgagaagatcg

TABLE 4-continued

JIB-3345US(2013-020-03)

atcacgtggacggggtcacgattgaggaggccgagcacatgcaggcgacccggctctaccagaacacagc gcgggtccacttcaacctccacgttgagcgggaagggcggtttggccggcggatcgtgtacggcggccac atcatcagcctggcgcgttcgttgtcgttcaacgggctggccaatgcgctgagcattgcggccatcaaca gcgggcgccacaccaaccccagctttgccggcgacacgatctacgcctggtcagagattcttgccaagat ggcgattccgggccgcaccgatattggcgccttgcgggtacgtaccgtcgccaccaaagatcgcccgtgt cacgattttccctaccgtgacgcggaggggaactacgatccggcggtggtgcttgattttgattacacag tattgatgccgcgtcggggatgaGGATCTctcaacaGGCCTGCtggtaatcGCAGGCCtttttttttGGA

TCTGTTTAGTGCGATCGCGGCAGGACTTAACTGAGCTTCAGAGAAGACGCAGGGACTTCATCCCAAGAAG

CCACTGTCCGCAATTGGGCACGCCAGCCGTTGGCCCGCTGTTCTGGTGTCAGATTGCGCTCAAAGGACTC

ATGGCAGTCGCGAGCCTGCTGCTCGTCGCAAGTCGCAATGCACGAGTAAAGAATGCCCGCCGGGTCGAAT

TGTTCATTTACCCAAATCACTTTGTCGGTTGCCATAGGGGGTTGCTCCTACGCTCAGCTGGATTTAGCGT

CTTCTAATCCAGTGTAGACAGTAGTTTTGGCTCCGTTGAGCACTGTAGCCTTGGGCGATCGCTCTAAACA

TTACATAAATTCACAAAGTTTTCGTTACATAAAAATAGTGTCTACTTAGCTAAAAATTAAGGGTTTTTTA

CACCTTTTTGACAGTTAATCTCCTAGCCTAAAAAGCAAGAGTTTTTAACTAAGACTCTTGCCCGGATCTc ttggaggaatccattaatgaagggtattctccacggattgcgtgtagtggagggatcggcctttgttgcc gcaccgctgggggcatgacgctcgcgcagttgggggccgatgtgattcgcttcgaccctatcggcggcg gtctcgattataaacgctggccggttacgctcgacggtaagcatagtctgttttgggccggtctcaacaa gggcaaacgttcgattgcgattgatattcgccatccacgcgggcaggagttgctgacgcagcttatctgc gcacccggcgagcatgccggtctctttattaccaattttccggcgcgcggttggttgagttacgatgagc tgaagcgtcaccgcgccgacctgattatggtcaatctggtcgggcggcgcgatggcgggtcagaggtgga ttacaccgttaacccgcagttggggctgccgtttatgaccggcccggtcacgacgcctgatgtggttaat cacgtgctgccggcctgggatattgtgaccgggcagatgattgcgctcggtctgctggctgccgagcgtc accgtcggctgaccggtgaggggcaactggtgaagattgcgctgaaggatgtcgggctggcgatgatcgg ccatctggggatgattgccgaggtgatgatcaacgataccgaccgtccacggcaggggaattatctctac ggggcgttcgggcgcgatttcgagaccctcgatgggaagcgggtgatggtggttggtttgaccgatttgc agtggaaggcgctgggcaaggcgaccggtctgacggatgcgttcaatgcgctcggtgcgcggctggggct gaatatggacgaggaaggcgaccgcttccgtgcccgccacgagatcgctgcgctgcttgaaccctggttc cacgcccgcacgctggccgaggtacgacgcatctttgaacagcaccgcgtcacctgggcgccgtaccgca cggtacgggaagcgattgcccaggaccccgactgctccaccgataacccgatgtttgcgatggtcgagca gcccggcattgggagctacctgatgccgggttcgccgctggatttcactgccgtcccgcgtctgcctgtc cagcctgcgccccggctcggcgagcacaccgatgagattttgctggaggtgctgggcttgagtgaagctg aagtcggtcgcttgcacgatgaagggattgtggccgggccagatcgggcagcgtagGGATCTcttggagg aatccattaatgagcagcgcggattggatggcctggattgggcgtactgagcaggtggaagatgatattt gtctggcccaggcgattgccgcagccgcaacgcttgagccgcgtcgggagcaccaactgcggatagtcc gctccctccgctctggcactggttttactttctgccccgtgccccacagtcgcagctcagcagtgatggt catccgcagcgcggcggctttatcccaccgataccctatccacgccgcatgtttgccggtgcccgcatcc gctttcatcacccgctgcgcatcggccaaccggcgcgtcgtgaaggtgtgatccgcaacatcactcaaaa aagcggtcgcagcgggccgctggcatttgtgacggtcggctaccagatataccaacatgagatgctttgt atcgaagaagagcaagacatcgtgtaccgtgagccgggggcaccggtgccggcccccacaccggtagagt TABLE 4-continued

JIB-3345US(2013-020-03)

taccaccggtacacgatgcaatcacccgtactgttgtgcccgatccgcgtctgctctttcgcttctcagc cctcaccttcaatgcgcatcggattcactacgaccggccatacgctcagcacgaagagggctatccgggc ctggtcgtgcatggccccctggtagcagtcctgctaatggaactggcccgtcaccatacatcccgcccga ttgttggcttttcgttccgcagccaggcgccactcttcgatctggccccttccgcctgctggcccgccc caacggcgaccgcatcgatctggaagcacagggacctgacggggcaacggcgctcagcgcgacggttgag ttgggggatgaGGATCTCtcaacaGGCCTGCtggtaatcGCAGGCCttttttttG

>PMS4591

SEQ ID NO: 32

GATCTATGGATGGCATTCTGAAGGGTTTGCGTGTCGTGGAAGGTTCGGCGTTCGTCGCTGCACCGCTCGG

GGGGATGACTTTGGCACAGTTGGGAGCTGATGTGATTCGCTTTGATCCTATCGGCGGTGGACTGGATTAC

CGCAGATGGCCACTCACTCTTGATGGCCGCCATAGTTTGTTCTGGGCGGGGCTCAATAAGGGCAAAAGAT

CAATTGCTGTCGATCTGCGGTTGCCTCGCGGTCAAGAACTGTTGACGCAGCTCATCTGTGCGCCGGGTGA

TCATGCTGGACTGTTTTCTACCAACTTCCCCGCTAAGGGCTGGCTTGCTTACGAGGCCCTGCAAGCACAC

CGCCAGGATTTGATTATGGTCAATCTCACTGGTCGTCGGGATGGGGGCAGCGAAGTTGATTATACACTCA

ACCCTCAACTCGGGCTTCCACTGATGACAGGCCCGACGTCTAGCCCCGAGGTTGTGAATCATGTGTTTCC

AGCCTGGGATTTCATTTCTGGTCAAATGATCGCACTGGGACTCCTTGCTGCCGAAAGACACCGCAGACTC

ACGGGAGAGGGACAGCTTGTTCGTTTGGCCCTCAAGGATGTGGCTCTTGCCATGCTGGGTAACTTTGGAA

TGCTGGCAGAAGCGATGGTTAATGGGGCGGATCGTCCGCGGCAGGGTAACTACTTGTATGGGGCTTTTGG

CCGCGATTTCGGGACCCTTGATGGCCGTCGGCTGATGGTCGTTGGTTTGACGGGAATGCAGTGGCGCAGA

CTGGTGAAAGCTACCGGTTTGAGAGAACCCATTAGTGAGTTGGCAGCGCGTCTTGGACTGGATTTCGATG

ATGAAGGCAATCGCTATAGAGCCCGTCAGGAAATCGCACGGTTGTTTGAGCCTTGGTTCCATGCCCGCAC

CCTCGCAGAGGCTGCCTTGACTCTCGATGCCCACGGTGTCACATGGGGACCATACAGATCGGTGCGTGAA

GAGGTCGCAGCTGATCCTGATTGCTCCACTGATAACCCCATGTTTACCTTGACTGAACAACCTGGGATCG

GCCGCTATCTCATGCCGTCGACACCCCTTGATTTCGCAGGAGTTCCTAGACTGCCAGCAATGCCTGCTCC

AAGATTGGGAGAGCACACAGATCAGATTCTGTTGGATATCCTCGGACTCAGCGAGGCAGAAGTTGGGCGG

CTCCATGATGCGAGAGTGGTGGCAGGTCCGACATAAGgatctcttggaggaatccattaATGagcggaac aggacgactggcaggaaagattgcgttaattaccggtggcgccggcaatatcggcagtgaattgacacgt cgctttctcgcagagggagcgacggtcattattagtggacggaatcgggcgaagttgaccgcactggccg aacggatgcaggcagaggcaggagtgccggcaaagcgcatcgatctcgaagtcatggatgggagtgatcc ggtcgcggtacgtgccggtatcgaagcgattgtggcccgtcacggccagatcgacattctggtcaacaat gcaggaagtgccggtgcccagcgtcgtctggccgagattccactcactgaagctgaattaggccctggcg ccgaagagacgcttcatgccagcatcgccaatttacttggtatgggatggcatctgatgcgtattgcggc acctcatatgccggtaggaagtgcggtcatcaatgtctcgaccatcttttcacgggctgagtactacggg cggattccgtatgtcaccccctaaagctgctcttaatgctctatctcaacttgctgcgcgtgagttaggtg cacgtggcatccgcgttaatacgatctttcccggcccgattgaaagtgatcgcatccgtacagtgttcca gcgtatggatcagctcaagggcggcccgaaggcgacacagcgcaccatttttgaacaccatgcgattg tgtcgtgccaacgaccaggcgcgcttgaacgtcggttcccctccgtcggtgatgtggcagacgccgctg tctttctggccagtgccgaatccgccgctctctccggtgagacgattgaggttacgcacggaatggagtt gccggcctgcagtgagaccagcctgctggcccgtactgatctgcgcacgattgatgccagtggccgcacg acgctcatctgcgccggcgaccagattgaagaggtgatggcgctcaccggtatgttgcgtacctgtggga TABLE 4-continued

JIB-3345US(2013-020-03)

gtgaagtgatcatcggcttccgttcggctgcggcgctggcccagttcgagcaggcagtcaatgagagtcg gcggctggccggcgcagactttacgcctcccattgccttgccactcgatccacgcgatccggcaacaatt gacgctgtcttcgattgggggccggcgagaataccggcgggattcatgcagcggtgattctgcctgcta ccagtcacgaaccggcaccgtgcgtgattgaggttgatgatgagcgggtgctgaattttctggccgatga atcaccgggacaattgtgattgccagtcgcctggcccgttactggcagtcgcaacggcttaccccggc gcacgtgcgcgtgggccgcgtgtcattttctctcgaacggtgccgatcaaaatgggaatgtttacggac gcattcaaagtgccgctatcggtcagctcattcgtgtgtggcgtcacgaggctgaacttgactatcagcg tgccagcgccgccggtgatcatgtgctgccgccggtatgggccaatcagattgtgcgcttcgctaaccgc agccttgaagggttagaatttgcctgtgcctggacagctcaattgctccatagtcaacgccatatcaatg agattaccctcaacatccctgccaacattagcgccaccaccggcgcacgcagtgcatcggtcggatgggc ggaaagcctgatcgggttgcatttggggaaagttgccttgattaccggtggcagcgccggtattggtggg cagatcgggcgcctcctggctttgagtggcgcgcgcgtgatgctggcagcccgtgatcggcataagctcg aacagatgcaggcgatgatccaatctgagctggctgaggtgggtataccgatgtcgaagatcgcgtcca cattgcaccgggctgcgatgtgagtagcgaagcgcagcttgcggatcttgttgaacgtaccctgtcagct tttggcaccgtcgattatctgatcaacaacgccgggatcgccggtgtcgaagagatggttatcgatatgc cagttgagggatggcgccataccctcttcgccaatctgatcagcaactactcgttgatgcgcaaactggc gccgttgatgaaaaaacagggtagcggttacatccttaacgtctcatcatactttggcggtgaaaaagat gcggccattccctaccccaaccgtgccgattacgccgtctcgaaggctggtcagcgggcaatggccgaag tctttgcgcgcttccttggcccggagatacagatcaatgccattgcgccgggtccggtcgaaggtgatcg cttgcgcggtaccggtgaacgtcccggcctctttgcccgtcgggcgcggctgattttggagaacaagcgg ctgaatgagcttcacgctgctcttatcgcggctgcgcgcaccgatgagcgatctatgcacgaactggttg aactgctcttacccaatgatgtggccgcactagagcagaatcccgcagcacctaccgcgttgcgtgaact ggcacgacgttttcgcagcgaaggcgatccggcggcatcatcaagcagtgcgctgctgaaccgttcaatt gccgctaaattgctggctcgtttgcataatggtggctatgtgttgcctgccgacatctttgcaaacctgc caaacccgcccgatcccttcttcacccgagcccagattgatcgcgaggctcgcaaggttcgtgacggcat catgggatgctctacctgcaacggatgccgactgagtttgatgtcgcaatggccaccgtctattaccttt gccgaccgcaatgtcagtggtgagacattccacccatcaggtggtttgcgttacgaacgcacccctaccg gtggcgaactcttcggcttgccctcaccggaacggctggcggagctggtcggaagcacggtctatctgat aggtgaacatctgactgaacaccttaacctgcttgcccgtgcgtacctcgaacgttacggggcacgtcag gtagtgatgattgttgagacagaaaccggggcagagacaatgcgtcgcttgctccacgatcacgtcgagg ctggtcggctgatgactattgtggccggtgatcagatcgaagccgctatcgaccaggctatcactcgcta cggtcgcccagggccggtcgtctgtaccccccttccggccactgccgacggtaccactggtcgggcgtaaa gacagtgactggagcacagtgttgagtgaggctgaatttgccgagttgtgcgaacaccagctcacccacc atttccgggtagcgcgcaagattgccctgagtgatggtgccagtctcgcgctggtcactcccgaaactac ggctacctcaactaccgagcaatttgctctggctaacttcatcaaaacgacccttcacgcttttacggct acgattggtgtcgagagcgaaagaactgctcagcgcattctgatcaatcaagtcgatctgacccggcgtg cgcgtgccgaagagccgcgtgatccgcacgagcgtcaacaagaactggaacgttttatcgaggcagtctt gctggtcactgcaccactcccgcctgaagccgatacccgttacgccgggcggattcatcgcggacgggcg attaccgtgtaaGGATCTGTTTAGTGCGATCGCGGCAGGACTTAACTGAGCTTCAGAGAAGACGCAGGGA

TABLE 4-continued

JIB-3345US(2013-020-03)

```
CTTCATCCCAAGAAGCCACTGTCCGCAATTGGGCACGCCAGCCGTTGGCCCGCTGTTCTGGTGTCAGATT
GCGCTCAAAGGACTCATGGCAGTCGCGAGCCTGCTGCTCGTCGCAAGTCGCAATGCACGAGTAAAGAATG
CCCGCCGGGTCGAATTGTTCATTTACCCAAATCACTTTGTCGGTTGCCATAGGGGGTTGCTCCTACGCTC
AGCTGGATTTAGCGTCTTCTAATCCAGTGTAGACAGTAGTTTTGGCTCCGTTGAGCACTGTAGCCTTGGG
CGATCGCTCTAAACATTACATAAATTCACAAAGTTTTCGTTACATAAAAATAGTGTCTACTTAGCTAAAA
ATTAAGGGTTTTTTACACCTTTTTGACAGTTAATCTCCTAGCCTAAAAAGCAAGAGTTTTTAACTAAGAC
TCTTGCCCGGATCTcttggaggaatccattaatgcgcaagctagctcacaacttctacaaaccgttggcc
atcggtgctccggagccgatccgcgagctgccggttcgcccagagcgggtcgtccactttttccgcccc
acgtggaaaagattcgcgcccgtattcccgaagtcgccaaacaggttgatgtgctgtgcggcaatctgga
agacgcgattccgatggacgccaaagaggccgcccgcaacggctttatcgaggtagtcaaagcaaccgat
ttcggcgataccgcgctctgggtgcgggtcaatgcgctcaacagcccatgggtgctcgacgatattgccg
agattgtggccgcggtgggcaataaactcgatgtgattatgatcccgaaggtcgaggggccgtgggacat
tcacttcgttgatcagtatctggcgctgctcgaagcccgccaccagatcaaaaagccgattctgatccat
gctctgctagaaaccgcccagggcatggtcaatctggaagaaattgccggtgccagccccgcatgcacg
gcttcagtctgggcgctgatctcgccgcttcgcgtggcatgaagaccacccgtgtcggcggtgggca
cccttctacggcgtgctggccgacccgcaagaaggtcaggccgagcggccattctatcagcaagacctc
tggcactacacgattgcgcggatggttgatgtggcagttgcccatggcctgcgcgccttctacggcccct
tcggcgacatcaaggatgaagccgcctgcgaagcccaattccgcaacgccttcctcctcggctgcaccgg
tgcgtggtcgctcgcgcccaaccagattcccatcgccaagcgcgtcttcagcccggacgtgaacgaggtg
ctcttcgccaaacgcatcctggaggcgatgcccgatggttcgggggtggcgatgattgacggcaagatgc
aagacgatgcgacctggaagcaggcgaaggtgatcgttgatctggcgcggatgattgcgaagaaagaccc
cgacctggcccaggcgtatggtctgtgaGGATCTcttggaggaatccattaatgagcgctaaaaccaatc
ccggcaacttcttcgaggattttcggcttggtcagacgattgtccacgccacgccgcgcacgattaccga
aggcgacgttgccctctacacgtcgctgtacggttcccgctttgcgcttacctcatcaaccccctttgcg
caatcgttggggctggagcgagcgccgattgatagcctgctggtgtttcatatcgtcttcggtaagacgg
tacccgacatctcgctcaacgcgattgccaatctcggctacgccggtggacgctttggcgcagtggtcta
ccccggcgacacccttttccaccacttcaaaggtgatcggtttgcgccagaacaaagacggcaaaaccggt
gtggtgtatgtccactcggtggggtgaaccaatgggacgaggtcgtgctcgaatacatccgctgggtga
tggtgcggaagcgcgacccgaacgcaccggcaccggagacggttgtccccgacctgcccgactcggtacc
ggtcaccgatttgaccgtcccgtacaccgtatcggcggcgaactacaatctggcccacgccggcagcaac
tacctctgggacgattacgaggtgggtgagaagatcgatcacgtggacggggtcacgattgaggaggccg
agcacatgcaggcgacccggctctaccagaacacagcgcgggtccacttcaacctccacgttgagcggga
agggcggtttggccggcggatcgtgtacggcggccacatcatcagcctggcgcgttcgttgtcgttcaac
gggctggccaatgcgctgagcattgcggccatcaacagcgggcgccacaccaaccccagctttgccggcg
acacgatctacgcctggtcagagattcttgccaagatggcgattccgggccgcaccgatattggcgcctt
gcgggtacgtaccgtcgccaccaaagatcgcccgtgtcacgattttccctaccgtgacgcggaggggaac
tacgatccggcggtggtgcttgattttgattacacagtattgatgccgcgtcggggatgaGGATCtctca
acaGGCCTGCtggtaatcGCAGGCCttttttttttGGATCTGTTTAGTGCGATCGCGGCAGGACTTAACTG
AGCTTCAGAGAAGACGCAGGGACTTCATCCCAAGAAGCCACTGTCCGCAATTGGGCACGCCAGCCGTTGG
```

TABLE 4-continued

JIB-3345US(2013-020-03)

CCCGCTGTTCTGGTGTCAGATTGCGCTCAAAGGACTCATGGCAGTCGCGAGCCTGCTGCTCGTCGCAAGT
CGCAATGCACGAGTAAAGAATGCCCGCCGGGTCGAATTGTTCATTTACCCAAATCACTTTGTCGGTTGCC
ATAGGGGGTTGCTCCTACGCTCAGCTGGATTTAGCGTCTTCTAATCCAGTGTAGACAGTAGTTTTGGCTC
CGTTGAGCACTGTAGCCTTGGGCGATCGCTCTAAACATTACATAAATTCACAAAGTTTTCGTTACATAAA
AATAGTGTCTACTTAGCTAAAAATTAAGGGTTTTTTACACCTTTTTGACAGTTAATCTCCTAGCCTAAAA
AGCAAGAGTTTTTAACTAAGACTCTTGCCCGGATCTcttggaggaatccattaatgaagggtattctcca
cggattgcgtgtagtggagggatcggcctttgttgccgcaccgctgggggggcatgacgctcgcgcagttg
ggggccgatgtgattcgcttcgaccctatcggcggcggtctcgattataaacgctggccggttacgctcg
acggtaagcatagtctgttttgggccggtctcaacaagggcaaacgttcgattgcgattgatattcgcca
tccacgcgggcaggagttgctgacgcagcttatctgcgcacccggcgagcatgccggtctctttattacc
aattttccggcgcgcggttggttgagttacgatgagctgaagcgtcaccgcgccgacctgattatggtca
atctggtcgggcggcgcgatggcgggtcagaggtggattacaccgttaacccgcagttggggctgccgtt
tatgaccggcccggtcacgacgcctgatgtggttaatcacgtgctgccggcctgggatattgtgaccggg
cagatgattgcgctcggtctgctggctgccgagcgtcaccgtcggctgaccggtgaggggcaactggtga
agattgcgctgaaggatgtcgggctggcgatgatcggccatctggggatgattgccgaggtgatgatcaa
cgataccgaccgtccacggcaggggaattatctctacggggcgttcgggcgcgatttcgagaccctcgat
gggaagcgggtgatggtggttggtttgaccgatttgcagtggaaggcgctgggcaaggcgaccggtctga
cggatgcgttcaatgcgctcggtgcgcggctggggctgaatatggacgaggaaggcgaccgcttccgtgc
ccgccacgagatcgctgcgctgcttgaaccctggttccacgcccgcacgctggccgaggtacgacgcatc
tttgaacagcaccgcgtcacctgggcgccgtaccgcacggtacgggaagcgattgcccaggaccccgact
gctccaccgataacccgatgtttgcgatggtcgagcagcccggcattgggagctacctgatgccgggttc
gccgctggatttcactgccgtcccgcgtctgcctgtccagcctgcgccccggctcggcgagcacaccgat
gagattttgctggaggtgctgggcttgagtgaagctgaagtcggtcgcttgcacgatgaagggattgtgg
ccgggccagatcgggcagcgtagGGATCTcttggaggaatccattaatgagcagcgcggattggatggcc
tggattgggcgtactgagcaggtggaagatgatatttgtctggcccaggcgattgccgcagccgcaacgc
ttgagccgccgtcgggagcaccaactgcggatagtccgctccctccgctctggcactggttttactttct
gccccgtgccccacagtcgcagctcagcagtgatggtcatccgcagcgcggcggctttatcccaccgata
ccctatccacgccgcatgtttgccggtgcccgcatccgctttcatcaccccgctgcgcatcggccaaccgg
cgcgtcgtgaaggtgtgatccgcaacatcactcaaaaaagcggtcgcagcgggccgctggcatttgtgac
ggtcggctaccagatataccaacatgagtgctttgtatcgaagaagagcaagacatcgtgtaccgtgag
ccgggggcaccggtgccggcccccacaccggtagagttaccaccggtacacgatgcaatcacccgtactg
ttgtgcccgatccgcgtctgctctttcgcttctcagccctcaccttcaatgcgcatcggattcactacga
ccggccatacgctcagcacgaagagggctatccgggcctggtcgtgcatggcccctggtagcagtcctg
ctaatggaactggcccgtcaccatacatcccgcccgattgttggcttttcgttccgcagccaggcgccac
tcttcgatctggccccttccgcctgctggccgccccaacggcgaccgcatcgatctggaagcacaggg
acctgacggggcaacggcgctcagcgcgacggttgagttgggggggatgaGGATCTctcaacaGGCCTGCt
ggtaatcGCAGGCCtttttttttG TABLE 4-continued

JIB-3345US(2013-020-03)

>PMS4749                                                           SEQ ID NO: 33
GATCTatgaagggtattctccacggattgcgtgtagtggagggatcggcctttgttgccgcaccgctggg gggcatgacgctcgcgcagttgggggccgatgtgattcgcttcgaccctatcggcggcggtctcgattat aaacgctggccggttacgctcgacggtaagcatagtctgttttgggccggtctcaacaagggcaaacgtt cgattgcgattgatattcgccatccacgcgggcaggagttgctgacgcagcttatctgcgcacccggcga gcatgccggtctctctttattaccaattttccggcgcgcggttggttgagttacgatgagctgaagcgtcac cgcgccgacctgattatggtcaatctggtcgggcggcgcgatggcgggtcagaggtggattacaccgtta acccgcagttggggctgccgtttatgaccggcccggtcacgacgcctgatgtggttaatcacgtgctgcc ggcctgggatattgtgaccgggcagatgattgcgctcggtctgctggctgccgagcgtcaccgtcggctg accggtgaggggcaactggtgaagattgcgctgaaggatgtcgggctggcgatgatcggccatctgggga tgattgccgaggtgatgatcaacgataccgaccgtccacggcagggaattatctctacggggcgttcgg gcgcgatttcgagaccctcgatgggaagcgggtgatggtggttggtttgaccgatttgcagtggaaggcg ctgggcaaggcgaccggtctgacggatgcgttcaatgcgctcggtgcgcggctggggctgaatatggacg aggaaggcgaccgcttccgtgcccgccacgagatcgctgcgctgcttgaaccctggttccacgcccgcac gctggccgaggtacgacgcatctttgaacagcaccgcgtcacctgggcgccgtaccgcacggtacgggaa gcgattgcccaggaccccgactgctccaccgataacccgatgtttgcgatggtcgagcagcccggcattg ggagctacctgatgccgggttcgccgctggatttcactgccgtcccgcgtctgcctgtccagcctgcgcc ccggctcggcgagcacaccgatgagattttgctggaggtgctgggcttgagtgaagctgaagtcggtcgc ttgcacgatgaagggattgtggccgggccagatcgggcagctagGgatctcttggaggaatccattaAT Gagcggaacaggacgactggcaggaaagattgcgttaattaccggtggcgccggcaatatcggcagtgaa ttgacacgtcgctttctcgcagagggagcgacggtcattattagtggacggaatcgggcgaagttgaccg cactggccgaacggatgcaggcagaggcaggagtgccggcaaagcgcatcgatctcgaagtcatggatgg gagtgatccggtcgcggtacgtgccggtatcgaagcgattgtggcccgtcacggccagatcgacattctg gtcaacaatgcaggaagtgccggtgcccagcgtcgtctggccgagattccactcactgaagctgaattag gccctggcgccgaagagacgcttcatgccagcatcgccaatttacttggtatgggatggcatctgatgcg tattgcggcacctcatatgccggtaggaagtgcggtcatcaatgtctcgaccatcttttcacgggctgag tactacgggcggattccgtatgtcacccctaaagctgctcttaatgctctatctcaacttgctgcgcgtg agttaggtgcacgtggcatccgcgttaatacgatctttcccggcccgattgaaagtgatcgcatccgtac agtgttccagcgtatggatcagctcaaggggcggcccgaaggcgacacagcgcaccattttttgaacacc atgcgattgtgtcgtgccaacgaccagggcgcgcttgaacgtcggttccctccgtcggtgatgtggcag acgccgctgtctttctggccagtgccgaatccgccgctctctccggtgagacgattgaggttacgcacgg aatggagttgccggcctgcagtgagaccagcctgctggcccgtactgatctgcgcacgattgatgccagt ggccgcacgacgctcatctgcgccggcgaccagattgaagaggtgatggcgctcaccggtatgttgcgta cctgtgggagtgaagtgatcatcggcttccgttcggctgcggcgctggcccagttcgagcaggcagtcaa tgagagtcggcggctggccggcgcagactttacgcctcccattgccttgccactcgatccacgcgatccg gcaacaattgacgctgtcttcgattgggggccggcgagaataccggcgggattcatgcagcggtgattc tgcctgctaccagtcacgaaccggcaccgtgcgtgattgaggttgatgatgagcgggtgctgaatttttct ggccgatgaaatcaccgggacaattgtgattgccagtcgcctggcccgttactggcagtcgcaacggctt accccggcgcacgtgcgcgtgggccgcgtgtcattttttctctcgaacggtgccgatcaaaatgggaatg TABLE 4-continued

JIB-3345US(2013-020-03)

tttacggacgcattcaaagtgccgctatcggtcagctcattcgtgtgtggcgtcacgaggctgaacttga
ctatcagcgtgccagcgccgccggtgatcatgtgctgccgccggtatgggccaatcagattgtgcgcttc
gctaaccgcagccttgaagggttagaatttgcctgtgcctggacagctcaattgctccatagtcaacgcc
atatcaatgagattaccctcaacatccctgccaacattagcgccaccaccggcgcacgcagtgcatcggt
cggatgggcggaaagcctgatcgggttgcatttggggaaagttgccttgattaccggtggcagcgccggt
attggtgggcagatcgggcgcctcctggctttgagtggcgcgcgcgtgatgctggcagcccgtgatcggc
ataagctcgaacagatgcaggcgatgatccaatctgagctggctgaggtggggtataccgatgtcgaaga
tcgcgtccacattgcaccgggctgcgatgtgagtagcgaagcgcagcttgcggatcttgttgaacgtacc
ctgtcagcttttggcaccgtcgattatctgatcaacaacgccgggatcgccggtgtcgaagagatggtta
tcgatatgccagttgagggatggcgccataccctcttcgccaatctgatcagcaactactcgttgatgcg
caaactggcgccgttgatgaaaaaacagggtagcggttacatccttaacgtctcatcatactttggcggt
gaaaaagatgcggccattccctaccccaaccgtgccgattacgccgtctcgaaggctggtcagcgggcaa
tggccgaagtctttgcgcgcttccttggcccggagatacagatcaatgccattgcgccgggtccggtcga
aggtgatcgcttgcgcggtaccggtgaacgtcccggcctctttgcccgtcgggcgcggctgattttggag
aacaagcggctgaatgagcttcacgctgctcttatcgcggctgcgcgcaccgatgagcgatctatgcacg
aactggttgaactgctcttacccaatgatgtggccgcactagagcagaatcccgcagcacctaccgcgtt
gcgtgaactggcacgacgttttcgcagcgaaggcgatccggcggcatcatcaagcagtgcgctgctgaac
cgttcaattgccgctaaattgctggctcgtttgcataatggtggctatgtgttgcctgccgacatctttg
caaacctgccaaacccgccgatcccttcttcacccgagcccagattgatcgcgaggctcgcaaggttcg
tgacggcatcatggggatgctctacctgcaacggatgccgactgagtttgatgtcgcaatggccaccgtc
tattaccttgccgaccgcaatgtcagtggtgagacattccacccatcaggtggtttgcgttacgaacgca
cccctaccggtggcgaactcttcggcttgccctcaccggaacggctggcggagctggtcggaagcacggt
ctatctgataggtgaacatctgactgaacaccttaacctgcttgcccgtgcgtacctcgaacgttacggg
gcacgtcaggtagtgatgattgttgagacagaaaccggggcagagacaatgcgtcgcttgctccacgatc
acgtcgaggctggtcggctgatgactattgtggccggtgatcagatcgaagccgctatcgaccaggctat
cactcgctacggtcgcccagggccggtcgtctgtaccccttccggccactgccgacggtaccactggtc
gggcgtaaagacagtgactggagcacagtgttgagtgaggctgaatttgccgagttgtgcgaacaccagc
tcacccaccatttccgggtagcgcgcaagattgccctgagtgatggtgccagtctcgcgctggtcactcc
cgaaactacggctacctcaactaccgagcaatttgctctggctaacttcatcaaaacgacccttcacgct
tttacggctacgattggtgtcgagagcgaaagaactgctcagcgcattctgatcaatcaagtcgatctga
cccggcgtgcgcgtgccgaagagccgcgtgatccgcacgagcgtcaacaagaactggaacgttttatcga
ggcagtcttgctggtcactgcaccactcccgcctgaagccgatacccgttacgccgggcggattcatcgc
ggacgggcgattaccgtgtaaGGATCTGTTTAGTGCGATCGCGGCAGGACTTAACTGAGCTTCAGAGAAG
ACGCAGGGACTTCATCCCAAGAAGCCACTGTCCGCAATTGGGCACGCCAGCCGTTGGCCCGCTGTTCTGG
TGTCAGATTGCGCTCAAAGGACTCATGGCAGTCGCGAGCCTGCTGCTCGTCGCAAGTCGCAATGCACGAG
TAAAGAATGCCCGCCGGGTCGAATTGTTCATTTACCCAAATCACTTTGTCGGTTGCCATAGGGGGTTGCT
CCTACGCTCAGCTGGATTTAGCGTCTTCTAATCCAGTGTAGACAGTAGTTTTGGCTCCGTTGAGCACTGT
AGCCTTGGGCGATCGCTCTAAACATTACATAAATTCACAAAGTTTTCGTTACATAAAAATAGTGTCTACT
TAGCTAAAAATTAAGGGTTTTTTACACCTTTTTGACAGTTAATCTCCTAGCCTAAAAAGCAAGAGTTTTT TABLE 4-continued

JIB-3345US(2013-020-03)

AACTAAGACTCTTGCCCGGATCTcttggaggaatccattaatgcgcaagctagctcacaacttctacaaa
ccgttggccatcggtgctccggagccgatccgcgagctgccggttcgcccagagcgggtcgtccacttttt
ttccgccccacgtggaaaagattcgcgcccgtattcccgaagtcgccaaacaggttgatgtgctgtgcgg
caatctggaagacgcgattccgatggacgccaaagaggccgcccgcaacggctttatcgaggtagtcaaa
gcaaccgatttcggcgataccgcgctctgggtgcgggtcaatgcgctcaacagcccatgggtgctcgacg
atattgccgagattgtggccgcggtgggcaataaactcgatgtgattatgatcccgaaggtcgaggggcc
gtgggacattcacttcgttgatcagtatctggcgctgctcgaagcccgccaccagatcaaaaagccgatt
ctgatccatgctctgctagaaaccgcccagggcatggtcaatctggaagaaattgccggtgccagccccc
gcatgcacggcttcagtctggggccggctgatctcgccgcttcgcgtggcatgaagaccaccgtgtcgg
cggtgggcacccttctacggcgtgctggccgacccgcaagaaggtcaggccgagcggccattctatcag
caagacctctggcactacacgattgcgcggatggttgatgtggcagttgcccatggcctgcgcgccttct
acggccccttcggcgacatcaaggatgaagccgcctgcgaagcccaattccgcaacgccttcctcctcgg
ctgcaccggtgcgtggtcgctcgcgcccaaccagattcccatcgccaagcgcgtcttcagcccggacgtg
aacgaggtgctcttcgccaaacgcatcctggaggcgatgcccgatggttcgggggtggcgatgattgacg
gcaagatgcaagacgatgcgacctggaagcaggcgaaggtgatcgttgatctggcgcggatgattgcgaa
gaaagaccccgacctggcccaggcgtatggtctgtgaGGATCTcttggaggaatccattaatgagcgcta
aaaccaatcccggcaacttcttcgaggattttcggcttggtcagacgattgtccacgccacgccgcgcac
gattaccgaaggcgacgttgccctctacacgtcgctgtacggttcccgctttgcgcttacctcatcaacc
cccttttgcgcaatcgttggggctggagcgagcgccgattgatagcctgctggtgtttcatatcgtcttcg
gtaagacggtacccgacatctcgctcaacgcgattgccaatctcggctacgccggtggacgctttggcgc
agtggtctaccccggcgacacccttttccaccacttcaaaggtgatcggtttgcgccagaacaaagacggc
aaaaccggtgtggtgtatgtccactcggtgggggtgaaccaatgggacgaggtcgtgctcgaatacatcc
gctgggtgatggtgcggaagcgcgacccgaacgcaccggcaccggagacggttgtccccgacctgcccga
ctcggtaccggtcaccgatttgaccgtcccgtacaccgtatcggcggcgaactacaatctggcccacgcc
ggcagcaactacctctgggacgattacgaggtgggtgagaagatcgatcacgtggacggggtcacgattg
aggaggccgagcacatgcaggcgacccggctctaccagaacacagcgcgggtccacttcaacctccacgt
tgagcgggaagggcggtttggccggcggatcgtgtacggcggccacatcatcagcctggcgcgttcgttg
tcgttcaacgggctggccaatgcgctgagcattgcggccatcaacagcgggcgccacaccaaccccagct
ttgccggcgacacgatctacgcctggtcagagattcttgccaagatggcgattccgggccgcaccgatat
tggcgccttgcgggtacgtaccgtcgccaccaaagatcgcccgtgtcacgattttccctaccgtgacgcg
gaggggaactacgatccggcggtggtgcttgattttgattacacagtattgatgccgcgtcggggatgaG
GATCTctcaacaGGCCTGCtggtaatcGCAGGCCttttttttttGGATCTGTTTAGTGCGATCGCGGCAGG
ACTTAACTGAGCTTCAGAGAAGACGCAGGGACTTCATCCCAAGAAGCCACTGTCCGCAATTGGGCACGCC
AGCCGTTGGCCCGCTGTTCTGGTGTCAGATTGCGCTCAAAGGACTCATGGCAGTCGCGAGCCTGCTGCTC
GTCGCAAGTCGCAATGCACGAGTAAAGAATGCCCGCCGGGTCGAATTGTTCATTTACCCAAATCACTTTG
TCGGTTGCCATAGGGGGTTGCTCCTACGCTCAGCTGGATTTAGCGTCTTCTAATCCAGTGTAGACAGTAG
TTTTGGCTCCGTTGAGCACTGTAGCCTTGGGCGATCGCTCTAAACATTACATAAATTCACAAAGTTTTCG
TTACATAAAAATAGTGTCTACTTAGCTAAAAATTAAGGGTTTTTTACACCTTTTTGACAGTTAATCTCCT
AGCCTAAAAAGCAAGAGTTTTTAACTAAGACTCTTGCCCGGATCTcttggaggaatccattaatgaaggg TABLE 4-continued

JIB-3345US(2013-020-03)

tattctccacggattgcgtgtagtggagggatcggcctttgttgccgcaccgctgggggcatgacgctc gcgcagttgggggccgatgtgattcgcttcgaccctatcggcggcggtctcgattataaacgctggccgg ttacgctcgacggtaagcatagtctgttttgggccggtctcaacaagggcaaacgttcgattgcgattga tattcgccatccacgcgggcaggagttgctgacgcagcttatctgcgcaccggcgagcatgccggtctc tttattaccaattttccggcgcgcggttggttgagttacgatgagctgaagcgtcaccgcgccgacctga ttatggtcaatctggtcggcggcgcgatggcgggtcagaggtggattacaccgttaacccgcagttggg gctgccgtttatgaccggcccggtcacgacgcctgatgtggttaatcacgtgctgccggcctgggatatt gtgaccgggcagatgattgcgctcggtctgctggctgccgagcgtcaccgtcggctgaccggtgaggggc aactggtgaagattgcgctgaaggatgtcgggctggcgatgatcggccatctggggatgattgccgaggt gatgatcaacgataccgaccgtccacggcaggggaattatctctacggggcgttcgggcgcgatttcgag accctcgatgggaagcgggtgatggtggttggtttgaccgatttgcagtggaaggcgctgggcaaggcga ccggtctgacggatgcgttcaatgcgctcggtgcgcggctggggctgaatatggacgaggaaggcgaccg cttccgtgcccgccacgagatcgctgcgctgcttgaaccctggttccacgcccgcacgctggccgaggta cgacgcatctttgaacagcaccgcgtcacctgggcgccgtaccgcacggtacgggaagcgattgcccagg accccgactgctccaccgataaacccgatgtttgcgatggtcgagcagcccggcattgggagctacctgat gccgggttcgccgctggatttcactgccgtcccgcgtctgcctgtccagcctgcgccccggctcggcgag cacaccgatgagattttgctggaggtgctgggcttgagtgaagctgaagtcggtcgcttgcacgatgaag ggattgtggccgggccagatcgggcagcgtagGGATCTcttggaggaatccattaatgagcagcgcggat tggatggcctggattgggcgtactgagcaggtggaagatgatatttgtctggcccaggcgattgccgcag ccgcaacgcttgagccgccgtcgggagcaccaactgcggatagtccgctccctccgctctggcactggtt ttactttctgccccgtgccccacagtcgcagctcagcagtgatggtcatccgcagcgcggcggctttatc ccaccgatacctatccacgccgcatgtttgccggtgcccgcatccgctttcatcacccgctgcgcatcg gccaaccggcgcgtcgtgaaggtgtgatccgcaacatcactcaaaaaagcggtcgcagcgggccgctggc atttgtgacggtcggctaccagatataccaacatgagatgctttgtatcgaagaagagcaagacatcgtg taccgtgagccgggggcaccggtgccggccccacaccggtagagttaccaccggtacacgatgcaatca cccgtactgttgtgcccgatccgcgtctgctctttcgcttctcagccctcaccttcaatgcgcatcggat tcactacgaccggccatacgctcagcacgaagagggctatccgggcctggtcgtgcatggccccctggta gcagtcctgctaatggaactggcccgtcaccatacatcccgcccgattgttggcttttcgttccgcagcc aggcgccactcttcgatctggccccttccgcctgctggcccgcccaacggcgaccgcatcgatctgga agcacagggacctgacggggcaacggcgctcagcgcgacggttgagttggggggatgaGGATCTctcaac aGGCCTGCtggtaatcGCAGGCCttttttttttG

>PCS

SEQ ID NO: 34

GATCTcttggaggaatccattaatgatcgacactgcgccccttgccccaccacgggcgccccgctctaat ccgattcgggatcgagttgattgggaagctcagcgcgctgctgcgctggcagatcccggtgcctttcatg gcgcgattgcccggacagttatccactggtacgacccacaacaccattgctggattcgcttcaacgagtc tagtcagcgtttgggaagggctggatgccgctaccggtgcccctgtaacggtagactatcccgccgattat cagccctggcaacaggcgtttgatgatagtgaagcgccgttttaccgctggtttagtggtgggttgacaa atgcctgctttaatgaagtagaccggcatgtcacgatgggctatggcgacgaggtggcctactactttga aggtgaccgctgggataactcgctcaacaatggtcgtggtggtccggttgtccaggagacaatcacgcgg TABLE 4-continued

JIB-3345US(2013-020-03)

cggcgcctgttggtggaggtggtgaaggctgcgcaggtgttgcgtgatctgggcctgaagaagggtgatc ggattgctctgaatatgccgaatattatgccgcagatttattatacggaagcggcaaaacgactgggtat tctgtacacgccggtcttcggtggcttctcggacaagactctttccgaccgtattcacaatgccggtgca cgagtggtgattacctctgatggtgcgtaccgcaacgcgcaggtggtgccctacaaagaagcgtataccg atcaggcgctcgataagtatattccggttgagacggcgcaggcgattgttgcgcagaccctggccacctt gcccctgactgagtcgcagcgccagacgatcatcaccgaagtggaggccgcactggccggtgagattacg gttgagcgctcggacgtgatgcgtggggttggttctgccctcgcaaagctccgcgatcttgatgcaagcg tgcaggcaaaggtgcgtacagtactggcgcaggcgctggtcgagtcgccgccgcgggttgaagctgtggt ggttgtgcgtcataccggtcaggagattttgtggaacgaggggcgagatcgctggagtcacgacttgctg gatgctgcgctggcgaagattctggccaatgcgcgtgctgccggctttgatgtgcacagtgagaatgatc tgctcaatctccccgatgaccagcttatccgtgcgctctacgccagtattccctgtgaaccggttgatgc tgaatatccgatgtttatcatttacacatcgggtagcaccggtaagcccaagggtgtgatccacgttcac ggcggttatgtcgccggtgtggtgcacaccttgcgggtcagttttgacgccgagccgggtgatacgatat atgtgatcgccgatccgggctggatcaccggtcagagctatatgctcacagccacaatggccggtcggct gaccggggtgattgccgagggatcaccgctcttcccctcagccgggcgttatgccagcatcatcgagcgc tatggggtgcagatctttaaggcgggtgtgaccttcctcaagacagtgatgtccaatccgcagaatgttg aagatgtgcgactctatgatatgcactcgctgcgggttgcaaccttctgcgccgagccggtcagtccggc ggtgcagcagtttggtatgcagatcatgaccccgcagtatatcaattcgtactgggcgaccgagcacggt ggaattgtctggacgcatttctacggtaatcaggacttcccgcttcgtcccgatgcccatacctatccct tgccctgggtgatgggtgatgtctgggtggccgaaactgatgagagcgggacgacgcgctatcgggtcgc tgatttcgatgagaagggcgagattgtgattaccgcccgtatccctacctgacccgcacactctgggt gatgtgcccggtttcgaggcgtacctgcgcggtgagattccgctgcgggcctggaagggtgatgccgagc gtttcgtcaagacctactggcgacgtgggccaaacggtgaatggggctatatccagggtgattttgccat caagtaccccgatggtagcttcacgctccacggacgctctgacgatgtgatcaatgtgtcgggccaccgt atgggcaccgaggagattgagggtgccattttgcgtgaccgccagatcacgcccgactcgcccgtcggta attgtattgtggtcggtgcgccgcaccgtgagaagggtctgaccccggttgccttcattcaacctgcgcc tggccgtcatctgaccggcgccgaccggcgccgtctcgatgagctggtgcgtaccgagaaggggcggtc agtgtcccagaggattacatcgaggtcagtgcctttcccgaaacccgcagcgggaagtatatgcggcgct ttttgcgcaatatgatgctcgatgaaccactgggtgatacgacgacgttgcgcaatcctgaagtgctcga agagattgcagccaagatcgctgagtggaaacgccgtcagcgtatggccgaagagcagcagatcatcgaa cgctatcgctacttccggatcgagtatcacccaccaacggccagtgcgggtaaactcgcggtagtgacgg tgacaaatccgccggtgaacgcactgaatgagcgtgcgctcgatgagttgaacacaattgttgaccacct ggcccgtcgtcaggatgttgccgcaattgtcttcaccggacagggcgccaggagttttgtcgccggcgct gatattcgccagttgctcgaagagattcatacggttgaagaggcaatggccctgccgaataacgccatc ttgctttccgcaagattgagcgtatgaataagccgtgtatcgcggcgatcaacggtgtggcgctcggtgg tggtctggaattcgccatggcctgccattaccgggttgccgatgtctatgccgaattcggtcagccagag attaatctgcgcttgctacctggttatggtggcacgcagcgcttgccgcgcctgttgtacaagcgcaaca acggcaccggtctgctccgagcgctggagatgattctgggtgggcgtagcgtaccggctgatgaggcgct ggagctgggtctgatcgatgccattgctaccggcgatcaggactcactgtcgctggcatgcgcgttagcc TABLE 4-continued

JIB-3345US(2013-020-03)

cgtgccgcaatcggcgccgatggtcagttgatcgagtcggctgcggtgacccaggctttccgccatcgcc
acgagcagcttgacgagtggcgcaaaccagacccgcgctttgccgatgacgaactgcgctcgattatcgc
ccatccacgtatcgagcggattatccggcaggcccataccgttgggcgcgatgcggcagtgcatcgggca
ctggatgcaatccgctatggcattatccacggcttcgaggccggtctggagcacgaggcgaagctctttg
ccgaggcagtggttgacccgaacggtggcaagcgtggtattcgcgagttcctcgaccgccagagtgcgcc
gttgccaacccgccgaccattgattacacctgaacaggagcaactcttgcgcgatcagaaagaactgttg
ccggttggttcacccttcttccccggtgttgaccggattccgaagtggcagtacgcgcaggcggttattc
gtgatccggacaccggtgcggcggctcacggcgatcccatcgtggctgaaaagcagattattgtgccggt
ggaacgcccccgcgccaatcaggcgctgatctatgttctggcctcggaggtgaacttcaacgatatctgg
gcgattaccggtattccggtgtcacggtttgatgagcacgaccgcgactggcacgttaccggttcaggtg
gcatcggcctgatcgttgcgctgggtgaagaggcgcgacgcgaaggccggctgaaggtgggtgatctggt
ggcgatctactccgggcagtcggatctgctctcaccgctgatgggccttgatccgatggccgccgatttc
gtcatccaggggaacgacacgccagatggatcgcatcagcaatttatgctggcccaggccccgcagtgtc
tgcccatcccaaccgatatgtctatcgaggcagccggcagctacatcctcaatctcggtacgatctatcg
cgccctctttacgacgttgcaaatcaaggccggacgcaccatctttatcgagggtgcggcgaccggtacc
ggtctggacgcagcgcgctcggcggcccggaatggtctgcgcgtaattggaatggtcagttcgtcgtcac
gtgcgtctacgctgctggctgcgggtgcccacggtgcgattaaccgtaaagacccggaggttgccgattg
tttcacgcgcgtgcccgaagatccatcagcctgggcagcctgggaagccgccggtcagccgttgctggcg
atgttccgggcgcagaacgacgggcgactggccgattatgtggtctcgcacgcgggcgagacggccttcc
cgcgcagtttccagcttctcggcgagccacgcgatggtcacattccgacgctcacattctacggtgccac
cagtggctaccacttcaccttcctgggtaagccagggtcagcttcgccgaccgagatgctgcggcgggcc
aatctccgcgccggtgaggcggtgttgatctactacggggttgggagcgatgacctggtagataccggcg
gtctggaggctatcgaggcggcgcggcaaatgggagcgcggatcgtcgtcgttaccgtcagcgatgcgca
acgcgagtttgtcctctcgttgggcttcggggctgccctacgtggtgtcgtcagcctggcggaactcaaa
cggcgcttcggcgatgagtttgagtggccgcgcacgatgccgccgttgccgaacgcccgccaggacccgc
agggtctgaaagaggctgtccgccgcttcaacgatctggtcttcaagccgctaggaagcgcggtcggtgt
cttcttgcggagtgccgacaatccgcgtggctaccccgatctgatcatcgagcgggctgcccacgatgca
ctggcggtgagcgcgatgctgatcaagcccttcaccggacggattgtctacttcgaggacattggtgggc
ggcgttactccttcttcgcaccgcaaatctgggtgcgccagcgccgcatctacatgccgacggcacagat
ctttggtacgcacctctcaaatgcgtatgaaattctgcgtctgaatgatgagatcagcgccggtctgctg
acgattaccgagccggcagtggtgccgtgggatgaactacccgaagcacatcaggcgatgtgggaaaatc
gccacacggcggccacttatgtggtgaatcatgccttaccacgtctcggcctaaagaacagggacgagct
gtacgaggcgtggacggccggcgagcggtagG >pAM1573PMS

SEQ ID NO: 35 gatccgggagtttgtagaaacgcaaaaaggccatccgtcaggatggccttctgcttaatttgatgcctgg
cagtttatggcgggcgtcctgcccgccaccctccgggccgttgcttcgcaacgttcaaatccgctcccgg
cggatttgtcctactcaggagagcgttcaccgacaaacaacagataaaacgaaaggcccagtctttcgac
tgagcctttcgttttatttgatgcctggcagttccctactctcgcatggggagaccccacactaccatcg
gcgctacggcgtttcacttctgagttcggcatggggtcaggtgggaccaccgcgctactgccgccaggca TABLE 4-continued

JIB-3345US(2013-020-03)

aattctgttttattgagccgttaccccacctactagctaatcccatctgggcacatccgatggcaagagg
cccgaaggtcccctctttggtcttgcgacgttatgcggtattagctaccgtttccagtagttatccccc
tccatcaggcagtttcccagacattactcacccgtccgccactcgtcagcaaagaagcaagcttagatcc
gtcacacgggataataccgcgccacatagcagaactttaaaagtgctcatcattggaaaacgttcttcgg
ggcgaaaactctcaaggatcttaccgctgttgagatccagttcgatgtaacccactcgtgcacccaactg
atcttcagcatcttttactttcaccagcgtttctgggtgagcaaaaacaggaaggcaaaatgccgcaaaa
aagggaataagggcgacacggaaatgttgaatactcatactcttccttttcaatattattgaagcattt
atcagggttattgtctcatgagcggatacatatttgaatgtatttagaaaaataaacaaatagggttcc
gcgcacatttccccgaaaagtgccacctgacgtctaagaaaccattattatcatgacattaacctataaa
ataggcgtatcacgaggccctttcgtcttcgaataaatacctgtgacggaagatcacttcgcagaataa
ataaatcctggtgtccctgttgataccgggaagccctgggccaacttttggcgaaaatgagacgttgatc
ggcacgtaagaggttccaacttttcaccataatgaaataagatcactaccgggcgtattttttgagttatc
gagattttcaggagctaaggaagctaaaatggagaaaaaaatcactggatataccaccgttgatatatcc
caatggcatcgtaaagaacattttgaggcatttcagtcagttgctcaatgtacctataaccagaccgttc
agctggatattacggcctttttaaagaccgtaaagaaaaataagcacaagttttatccgcctttattca
cattcttgcccgcctgatgaatgctcatccggaGttccgtatggcaatgaaagacggtgagctggtgata
tgggatagtgttcacccttgttacaccgttttccatgagcaaactgaaacgttttcatcgctctggagtg
aataccacgacgatttccggcagtttctacacatatattcgcaagatgtggcgtgttacggtgaaaacct
ggcctatttccctaaagggtttattgagaatatgttttcgtctcagccaatccctgggtgagtttcacc
agttttgatttaaacgtggccaatatggacaacttcttcgccccgttttcaccatgggcaaatattata
cgcaaggcgacaaggtgctgatgccgctggcgattcaggttcatcatgccgtttgtgatggcttccatgt
cggcagaatgcttaatgaattacaacagtactgcgatgagtggcagggcggggcgtaattttttttaaggc
agttattggtgcccttaaacgcctggtgctacgcctgaataagtgataataagcggatgaatggcagaaa
ttcgaaagcaaattcgacccggtcgtcggttcagggcagggtcgttaaatagccgcttatgtctattgct
ggtttaccggtttattgactaccggaagcagtgtgaccgtgtgcttctcaaatgcctgaggccagtttgc
tcaggctctccccgtggaggtaataattgacgatatgatcgacggatctggtaacccagcgcggttgct
accaagtagtgaccgcttcgtgatgcaaaatccgctgacgatattcgggcgatcgctgctgaatgccat
cgagcagtaacgtggcacccgccctgccaagtcaccgcatccagactgaacagcaccaagaggctaaa
acccaatcccgccggtagcagcggagaactacccagcattggtcccaccaaagctaatgccgtcgtggta
aaaatcgcgatcgccgtcagactcaagcccagttcgctcatgcttcctcatctaggtcacagtcttcggc
gatcgcatcgatctgatgctgcagcaagcgttttccataccggcgatcgcgccgtcgcccttcgctgcc
gtggcccgcttacgagctcgtttatcgaccacgatcgcatccaaatccgcgatcgcttcccagtccggca
attcagtctggggcgtccgttcattaatcctgatcaggcacgaaattgctgtgcgtagtatcgcgcata
gcggccagcctctgccaacagcgcatcgtgattgcctgcctcaacaatctggccgcgctccatcaccaag
atgcggctggcattacgaaccgtagccagacggtgagcaatgataaagaccgtccgtccctgcatcaccc
gttctagggcctcttgcaccaaggtttcggactcggaatcaagcgccgaagtcgcctcatccagaattaa
aatgcgtgAatcctctacgccggacgcatcgtggccggcatcaccggcgccacaggtgcggttgctggcg
cctatatcgccgacatcaccgatggggaagatcgggctcgccacttcgggctcatgagcgcttgtttcgg
cgtgggtatggtggcaggccccgtggccgggggactgttgggcgccatctccttgcatgcaccattcctt TABLE 4-continued

JIB-3345US(2013-020-03)

gcggcggcggtgctcaacggcctcaacctactactgggctgcttcctaatgcaggagtcgcataagggag agcgtcgatcgaccgatgcccttgagagccttcaacccagtcagctccttccggtgggcgcggggcatga ctatcgtcgccgcacttatgactgtcttctttatcatgcaactcgtaggacaggtgccggcagcgctctg ggtcattttcggcgaggaccgctttcgctggagcgcgacgatgatcggcctgtcgcttgcggtattcgga atcttgcacgccctcgctcaagccttcgtcactggtcccgccaccaaacgtttcggcgagaagcaggcca ttatcgccggcatggcggccgacgcgctgggctacgtcttgctggcgttcgcgacgcgaggctggatggc cttccccattatgattcttctcgcttccggcggcatcgggatgcccgcgttgcaggccatgctgtccagg caggtagatgacgaccatcagggacagcttcaaggatcgctcgcggctcttaccagcctaacttcgatca ctggaccgctgatcgtcacggcgatttatgccgcctcggcgagcacatggaacgggttggcatggattgt aggcgccgccctataccttgtctgcctccccgcgttgcgtcgcggtgcatggagccgggccacctcgacc tgaatggaagccggcggcacctcgctaacggattcaccactccaagaattggagccaatcaattcttgcg gagaactgtgaatgcgcaaaccaaccccttggcagaacatatccatcgcgtccgccatctccagcagccgc acgcggcgcatctcgggcagcgttgggtcctggccacgggtgcgcatgatcgtgctcctgtcgttgagga cccggctaggctggcggggttgccttactggttagcagaatgaatcaccgatacgcgagcgaacgtgaag cgactgctgctgcaaaacgtctgcgacctgagcaacaacatgaatggtcttcggtttccgtgtttcgtaa agtctggaaacgcggaagtcagcgccctgcaccattatgttccggatctgcatcgcaggatgctgctggc taccctgtggaacacctacatctgtattaacgaagcgctggcattgaccctgagtgattttctctggtc ccgccgcatccataccgccagttgtttaccctcacaacgttccagtaaccgggcatgttcatcatcagta acccgtatcgtgagcatcctctctcgtttcatcggtatcattaccccatgaacagaaatccccccttaca cggaggcatcagtgaccaaacaggaaaaaaccgcccttaacatggcccgctttatcagaagccagacatt aacgcttctggagaaactcaacgagctggacgcggatgaacaggcagacatctgtgaatcgcttcacgac cacgctgatgagctttaccgcagctgcctcgcgcgtttcggtgatgacggtgaaaacctctgacacatgc agctcccggagacggtcacagcttgtctgtaagcggatgccgggagcagacaagcccgtcagggcgcgtc agcgggtgttggcgggtgtcggggcgcagccatgacccagtcacgtagcgatagcggagtgtatactggc ttaactatgcggcatcagagcagattgtactgagagtgcaccatatgcggtgtgaaataccgcacagatg cgtaaggagaaaataccgcatcaggcgctcttccgcttcctcgctcactgactcgctgcgctcggtcgtt cggctgcggcgagcggtatcagctcactcaaaggcggtaatacggttatccacagaatcaggggataacg caggaaagaacatgtgagcaaaaggccagcaaaaggccaggaaccgtaaaaaggccgcgttgctggcgtt tttccataggctccgcccccctgacgagcatcacaaaaatcgacgctcaagtcagaggtggcgaaacccg acaggactataaagataccaggcgtttccccctggaagctccctcgtgcgctctcctgttccgaccctgc cgcttaccggatacctgtccgcctttctcccttcgggaagcgtggcgctttctcatagctcacgctgtag gtatctcagttcggtgtaggtcgttcgctccaagctgggctgtgtgcacgaaccccccgttcagcccgac cgctgcgccttatccggtaactatcgtcttgagtccaacccggtaagacacgacttatcgccactggcag cagccactggtaacaggattagcagagcgaggtatgtaggcggtgctacagagttcttgaagtggtggcc taactacggctacactagaaggacagtatttggtatctgcgctctgctgaagccagttaccttcggaaaa agagttggtagctcttgatccggcaaacaaaccaccgctggtagcggtggtttttttgtttgcaagcagc agattacgcgcagaaaaaaggatctcaagaagatcctttgatcttttctacggggtctgacgctcagtg gaacgaaaactcacgttaagggattttggtcatgagattatcaaaaaggatcttcacctagatccttttta aattaaaaatgaagttttaaatcaatctaaagtatatatgagtaaacttggtctgacagttaccaatgct TABLE 4-continued

JIB-3345US(2013-020-03)

taatcagtgaggcacctatctcagcgatctgtctatttcgttcatccatagttgcctgactccccgtcgt
gtagataactacgatacgggagggcttaccatctggccccagtgctgcaatgataccgcgagacccacgc
tcaccggctccagatttatcagcaataaaccagccagccggaagggccgagcgcagaagtggtcctgcaa
ctttatccgcctccatccagtctattaattgttgccgggaagctagagtaagtagttcgccagttaatag
tttgcgcaacgttgttgccattgctgcaggcatcgtggtgtcacgctcgtcgtttggtatggcttcattc
agctccggttcccaacgatcaaggcgagttacatgatcccccatgttgtgcaaaaaagcggttagctcct
tcggtcctccgatcgttgtcagaagtaagttggccgcagtgttatcactcatggttatggcagcactgca
taattctcttactgtcatgccatccgtaagatgcttttctgtgactggtgagtactcaaccaagtcattc
tgagaatagtgtatgcggcgaccgagttgctcttgcccggcgtcaacacgggataataccgcgccacata
gcagaactttaaaagtgctcatcattggaaaacgttcttcggggcgaaaactctcaaggatcttaccgct
gttgagatccagttcgatgtaacccactcgtgcacccaactgatcttcagcatcttttactttcaccagc
gtttctgggtgagcaaaaacaggaaggcaaaatgccgcaaaaaagggaataagggcgacacggaaatgtt
gaatactcatactcttcctttttcaatattattgaagcatttatcagggttattgtctcatgagcggata
catatttgaatgtatttagaaaaataaacaaatagggggttccgcgcacatttccccgaaaagtgccacct
gacgtctaagaaaccattattatcatgacattaacctataaaaataggcgtatcacgaggccctttcgtc
ttcaagaattagcttgtcatctgccggatgaggcaaaaccctgcctacggcgcgattacatcgtcccagc
gcgatcgctcttactgttgatggctcgtgcttaaaaacaatgcaaacttcaccgtttcagctggtgattt
tcgactgtgatggtgtgcttgttgatagcggaacgcatcactaatcgcgtctttgcagacatgctcaatg
aactgggtctgttggtgactttggatgacatgtttgagcagtttgtgggtcattccatggctgactgtct
caaactaattgagcgacggttaggcaatcctccacccctgactttgttcagcactatcaacgccgtacc
cgtatcgcgttagaaacgcatctacaagccgttcctgggggttgaagaggctttggatgctcttgaattgc
cctactgtgttgcgtccagtggtgatcatcaaaagatgcgaaccacactgagcctgacgaagctctggcc
acgatttgagggacgaatcttcagcgtgactgaagtacctcgcggcaagccatttcccgatgtcttttg
ttggccgccgatcgcttcggggttaatcctacggcctgcgctgtgatcgaagacaccccttgggagtag
cggcaggcgtggcggcaggaatgcaagtgtttggctacgcgggttccatgcccgcttggcgtctgcaaga
agccggtgcccatctcattttttgacgatatgcgactgctgcccagtctgctccaatcgtcgccaaaagat
aactccacagcattgcccaatccctaaccccctgctcgcgccgcaactacacactaaaccgttcctgcgcg
atcgctcttactgttgatggctcgtgcttaaaaacaatgcaaccctaaccgtttcagctggtgattttcg
gacgatttggcttacagggataactgagagtcaacagcctctgtccgtcattgcacacccatccatgcac
tggggacttgactcatgctgaatcacattttccctgtccattgggcgagaggggaggggaatcttctgga
ctcttcactaagcggcgatcgcaggttcttctacccaagcagtggcgatcgcttgattgcagtcttcaat
gctggcctctgcagccatcgccgccaccaaagcatcgtaggcgggacgttgttgctccagtaaagtcttc
gcccgtaacaatccccagcgactgcgtaaatccgcttcggcaggattgcgatcgagttgccgccacagtt
gtttccactgggcgcgatcgtcagctccccttccacgttgccgtagaccagttgctctgccgctgcacc
ggccatcaacacctgacaccactgttccagcgatcgctgactgagttgcccctgtgcggcttcggcttct
agcgcagctgcttgaactgcacaccccgcgaccaggttgtccttggcgcagcgcttcccacgctgaga
gggtgtagcccgtcacgggtaaccgatatcgaattcatgA TABLE 4-continued

JIB-3345US(2013-020-03)

>pNS3  SEQ ID NO: 36
cggagtgtatactggcttactatgttggcactgatgagggtgtcagtgaagtgcttcatgtggcaggaga
aaaaaggctgcaccggtgcgtcagcagaatatgtgatacaggatatattccgcttcctcgctcactgact
cgctacgctcggtcgttcgactgcggcgagcggaaatggcttacgaacggggcggagatttcctggaaga
tgccaggaagatacttaacagggaagtgagagggccgcggcaaagccgttttccataggctccgccccc
ctgacaagcatcacgaaatctgacgctcaaatcagtggtggcgaaacccgacaggactataaagatacca
ggcgtttccccctggcggctccctcgtgcgctctcctgttcctgcctttcggtttaccggtgtcattccg
ctgttatggccgcgtttgtctcattccacgcctgacactcagttccgggtaggcagttcgctccaagctg
gactgtatgcacgaaccccccgttcagtccgaccgctgcgccttatccggtaactatcgtcttgagtcca
acccggaaagacatgcaaaagcaccactggcagcagccactggtaattgatttagaggagttagtcttga
agtcatgcgccggttaaggctaaactgaaaggacaagttttggtgactgcgctcctccaagccagttacc
tcggttcaaagagttggtagctcagagaaccttcgaaaaaccgccctgcaaggcggttttttcgttttca
gagcaagagattacgcgcagaccaaaacgatctcaagaagatcatcttattaatcagataaaatatttcT
TTTCTACGGGGTCTGACGCTCAGTCTAGTTCAGCCAGCTCGTCGTGATGTCGAAACCCAAGCCACCCTCA
GAGGTGAAGGCCGCTTCGAGCACATCGGGAAGCGTGTCGACGACGGTGCTCGGTGCCTCGGGTAAGAGCC
AGATAGATGCGGTGACGTTCACCGTCGCGATCGTGGCGGGAACCACGGTCACTGCGTCCGTTACAACTCG
CACGTCGTCGGCCAGCACGACTGACTCGACGGCTTCGATTAGCCCGGGAGAGGCAAGGCCATCAGGCTCG
GTAGACAGAATGCTGATTAACACCTCGCCGGGAGCAGGGCTGCTCACAGCCGCGTCCTTCACCCGTGGGT
CAGCCGTCAGCGCTTGATAGCGGTACCAGGCCGCACCGCCTGCGGTCGAGCTGCCCTTGATCCGCTCGAT
GGTGCGATCGCGAAGCTCGCCATCCGGCTCATTCGGCTGCCGCACCACGCCGTAGAACGCGGCAAGGTTG
TCGAGGTCGGGGCCGTTTGAGTAGCGAAGCAGTGTCGCAAGAAGTGCGTCGTTGATCCGCTGACGCAGGA
TCAGCTCGCGGGCTGCGCAGACCTCCAGCAGCTTGATGACCGGGTCGGATTCGAGGATGGCGGTGTAGCT
GGCGTCACGCGATCGCAGGTCGTCGATCAAGTCCTGCAGGATCAGTTCAAAGTCCAGCGCTTCGATGATG
GTGGGCGCGGGAATCGTAGCAAAGTCAAGAACGGTCATGAGACGACTAAGCCCTCCAGCGTGATACGCCT
GCCCTCGGGGATGTAGTAGCCGATCAGGTTCAGCTCGACTTGACCAGCTGCGCTGGCTGAGACGATGCGA
ACCTTCTCCAGCTTCAGCCGTGGCTCCCAGCGATCGAGCGCTTCAGCTGTGGCCGCCACCAGGTCAACGA
TGAGGGACTGGTTGATCGGTCTAGTCATCAAATAAAACGAAAGGCTCAGTCGAAAGACTGGGCCTTTCGT
TTTATCTGTTGTTTGTCGGTGAACGCTCTCCTGAGTAGGACAAATCCGCCGGGAGCGGATTTGAACGTTG
CGAAGCAACGGCCCGGAGGGTGGCGGGCAGGACGCCCGCCATAAACTGCCAGGCATCAAATTAAGCAGAA
GGCCATCCTGACGGATGGCCTTTTTGCGTTTCTACTCTAGTTTTTCGAAACCCCAGGCTTGACACTTTAT
GCTTCCGGCTCGTATAATGTGTGGAATTGTGAGCGGATAACAATTTCACACAAGGAGGAAAAACATATgt
ccagagaccgaaagtgaaacgtgatttcatgcgtcatttttgaacattttgtaaatcttatttaataatgt
gtgcggcaattcacatttaatttatgaatgttttcttaacatcgcggcaactcaagaaacggcaggttcG
GATCTtagctactagagaaagaggagaaatactagatgcgtaaaggcgaagagctgttcactggtgtcgt
ccctattctggtggaactggatggtgatgtcaacggtcataagttttccgtgcgtggcgagggtgaaggt
gacgcaactaatggtaaactgacgctgaagttcatctgtactactggtaaactgccggtaccttggccga
ctctggtaacgacgctgacttatggtgttcagtgctttgctcgttatccggaccatatgaagcagcatga
cttcttcaagtccgccatgccggaaggctatgtgcaggaacgcacgatttcctttaaggatgacggcacg
tacaaaacgcgtgcggaagtgaaatttgaaggcgatacccctggtaaaccgcattgagctgaaaggcattg TABLE 4-continued

JIB-3345US(2013-020-03)

actttaaagaagacggcaatatcctgggccataagctggaatacaattttaacagccacaatgtttacat
caccgccgataaacaaaaaaatggcattaaagcgaattttaaaattcgccacaacgtggaggatggcagc
gtgcagctggctgatcactaccagcaaaacactccaatcggtgatggtcctgttctgctgccagacaatc
actatctgagcacgcaaagcgttctgtctaaagatccgaacgagaaacgcgatcatatggttctgctgga
gttcgtaaccgcagcgggcatcacgcatggtatggatgaactgtacaaatgaggtctctagcgGATCGGC
ACGTAAGAGGTTCCAACTTTCACCATAATGAAATAAGATCACTACCGGGCGTATTTTTTGAGTTATCGAG
ATTTTCAGGAGCTAAGGAAGCTAAAATGGAGAAAAAAATCACTGGATATACCACCGTTGATATATCCCAA
TGGCATCGTAAAGAACATTTTGAGGCATTTCAGTCAGTTGCTCAATGTACCTATAACCAGACCGTTCAGC
TGGATATTACGGCCTTTTTAAAGACCGTAAAGAAAAATAAGCACAAGTTTTATCCGGCCTTTATTCACAT
TCTTGCCCGCCTGATGAATGCTCATCCGGAGTTCCGTATGGCAATGAAAGACGGTGAGCTGGTGATATGG
GATAGTGTTCACCCTTGTTACACCGTTTTCCATGAGCAAACTGAAACGTTTTCATCGCTCTGGAGTGAAT
ACCACGACGATTTCCGGCAGTTTCTACACATATATTCGCAAGATGTGGCGTGTTACGGTGAAAACCTGGC
CTATTTCCCTAAAGGGTTTATTGAGAATATGTTTTTCGTCTCAGCCAATCCCTGGGTGAGTTTCACCAGT
TTTGATTTAAACGTGGCCAATATGGACAACTTCTTCGCCCCCGTTTTCACTATGGGCAAATATTATACGC
AAGGCGACAAGGTGCTGATGCCGCTGGCGATTCAGGTTCATCATGCCGTCTGTGATGGCTTCCATGTCGG
CAGAATGCTTAATGAATTACAACAGTACTGCGATGAGTGGCAGGGCGGGGCGTAATTTTTTAAGGCAGT
TATTGGTGCCCTTGAATTCCTACTAGTCGAAGCGGCATGCATTTACGTTGACACCATCGAATGGTGCAAA
ACCTTTCGCGGTATGGCATGATAGCGCCCGGAAGAGAGTCAATTCAGGGTGGTGAATGTGAAACCAGTAA
CGTTATACGATGTCGCAGAGTATGCCGGTGTCTCTTATCAGACCGTTTCCCGCGTGGTGAACCAGGCCAG
CCACGTTTCTGCGAAAACGCGGGAAAAAGTGGAAGCGGCGATGGCGGAGCTGAATTACATTCCCAACCGC
GTGGCACAACAACTGGCGGGCAAACAGTCGTTGCTGATTGGCGTTGCCACCTCCAGTCTGGCCCTGCACG
CGCCGTCGCAAATTGTCGCGGCGATTAAATCTCGCGCCGATCAACTGGGTGCCAGCGTGGTGGTGTCGAT
GGTAGAACGAAGCGGCGTCGAAGCCTGTAAAGCGGCGGTGCACAATCTTCTCGCGCAACGCGTCAGTGGG
CTGATCATTAACTATCCGCTGGATGACCAGGATGCCATTGCTGTGGAAGCTGCCTGCACTAATGTTCCGG
CGTTATTTCTTGATGTCTCTGACCAGACACCCATCAACAGTATTATTTTCTCCCATGAAGACGGTACGCG
ACTGGGCGTGGAGCATCTGGTCGCATTGGGTCACCAGCAAATCGCGCTGTTAGCGGGCCCATTAAGTTCT
GTCTCGGCGCGTCTGCGTCTGGCTGGCTGGCATAAATATCTCACTCGCAATCAAATTCAGCCGATAGCGG
AACGGGAAGGCGACTGGAGTGCCATGTCCGGTTTTCAACAAACCATGCAAATGCTGAATGAGGGCATCGT
TCCCACTGCGATGCTGGTTGCCAACGATCAGATGGCGCTGGGCGCAATGCGCGCCATTACCGAGTCCGGG
CTGCGCGTTGGTGCGGATATCTCGGTAGTGGGATACGACGATACCGAAGACAGCTCATGTTATATCCCGC
CGTTAACCACCATCAAACAGGATTTTCGCCTGCTGGGGCAAACCAGCGTGGACCGCTTGCTGCAACTCTC
TCAGGGCCAGGCGGTGAAGGGCAATCAGCTGTTGCCCGTCTCACTGGTGAAAAGAAAAACCACCCTGGCG
CCCAATACGCAAACCGCCTCTCCCCGCGCGTTGGCCGATTCATTAATGCAGCTGGCACGACAGGTTTCCC
GACTGGAAAGCGGGCAGTGATCCCACAGCCGCCAGTTCCGCTGGCGGCATTTTAACTTTCTTTAATGAAT
CTAGTGACAAGCCGGGGCAGACGTGAGCCGTAGTCCCGTCGCCAGACGCGGGTGCCCACGGGCGTCGTCA
GGATGTCCGTAATTGACTGCCGGAGGTGGTCAATGCCCTTCAGCTCCTTGCCACTGTCACGGCTCATGCC
TCGGGTCATTAGTCGCCCGCTCCGGTATCTTCACTGGCTTCGATGATTGCCGCCCCGCAGCTGCAGAGGT
CACCGATCCGAGCAGTCGGCCTCTGGTTGGTAAAGACCGTGCGACTGCCGGTGATGATCGTGTTCAAGCC
ATGCAGGGGCAGGCGTGAAGGTCATCCTTTCGGGCCACGGGGCGGCTGTTGACGAAGGTGTCGTCGCTC TABLE 4-continued

JIB-3345US(2013-020-03)

```
CCGGTGATGATGATCCCGCCGTGATCGGTCACGTCGTTTAGTCGAGCGATGCCTGGCGTCGTAGTCACGG
GTTTAGGTCAATACGACTTGCGGTCACTGTAACGTTGCCCTCGGCGGTCACGTTAACGTCGCCTTGGGCT
TCGACTTGCGCCTCCTGCACAAGGATCACAATCCGTCCTTGGGCTGCGGTGAGGTCGATCTTGTACTCAT
GCGCTTCGCGGTCGTACTGGATGATTGAGTCATCCTCGAACTGCGTCTTTTGGATCGTTTCTTTGTCCTC
GATCTGGGGGTAGTCAGTCGAGAACGCGCCGGGCATCGCGAAGCCCTGACTGATCTCGCCGGAGGGGGCC
ATCACGACGACGGCCTCACCGACCTCGGGCGCCCACCAGAACCGATCCTTGCCCGCTCGCTGCGTGAGCC
ACGGAATCCAGTCAGTGAGGAGCAGCGCCTCGCCGCTCTCCTCGTCTTCCTCGATCGCGACACGGATCAG
CCCCTTGGGATAGTCAGCCTCGGCTACCCTGCCTACGCGGAGCAAGTTGCCGTGACGCCGACTGTCTCGA
GTAT
```

What is claimed is:

1. A recombinant host cell comprising heterologously expressed genes mcr, mcl, mch, mct, meh, and pcs, and a second heterologously expressed mct gene, and wherein the recombinant host cell does not naturally express the heterologously expressed genes and wherein the host cell produces a synthetic photorespiratory bypass pathway.

2. The recombinant host cell of claim 1, wherein at least one of the heterologously expressed genes is from *Chloroflexus aurantiacus* J-10-fl.

3. The recombinant host cell of claim 1, wherein at least one of the heterologously expressed genes is from *Erythrobacter* sp. NAP1.

4. The recombinant host cell of claim 1, wherein the heterologously expressed genes comprise genes having a sequence of SEQ ID NOs: 19-24 or functional homologs thereof.

5. The recombinant host cell of claim 4, wherein the functional homologs comprise genes having a sequence of SEQ ID NOs: 25-30.

6. The recombinant host cell of claim 1, wherein the second heterologous mct gene is from the same organism as the mct gene.

7. The recombinant host cell of claim 1, wherein the second heterologous mct gene is from a different organism than the mct gene.

8. The recombinant host cell of claim 1, wherein one or more of the heterologously expressed genes is encoded from a DNA expression cassette.

9. The recombinant host cell of claim 8, wherein the DNA expression cassette comprises a promoter operably linked to the one or more heterologously expressed genes.

10. The recombinant host cell of claim 8, wherein the expression cassette has a sequence in accordance with any of SEQ ID NOs: 31-34.

11. The recombinant host cell of claim 8, wherein the expression cassette comprises a selectable marker.

12. The recombinant host cell of claim 8 wherein the expression cassette comprises an inducible promoter.

13. The recombinant host cell of claim 12 wherein the inducible promoter is an IPTG-inducible promoter.

14. The recombinant host cell of claim 1, wherein the heterologously expressed genes are stably incorporated into the recombinant host cell.

15. The recombinant host cell of claim 1, wherein the heterologously expressed genes are stably incorporated into the genome of the recombinant host cell.

16. The recombinant host cell of claim 1, wherein the heterologously expressed genes are transiently expressed from a plasmid.

17. The recombinant host cell of claim 1, wherein the recombinant host cell is a bacterial cell, a cyanobacterial cell, an oxygenic photoautotroph or a plant cell.

18. A recombinant host cell comprising stably transformed heterologous genes having sequences of SEQ ID Nos: 19-24 or functional homologs thereof wherein SEQ ID No: 23 encodes a first heterologously expressed mct gene, and wherein the recombinant host cell comprises a second heterologously expressed mct gene, wherein the host cell produces a synthetic photorespiratory bypass pathway.

19. The recombinant host cell of claim 18, wherein the recombinant host cell is a bacterial cell, a cyanobacterial cell, an oxygenic photoautotroph or a plant cell.

20. The recombinant host cell of claim 18, wherein the functional homologs comprise genes having a sequence of SEQ ID NOs: 25-30.

* * * * *

SEQUENCE LISTING

<160> NUMBER OF SEQ ID NOS: 36

<210> SEQ ID NO 1
<211> LENGTH: 40
<212> TYPE: DNA
<213> ORGANISM: Synechococcus elongatus

<400> SEQUENCE: 1
gcatagaatt catgagatct gtttagtgcg atcgcggcag       40

<210> SEQ ID NO 2
<211> LENGTH: 39
<212> TYPE: DNA
<213> ORGANISM: Synechococcus elongatus

<400> SEQUENCE: 2
ctaggggatc cgggcaagag tcttagttaa aaactcttg        39

<210> SEQ ID NO 3
<211> LENGTH: 61
<212> TYPE: DNA
<213> ORGANISM: Chloroflexus aurantiacus

<400> SEQUENCE: 3
gcatagaatt catgagatct cttggaggaa tccattaatg cgcaagctag ctcacaactt    60
c                                                                   61

<210> SEQ ID NO 4
<211> LENGTH: 32
<212> TYPE: DNA
<213> ORGANISM: Chloroflexus aurantiacus

<400> SEQUENCE: 4
ctaggggatc ctcacagacc atacgcctgg gc               32

<210> SEQ ID NO 5
<211> LENGTH: 60
<212> TYPE: DNA
<213> ORGANISM: Chloroflexus aurantiacus

<400> SEQUENCE: 5
gcatagaatt catgagatct cttggaggaa tccattaatg agcgctaaaa ccaatcccgg    60

```
<210> SEQ ID NO 6
<211> LENGTH: 30
<212> TYPE: DNA
<213> ORGANISM: Chloroflexus aurantiacus

<400> SEQUENCE: 6
ctaggggatc ctcatccccg acgcggcatc                               30

<210> SEQ ID NO 7
<211> LENGTH: 62
<212> TYPE: DNA
<213> ORGANISM: Chloroflexus aurantiacus

<400> SEQUENCE: 7
gcatagaatt catgagatct cttggaggaa tccattaatg aagggtattc tccacggatt    60
gc                                                              62

<210> SEQ ID NO 8
<211> LENGTH: 31
<212> TYPE: DNA
<213> ORGANISM: Chloroflexus aurantiacus

<400> SEQUENCE: 8
ctaggggatc cctacgctgc ccgatctggc c                              31

<210> SEQ ID NO 9
<211> LENGTH: 55
<212> TYPE: DNA
<213> ORGANISM: Chloroflexus aurantiacus

<400> SEQUENCE: 9
gcatagaatt catgagatct cttggaggaa tccattaatg gcgtggagcc acccg     55

<210> SEQ ID NO 10
<211> LENGTH: 33
<212> TYPE: DNA
<213> ORGANISM: Chloroflexus aurantiacus

<400> SEQUENCE: 10
ctaggggatc ctcatccccc caactcaacc gtc                            33

<210> SEQ ID NO 11
<211> LENGTH: 60
<212> TYPE: DNA
<213> ORGANISM: Chloroflexus aurantiacus

<400> SEQUENCE: 11
gcatagaatt catgagatct cttggaggaa tccattaatg agcggaacag gacgactggc    60

<210> SEQ ID NO 12
<211> LENGTH: 33
<212> TYPE: DNA
<213> ORGANISM: Chloroflexus aurantiacus

<400> SEQUENCE: 12
ctaggggatc cttacacggt aatcgcccgt ccg                            33

<210> SEQ ID NO 13
<211> LENGTH: 31
<212> TYPE: DNA
<213> ORGANISM: Chloroflexus aurantiacus
```

<400> SEQUENCE: 13
ctagctagca tatgatcgac actgcgcccc t                                   31

<210> SEQ ID NO 14
<211> LENGTH: 30
<212> TYPE: DNA
<213> ORGANISM: Chloroflexus aurantiacus

<400> SEQUENCE: 14
ctagctaaag cttctaccgc tcgccggccg                                      30

<210> SEQ ID NO 15
<211> LENGTH: 32
<212> TYPE: DNA
<213> ORGANISM: Candidatus Accumulibacter phosphatis

<400> SEQUENCE: 15
atatatatac atatggatgg cattctgaag gg                                   32

<210> SEQ ID NO 16
<211> LENGTH: 30
<212> TYPE: DNA
<213> ORGANISM: Candidatus Accumulibacter phosphatis

<400> SEQUENCE: 16
atatactcga gttatgtcgg acctgccacc                                      30

<210> SEQ ID NO 17
<211> LENGTH: 32
<212> TYPE: DNA
<213> ORGANISM: candidatus accumulibacter phosphatis

<400> SEQUENCE: 17
atatatatac atatggatgg cattctgaag gg                                   32

<210> SEQ ID NO 18
<211> LENGTH: 30
<212> TYPE: DNA
<213> ORGANISM: Candidatus Accumulibacter phosphatis

<400> SEQUENCE: 18
atatactcga gttatgtcgg acctgccacc                                      30

<210> SEQ ID NO 19
<211> LENGTH: 1822
<212> TYPE: PRT
<213> ORGANISM: Chloroflexus aurantiacus

<400> SEQUENCE: 19

Met Ile Asp Thr Ala Pro Leu Ala Pro Pro Arg Ala Pro Arg Ser Asn
1               5                   10                  15

Pro Ile Arg Asp Arg Val Asp Trp Glu Ala Gln Arg Ala Ala Ala Leu
            20                  25                  30

Ala Asp Pro Gly Ala Phe His Gly Ala Ile Ala Arg Thr Val Ile His
        35                  40                  45

Trp Tyr Asp Pro Gln His His Cys Trp Ile Arg Phe Asn Glu Ser Ser
    50                  55                  60

Gln Arg Trp Glu Gly Leu Asp Ala Ala Thr Gly Ala Pro Val Thr Val
65                  70                  75                  80

Asp Tyr Pro Ala Asp Tyr Gln Pro Trp Gln Gln Ala Phe Asp Asp Ser
                85                  90                  95

```
Glu Ala Pro Phe Tyr Arg Trp Phe Ser Gly Gly Leu Thr Asn Ala Cys
            100                 105                 110

Phe Asn Glu Val Asp Arg His Val Thr Met Gly Tyr Gly Asp Glu Val
            115                 120                 125

Ala Tyr Tyr Phe Glu Gly Asp Arg Trp Asp Asn Ser Leu Asn Asn Gly
130                 135                 140

Arg Gly Gly Pro Val Val Gln Glu Thr Ile Thr Arg Arg Leu Leu
145                 150                 155                 160

Val Glu Val Val Lys Ala Ala Gln Val Leu Arg Asp Leu Gly Leu Lys
                165                 170                 175

Lys Gly Asp Arg Ile Ala Leu Asn Met Pro Asn Ile Met Pro Gln Ile
            180                 185                 190

Tyr Tyr Thr Glu Ala Ala Lys Arg Leu Gly Ile Leu Tyr Thr Pro Val
            195                 200                 205

Phe Gly Gly Phe Ser Asp Lys Thr Leu Ser Asp Arg Ile His Asn Ala
            210                 215                 220

Gly Ala Arg Val Val Ile Thr Ser Asp Gly Ala Tyr Arg Asn Ala Gln
225                 230                 235                 240

Val Val Pro Tyr Lys Glu Ala Tyr Thr Asp Gln Ala Leu Asp Lys Tyr
                245                 250                 255

Ile Pro Val Glu Thr Ala Gln Ala Ile Val Ala Gln Thr Leu Ala Thr
            260                 265                 270

Leu Pro Leu Thr Glu Ser Gln Arg Gln Thr Ile Ile Thr Glu Val Glu
            275                 280                 285

Ala Ala Leu Ala Gly Glu Ile Thr Val Glu Arg Ser Asp Val Met Arg
290                 295                 300

Gly Val Gly Ser Ala Leu Ala Lys Leu Arg Asp Leu Asp Ala Ser Val
305                 310                 315                 320

Gln Ala Lys Val Arg Thr Val Leu Ala Gln Ala Leu Val Glu Ser Pro
                325                 330                 335

Pro Arg Val Glu Ala Val Val Val Arg His Thr Gly Gln Glu Ile
            340                 345                 350

Leu Trp Asn Glu Gly Arg Asp Arg Trp Ser His Asp Leu Leu Asp Ala
            355                 360                 365

Ala Leu Ala Lys Ile Leu Ala Asn Ala Arg Ala Gly Phe Asp Val
370                 375                 380

His Ser Glu Asn Asp Leu Leu Asn Leu Pro Asp Asp Gln Leu Ile Arg
385                 390                 395                 400

Ala Leu Tyr Ala Ser Ile Pro Cys Glu Pro Val Asp Ala Glu Tyr Pro
                405                 410                 415

Met Phe Ile Ile Tyr Thr Ser Gly Ser Thr Gly Lys Pro Lys Gly Val
            420                 425                 430

Ile His Val His Gly Gly Tyr Val Ala Gly Val Val His Thr Leu Arg
            435                 440                 445

Val Ser Phe Asp Ala Glu Pro Gly Asp Thr Ile Tyr Val Ile Ala Asp
            450                 455                 460

Pro Gly Trp Ile Thr Gly Gln Ser Tyr Met Leu Thr Ala Thr Met Ala
465                 470                 475                 480

Gly Arg Leu Thr Gly Val Ile Ala Glu Gly Ser Pro Leu Phe Pro Ser
                485                 490                 495

Ala Gly Arg Tyr Ala Ser Ile Ile Glu Arg Tyr Gly Val Gln Ile Phe
            500                 505                 510
```

-continued

```
Lys Ala Gly Val Thr Phe Leu Lys Thr Val Met Ser Asn Pro Gln Asn
            515                 520                 525
Val Glu Asp Val Arg Leu Tyr Asp Met His Ser Leu Arg Val Ala Thr
        530                 535                 540
Phe Cys Ala Glu Pro Val Ser Pro Ala Val Gln Gln Phe Gly Met Gln
545                 550                 555                 560
Ile Met Thr Pro Gln Tyr Ile Asn Ser Tyr Trp Ala Thr Glu His Gly
                565                 570                 575
Gly Ile Val Trp Thr His Phe Tyr Gly Asn Gln Asp Phe Pro Leu Arg
            580                 585                 590
Pro Asp Ala His Thr Tyr Pro Leu Pro Trp Val Met Gly Asp Val Trp
        595                 600                 605
Val Ala Glu Thr Asp Glu Ser Gly Thr Thr Arg Tyr Arg Val Ala Asp
    610                 615                 620
Phe Asp Glu Lys Gly Glu Ile Val Ile Thr Ala Pro Tyr Pro Tyr Leu
625                 630                 635                 640
Thr Arg Thr Leu Trp Gly Asp Val Pro Gly Phe Glu Ala Tyr Leu Arg
                645                 650                 655
Gly Glu Ile Pro Leu Arg Ala Trp Lys Gly Asp Ala Glu Arg Phe Val
            660                 665                 670
Lys Thr Tyr Trp Arg Arg Gly Pro Asn Gly Glu Trp Gly Tyr Ile Gln
        675                 680                 685
Gly Asp Phe Ala Ile Lys Tyr Pro Asp Gly Ser Phe Thr Leu His Gly
    690                 695                 700
Arg Ser Asp Asp Val Ile Asn Val Ser Gly His Arg Met Gly Thr Glu
705                 710                 715                 720
Glu Ile Glu Gly Ala Ile Leu Arg Asp Arg Gln Ile Thr Pro Asp Ser
                725                 730                 735
Pro Val Gly Asn Cys Ile Val Val Gly Ala Pro His Arg Glu Lys Gly
            740                 745                 750
Leu Thr Pro Val Ala Phe Ile Gln Pro Ala Pro Gly Arg His Leu Thr
        755                 760                 765
Gly Ala Asp Arg Arg Arg Leu Asp Glu Leu Val Arg Thr Glu Lys Gly
    770                 775                 780
Ala Val Ser Val Pro Glu Asp Tyr Ile Glu Val Ser Ala Phe Pro Glu
785                 790                 795                 800
Thr Arg Ser Gly Lys Tyr Met Arg Arg Phe Leu Arg Asn Met Met Leu
                805                 810                 815
Asp Glu Pro Leu Gly Asp Thr Thr Leu Arg Asn Pro Glu Val Leu
            820                 825                 830
Glu Glu Ile Ala Ala Lys Ile Ala Glu Trp Lys Arg Arg Gln Arg Met
            835                 840                 845
Ala Glu Glu Gln Gln Ile Ile Glu Arg Tyr Arg Tyr Phe Arg Ile Glu
    850                 855                 860
Tyr His Pro Pro Thr Ala Ser Ala Gly Lys Leu Ala Val Val Thr Val
865                 870                 875                 880
Thr Asn Pro Pro Val Asn Ala Leu Asn Glu Arg Ala Leu Asp Glu Leu
                885                 890                 895
Asn Thr Ile Val Asp His Leu Ala Arg Arg Gln Asp Val Ala Ala Ile
            900                 905                 910
Val Phe Thr Gly Gln Gly Ala Arg Ser Phe Val Ala Gly Ala Asp Ile
        915                 920                 925
Arg Gln Leu Leu Glu Glu Ile His Thr Val Glu Glu Ala Met Ala Leu
```

-continued

```
            930             935             940
Pro Asn Asn Ala His Leu Ala Phe Arg Lys Ile Glu Arg Met Asn Lys
945                 950             955                 960
Pro Cys Ile Ala Ala Ile Asn Gly Val Ala Leu Gly Gly Gly Leu Glu
                965             970             975
Phe Ala Met Ala Cys His Tyr Arg Val Ala Asp Val Tyr Ala Glu Phe
            980             985             990
Gly Gln Pro Glu Ile Asn Leu Arg Leu Leu Pro Gly Tyr Gly Gly Thr
        995             1000            1005
Gln Arg Leu Pro Arg Leu Leu Tyr Lys Arg Asn Asn Gly Thr Gly
    1010            1015            1020
Leu Leu Arg Ala Leu Glu Met Ile Leu Gly Gly Arg Ser Val Pro
    1025            1030            1035
Ala Asp Glu Ala Leu Glu Leu Gly Leu Ile Asp Ala Ile Ala Thr
    1040            1045            1050
Gly Asp Gln Asp Ser Leu Ser Leu Ala Cys Ala Leu Ala Arg Ala
    1055            1060            1065
Ala Ile Gly Ala Asp Gly Gln Leu Ile Glu Ser Ala Ala Val Thr
    1070            1075            1080
Gln Ala Phe Arg His Arg His Glu Gln Leu Asp Glu Trp Arg Lys
    1085            1090            1095
Pro Asp Pro Arg Phe Ala Asp Asp Glu Leu Arg Ser Ile Ile Ala
    1100            1105            1110
His Pro Arg Ile Glu Arg Ile Arg Gln Ala His Thr Val Gly
    1115            1120            1125
Arg Asp Ala Ala Val His Arg Ala Leu Asp Ala Ile Arg Tyr Gly
    1130            1135            1140
Ile Ile His Gly Phe Glu Ala Gly Leu Glu His Glu Ala Lys Leu
    1145            1150            1155
Phe Ala Glu Ala Val Val Asp Pro Asn Gly Gly Lys Arg Gly Ile
    1160            1165            1170
Arg Glu Phe Leu Asp Arg Gln Ser Ala Pro Leu Pro Thr Arg Arg
    1175            1180            1185
Pro Leu Ile Thr Pro Glu Gln Glu Leu Leu Arg Asp Gln Lys
    1190            1195            1200
Glu Leu Leu Pro Val Gly Ser Pro Phe Phe Pro Gly Val Asp Arg
    1205            1210            1215
Ile Pro Lys Trp Gln Tyr Ala Gln Ala Val Ile Arg Asp Pro Asp
    1220            1225            1230
Thr Gly Ala Ala Ala His Gly Asp Pro Ile Val Ala Glu Lys Gln
    1235            1240            1245
Ile Ile Val Pro Val Glu Arg Pro Arg Ala Asn Gln Ala Leu Ile
    1250            1255            1260
Tyr Val Leu Ala Ser Glu Val Asn Phe Asn Asp Ile Trp Ala Ile
    1265            1270            1275
Thr Gly Ile Pro Val Ser Arg Phe Asp Glu His Asp Arg Asp Trp
    1280            1285            1290
His Val Thr Gly Ser Gly Gly Ile Gly Leu Ile Val Ala Leu Gly
    1295            1300            1305
Glu Glu Ala Arg Arg Glu Gly Arg Leu Lys Val Gly Asp Leu Val
    1310            1315            1320
Ala Ile Tyr Ser Gly Gln Ser Asp Leu Leu Ser Pro Leu Met Gly
    1325            1330            1335
```

-continued

```
Leu Asp Pro Met Ala Ala Asp Phe Val Ile Gln Gly Asn Asp Thr
    1340                1345                1350
Pro Asp Gly Ser His Gln Gln Phe Met Leu Ala Gln Ala Pro Gln
    1355                1360                1365
Cys Leu Pro Ile Pro Thr Asp Met Ser Ile Glu Ala Ala Gly Ser
    1370                1375                1380
Tyr Ile Leu Asn Leu Gly Thr Ile Tyr Arg Ala Leu Phe Thr Thr
    1385                1390                1395
Leu Gln Ile Lys Ala Gly Arg Thr Ile Phe Ile Glu Gly Ala Ala
    1400                1405                1410
Thr Gly Thr Gly Leu Asp Ala Ala Arg Ser Ala Ala Arg Asn Gly
    1415                1420                1425
Leu Arg Val Ile Gly Met Val Ser Ser Ser Ser Arg Ala Ser Thr
    1430                1435                1440
Leu Leu Ala Ala Gly Ala His Gly Ala Ile Asn Arg Lys Asp Pro
    1445                1450                1455
Glu Val Ala Asp Cys Phe Thr Arg Val Pro Glu Asp Pro Ser Ala
    1460                1465                1470
Trp Ala Ala Trp Glu Ala Ala Gly Gln Pro Leu Leu Ala Met Phe
    1475                1480                1485
Arg Ala Gln Asn Asp Gly Arg Leu Ala Asp Tyr Val Val Ser His
    1490                1495                1500
Ala Gly Glu Thr Ala Phe Pro Arg Ser Phe Gln Leu Leu Gly Glu
    1505                1510                1515
Pro Arg Asp Gly His Ile Pro Thr Leu Thr Phe Tyr Gly Ala Thr
    1520                1525                1530
Ser Gly Tyr His Phe Thr Phe Leu Gly Lys Pro Gly Ser Ala Ser
    1535                1540                1545
Pro Thr Glu Met Leu Arg Arg Ala Asn Leu Arg Ala Gly Glu Ala
    1550                1555                1560
Val Leu Ile Tyr Tyr Gly Val Gly Ser Asp Asp Leu Val Asp Thr
    1565                1570                1575
Gly Gly Leu Glu Ala Ile Glu Ala Ala Arg Gln Met Gly Ala Arg
    1580                1585                1590
Ile Val Val Val Thr Val Ser Asp Ala Gln Arg Glu Phe Val Leu
    1595                1600                1605
Ser Leu Gly Phe Gly Ala Ala Leu Arg Gly Val Val Ser Leu Ala
    1610                1615                1620
Glu Leu Lys Arg Arg Phe Gly Asp Glu Phe Glu Trp Pro Arg Thr
    1625                1630                1635
Met Pro Pro Leu Pro Asn Ala Arg Gln Asp Pro Gln Gly Leu Lys
    1640                1645                1650
Glu Ala Val Arg Arg Phe Asn Asp Leu Val Phe Lys Pro Leu Gly
    1655                1660                1665
Ser Ala Val Gly Val Phe Leu Arg Ser Ala Asp Asn Pro Arg Gly
    1670                1675                1680
Tyr Pro Asp Leu Ile Ile Glu Arg Ala Ala His Asp Ala Leu Ala
    1685                1690                1695
Val Ser Ala Met Leu Ile Lys Pro Phe Thr Gly Arg Ile Val Tyr
    1700                1705                1710
Phe Glu Asp Ile Gly Gly Arg Arg Tyr Ser Phe Phe Ala Pro Gln
    1715                1720                1725
```

Ile Trp Val Arg Gln Arg Arg Ile Tyr Met Pro Thr Ala Gln Ile
    1730                1735                1740

Phe Gly Thr His Leu Ser Asn Ala Tyr Glu Ile Leu Arg Leu Asn
    1745                1750                1755

Asp Glu Ile Ser Ala Gly Leu Leu Thr Ile Thr Glu Pro Ala Val
    1760                1765                1770

Val Pro Trp Asp Glu Leu Pro Glu Ala His Gln Ala Met Trp Glu
    1775                1780                1785

Asn Arg His Thr Ala Ala Thr Tyr Val Val Asn His Ala Leu Pro
    1790                1795                1800

Arg Leu Gly Leu Lys Asn Arg Asp Glu Leu Tyr Glu Ala Trp Thr
    1805                1810                1815

Ala Gly Glu Arg
    1820

<210> SEQ ID NO 20
<211> LENGTH: 1220
<212> TYPE: PRT
<213> ORGANISM: Chloroflexus aurantiacus

<400> SEQUENCE: 20

Met Ser Gly Thr Gly Arg Leu Ala Gly Lys Ile Ala Leu Ile Thr Gly
 1               5                  10                  15

Gly Ala Gly Asn Ile Gly Ser Glu Leu Thr Arg Arg Phe Leu Ala Glu
                20                  25                  30

Gly Ala Thr Val Ile Ile Ser Gly Arg Asn Arg Ala Lys Leu Thr Ala
            35                  40                  45

Leu Ala Glu Arg Met Gln Ala Glu Ala Gly Val Pro Ala Lys Arg Ile
        50                  55                  60

Asp Leu Glu Val Met Asp Gly Ser Asp Pro Val Ala Val Arg Ala Gly
65                  70                  75                  80

Ile Glu Ala Ile Val Ala Arg His Gly Gln Ile Asp Ile Leu Val Asn
                85                  90                  95

Asn Ala Gly Ser Ala Gly Ala Gln Arg Arg Leu Ala Glu Ile Pro Leu
            100                 105                 110

Thr Glu Ala Glu Leu Gly Pro Gly Ala Glu Glu Thr Leu His Ala Ser
        115                 120                 125

Ile Ala Asn Leu Leu Gly Met Gly Trp His Leu Met Arg Ile Ala Ala
    130                 135                 140

Pro His Met Pro Val Gly Ser Ala Val Ile Asn Val Ser Thr Ile Phe
145                 150                 155                 160

Ser Arg Ala Glu Tyr Tyr Gly Arg Ile Pro Tyr Val Thr Pro Lys Ala
                165                 170                 175

Ala Leu Asn Ala Leu Ser Gln Leu Ala Ala Arg Glu Leu Gly Ala Arg
            180                 185                 190

Gly Ile Arg Val Asn Thr Ile Phe Pro Gly Pro Ile Glu Ser Asp Arg
        195                 200                 205

Ile Arg Thr Val Phe Gln Arg Met Asp Gln Leu Lys Gly Arg Pro Glu
    210                 215                 220

Gly Asp Thr Ala His His Phe Leu Asn Thr Met Arg Leu Cys Arg Ala
225                 230                 235                 240

Asn Asp Gln Gly Ala Leu Glu Arg Arg Phe Pro Ser Val Gly Asp Val
                245                 250                 255

Ala Asp Ala Ala Val Phe Leu Ala Ser Ala Glu Ser Ala Ala Leu Ser
            260                 265                 270

```
Gly Glu Thr Ile Glu Val Thr His Gly Met Glu Leu Pro Ala Cys Ser
            275                 280                 285

Glu Thr Ser Leu Leu Ala Arg Thr Asp Leu Arg Thr Ile Asp Ala Ser
290                 295                 300

Gly Arg Thr Thr Leu Ile Cys Ala Gly Asp Gln Ile Glu Glu Val Met
305                 310                 315                 320

Ala Leu Thr Gly Met Leu Arg Thr Cys Gly Ser Glu Val Ile Ile Gly
            325                 330                 335

Phe Arg Ser Ala Ala Ala Leu Ala Gln Phe Glu Gln Ala Val Asn Glu
            340                 345                 350

Ser Arg Arg Leu Ala Gly Ala Asp Phe Thr Pro Pro Ile Ala Leu Pro
            355                 360                 365

Leu Asp Pro Arg Asp Pro Ala Thr Ile Asp Ala Val Phe Asp Trp Gly
370                 375                 380

Ala Gly Glu Asn Thr Gly Gly Ile His Ala Ala Val Ile Leu Pro Ala
385                 390                 395                 400

Thr Ser His Glu Pro Ala Pro Cys Val Ile Glu Val Asp Asp Glu Arg
                405                 410                 415

Val Leu Asn Phe Leu Ala Asp Glu Ile Thr Gly Thr Ile Val Ile Ala
            420                 425                 430

Ser Arg Leu Ala Arg Tyr Trp Gln Ser Gln Arg Leu Thr Pro Gly Ala
            435                 440                 445

Arg Ala Arg Gly Pro Arg Val Ile Phe Leu Ser Asn Gly Ala Asp Gln
450                 455                 460

Asn Gly Asn Val Tyr Gly Arg Ile Gln Ser Ala Ile Gly Gln Leu
465                 470                 475                 480

Ile Arg Val Trp Arg His Glu Ala Glu Leu Asp Tyr Gln Arg Ala Ser
            485                 490                 495

Ala Ala Gly Asp His Val Leu Pro Pro Val Trp Ala Asn Gln Ile Val
            500                 505                 510

Arg Phe Ala Asn Arg Ser Leu Glu Gly Leu Glu Phe Ala Cys Ala Trp
            515                 520                 525

Thr Ala Gln Leu Leu His Ser Gln Arg His Ile Asn Glu Ile Thr Leu
            530                 535                 540

Asn Ile Pro Ala Asn Ile Ser Ala Thr Thr Gly Ala Arg Ser Ala Ser
545                 550                 555                 560

Val Gly Trp Ala Glu Ser Leu Ile Gly Leu His Leu Gly Lys Val Ala
            565                 570                 575

Leu Ile Thr Gly Gly Ser Ala Gly Ile Gly Gly Gln Ile Gly Arg Leu
            580                 585                 590

Leu Ala Leu Ser Gly Ala Arg Val Met Leu Ala Ala Arg Asp Arg His
            595                 600                 605

Lys Leu Glu Gln Met Gln Ala Met Ile Gln Ser Glu Leu Ala Glu Val
            610                 615                 620

Gly Tyr Thr Asp Val Glu Asp Arg Val His Ile Ala Pro Gly Cys Asp
625                 630                 635                 640

Val Ser Ser Glu Ala Gln Leu Ala Asp Leu Val Glu Arg Thr Leu Ser
                645                 650                 655

Ala Phe Gly Thr Val Asp Tyr Leu Ile Asn Asn Ala Gly Ile Ala Gly
            660                 665                 670

Val Glu Glu Met Val Ile Asp Met Pro Val Glu Gly Trp Arg His Thr
            675                 680                 685
```

```
Leu Phe Ala Asn Leu Ile Ser Asn Tyr Ser Leu Met Arg Lys Leu Ala
    690                 695                 700

Pro Leu Met Lys Lys Gln Gly Ser Gly Tyr Ile Leu Asn Val Ser Ser
705                 710                 715                 720

Tyr Phe Gly Gly Glu Lys Asp Ala Ala Ile Pro Tyr Pro Asn Arg Ala
                725                 730                 735

Asp Tyr Ala Val Ser Lys Ala Gly Gln Arg Ala Met Ala Glu Val Phe
            740                 745                 750

Ala Arg Phe Leu Gly Pro Glu Ile Gln Ile Asn Ala Ile Ala Pro Gly
        755                 760                 765

Pro Val Glu Gly Asp Arg Leu Arg Gly Thr Gly Glu Arg Pro Gly Leu
770                 775                 780

Phe Ala Arg Arg Ala Arg Leu Ile Leu Glu Asn Lys Arg Leu Asn Glu
785                 790                 795                 800

Leu His Ala Ala Leu Ile Ala Ala Arg Thr Asp Glu Arg Ser Met
                805                 810                 815

His Glu Leu Val Glu Leu Leu Pro Asn Asp Val Ala Leu Glu
            820                 825                 830

Gln Asn Pro Ala Ala Pro Thr Ala Leu Arg Glu Leu Ala Arg Arg Phe
        835                 840                 845

Arg Ser Glu Gly Asp Pro Ala Ala Ser Ser Ser Ala Leu Leu Asn
850                 855                 860

Arg Ser Ile Ala Ala Lys Leu Leu Ala Arg Leu His Asn Gly Gly Tyr
865                 870                 875                 880

Val Leu Pro Ala Asp Ile Phe Ala Asn Leu Pro Asn Pro Pro Asp Pro
                885                 890                 895

Phe Phe Thr Arg Ala Gln Ile Asp Arg Glu Ala Arg Lys Val Arg Asp
            900                 905                 910

Gly Ile Met Gly Met Leu Tyr Leu Gln Arg Met Pro Thr Glu Phe Asp
        915                 920                 925

Val Ala Met Ala Thr Val Tyr Tyr Leu Ala Asp Arg Asn Val Ser Gly
    930                 935                 940

Glu Thr Phe His Pro Ser Gly Gly Leu Arg Tyr Glu Arg Thr Pro Thr
945                 950                 955                 960

Gly Gly Glu Leu Phe Gly Leu Pro Ser Pro Glu Arg Leu Ala Glu Leu
                965                 970                 975

Val Gly Ser Thr Val Tyr Leu Ile Gly Glu His Leu Thr Glu His Leu
            980                 985                 990

Asn Leu Leu Ala Arg Ala Tyr Leu Glu Arg Tyr Gly Ala Arg Gln Val
        995                 1000                1005

Val Met Ile Val Glu Thr Glu Thr Gly Ala Glu Thr Met Arg Arg
    1010                1015                1020

Leu Leu His Asp His Val Glu Ala Gly Arg Leu Met Thr Ile Val
    1025                1030                1035

Ala Gly Asp Gln Ile Glu Ala Ala Ile Asp Gln Ala Ile Thr Arg
    1040                1045                1050

Tyr Gly Arg Pro Gly Pro Val Val Cys Thr Pro Phe Arg Pro Leu
    1055                1060                1065

Pro Thr Val Pro Leu Val Gly Arg Lys Asp Ser Asp Trp Ser Thr
    1070                1075                1080

Val Leu Ser Glu Ala Glu Phe Ala Glu Leu Cys Glu His Gln Leu
    1085                1090                1095

Thr His His Phe Arg Val Ala Arg Lys Ile Ala Leu Ser Asp Gly
```

```
              1100                1105                1110

Ala  Ser  Leu  Ala  Leu  Val  Thr  Pro  Glu  Thr  Thr  Ala  Thr  Ser  Thr
     1115                1120                1125

Thr  Glu  Gln  Phe  Ala  Leu  Ala  Asn  Phe  Ile  Lys  Thr  Thr  Leu  His
     1130                1135                1140

Ala  Phe  Thr  Ala  Thr  Ile  Gly  Val  Glu  Ser  Glu  Arg  Thr  Ala  Gln
     1145                1150                1155

Arg  Ile  Leu  Ile  Asn  Gln  Val  Asp  Leu  Thr  Arg  Arg  Ala  Arg  Ala
     1160                1165                1170

Glu  Glu  Pro  Arg  Asp  Pro  His  Glu  Arg  Gln  Gln  Glu  Leu  Glu  Arg
     1175                1180                1185

Phe  Ile  Glu  Ala  Val  Leu  Leu  Val  Thr  Ala  Pro  Leu  Pro  Pro  Glu
     1190                1195                1200

Ala  Asp  Thr  Arg  Tyr  Ala  Gly  Arg  Ile  His  Arg  Gly  Arg  Ala  Ile
     1205                1210                1215

Thr  Val
     1220

<210> SEQ ID NO 21
<211> LENGTH: 348
<212> TYPE: PRT
<213> ORGANISM: Chloroflexus aurantiacus

<400> SEQUENCE: 21

Met  Arg  Lys  Leu  Ala  His  Asn  Phe  Tyr  Lys  Pro  Leu  Ala  Ile  Gly  Ala
1                   5                   10                  15

Pro  Glu  Pro  Ile  Arg  Glu  Leu  Pro  Val  Arg  Pro  Glu  Arg  Val  Val  His
            20                  25                  30

Phe  Phe  Pro  Pro  His  Val  Glu  Lys  Ile  Arg  Ala  Arg  Ile  Pro  Glu  Val
        35                  40                  45

Ala  Lys  Gln  Val  Asp  Val  Leu  Cys  Gly  Asn  Leu  Glu  Asp  Ala  Ile  Pro
    50                  55                  60

Met  Asp  Ala  Lys  Glu  Ala  Ala  Arg  Asn  Gly  Phe  Ile  Glu  Val  Val  Lys
65                  70                  75                  80

Ala  Thr  Asp  Phe  Gly  Asp  Thr  Ala  Leu  Trp  Val  Arg  Val  Asn  Ala  Leu
                85                  90                  95

Asn  Ser  Pro  Trp  Val  Leu  Asp  Asp  Ile  Ala  Glu  Ile  Val  Ala  Ala  Val
            100                 105                 110

Gly  Asn  Lys  Leu  Asp  Val  Ile  Met  Ile  Pro  Lys  Val  Glu  Gly  Pro  Trp
        115                 120                 125

Asp  Ile  His  Phe  Val  Asp  Gln  Tyr  Leu  Ala  Leu  Leu  Glu  Ala  Arg  His
    130                 135                 140

Gln  Ile  Lys  Lys  Pro  Ile  Leu  Ile  His  Ala  Leu  Leu  Glu  Thr  Ala  Gln
145                 150                 155                 160

Gly  Met  Val  Asn  Leu  Glu  Glu  Ile  Ala  Gly  Ala  Ser  Pro  Arg  Met  His
                165                 170                 175

Gly  Phe  Ser  Leu  Gly  Pro  Ala  Asp  Leu  Ala  Ala  Ser  Arg  Gly  Met  Lys
            180                 185                 190

Thr  Thr  Arg  Val  Gly  Gly  Gly  His  Pro  Phe  Tyr  Gly  Val  Leu  Ala  Asp
        195                 200                 205

Pro  Gln  Glu  Gly  Gln  Ala  Glu  Arg  Pro  Phe  Tyr  Gln  Gln  Asp  Leu  Trp
    210                 215                 220

His  Tyr  Thr  Ile  Ala  Arg  Met  Val  Asp  Val  Ala  Val  Ala  His  Gly  Leu
225                 230                 235                 240
```

```
Arg Ala Phe Tyr Gly Pro Phe Gly Asp Ile Lys Asp Glu Ala Ala Cys
                245                 250                 255

Glu Ala Gln Phe Arg Asn Ala Phe Leu Leu Gly Cys Thr Gly Ala Trp
            260                 265                 270

Ser Leu Ala Pro Asn Gln Ile Pro Ile Ala Lys Arg Val Phe Ser Pro
        275                 280                 285

Asp Val Asn Glu Val Leu Phe Ala Lys Arg Ile Leu Glu Ala Met Pro
    290                 295                 300

Asp Gly Ser Gly Val Ala Met Ile Asp Gly Lys Met Gln Asp Asp Ala
305                 310                 315                 320

Thr Trp Lys Gln Ala Lys Val Ile Val Asp Leu Ala Arg Met Ile Ala
                325                 330                 335

Lys Lys Asp Pro Asp Leu Ala Gln Ala Tyr Gly Leu
                340                 345

<210> SEQ ID NO 22
<211> LENGTH: 352
<212> TYPE: PRT
<213> ORGANISM: Chloroflexus aurantiacus

<400> SEQUENCE: 22

Met Ser Ala Lys Thr Asn Pro Gly Asn Phe Glu Asp Phe Arg Leu
1               5                   10                  15

Gly Gln Thr Ile Val His Ala Thr Pro Arg Thr Ile Thr Glu Gly Asp
            20                  25                  30

Val Ala Leu Tyr Thr Ser Leu Tyr Gly Ser Arg Phe Ala Leu Thr Ser
        35                  40                  45

Ser Thr Pro Phe Ala Gln Ser Leu Gly Leu Glu Arg Ala Pro Ile Asp
    50                  55                  60

Ser Leu Leu Val Phe His Ile Val Phe Gly Lys Thr Val Pro Asp Ile
65                  70                  75                  80

Ser Leu Asn Ala Ile Ala Asn Leu Gly Tyr Ala Gly Gly Arg Phe Gly
                85                  90                  95

Ala Val Val Tyr Pro Gly Asp Thr Leu Ser Thr Thr Ser Lys Val Ile
            100                 105                 110

Gly Leu Arg Gln Asn Lys Asp Gly Lys Thr Gly Val Val Tyr Val His
        115                 120                 125

Ser Val Gly Val Asn Gln Trp Asp Glu Val Val Leu Glu Tyr Ile Arg
    130                 135                 140

Trp Val Met Val Arg Lys Arg Asp Pro Asn Ala Pro Ala Pro Glu Thr
145                 150                 155                 160

Val Val Pro Asp Leu Pro Asp Ser Val Pro Val Thr Asp Leu Thr Val
                165                 170                 175

Pro Tyr Thr Val Ser Ala Ala Asn Tyr Asn Leu Ala His Ala Gly Ser
            180                 185                 190

Asn Tyr Leu Trp Asp Asp Tyr Glu Val Gly Glu Lys Ile Asp His Val
        195                 200                 205

Asp Gly Val Thr Ile Glu Glu Ala Glu His Met Gln Ala Thr Arg Leu
    210                 215                 220

Tyr Gln Asn Thr Ala Arg Val His Phe Asn Leu His Val Glu Arg Glu
225                 230                 235                 240

Gly Arg Phe Gly Arg Arg Ile Val Tyr Gly Gly His Ile Ile Ser Leu
                245                 250                 255

Ala Arg Ser Leu Ser Phe Asn Gly Leu Ala Asn Ala Leu Ser Ile Ala
            260                 265                 270
```

-continued

Ala Ile Asn Ser Gly Arg His Thr Asn Pro Ser Phe Ala Gly Asp Thr
            275                 280                 285

Ile Tyr Ala Trp Ser Glu Ile Leu Ala Lys Met Ala Ile Pro Gly Arg
        290                 295                 300

Thr Asp Ile Gly Ala Leu Arg Val Arg Thr Val Ala Thr Lys Asp Arg
305                 310                 315                 320

Pro Cys His Asp Phe Pro Tyr Arg Asp Ala Glu Gly Asn Tyr Asp Pro
                325                 330                 335

Ala Val Val Leu Asp Phe Asp Tyr Thr Val Leu Met Pro Arg Arg Gly
                340                 345                 350

<210> SEQ ID NO 23
<211> LENGTH: 409
<212> TYPE: PRT
<213> ORGANISM: Chloroflexus aurantiacus

<400> SEQUENCE: 23

Met Lys Gly Ile Leu His Gly Leu Arg Val Val Glu Gly Ser Ala Phe
1               5                   10                  15

Val Ala Ala Pro Leu Gly Gly Met Thr Leu Ala Gln Leu Gly Ala Asp
            20                  25                  30

Val Ile Arg Phe Asp Pro Ile Gly Gly Leu Asp Tyr Lys Arg Trp
        35                  40                  45

Pro Val Thr Leu Asp Gly Lys His Ser Leu Phe Trp Ala Gly Leu Asn
    50                  55                  60

Lys Gly Lys Arg Ser Ile Ala Ile Asp Ile Arg His Pro Arg Gly Gln
65                  70                  75                  80

Glu Leu Leu Thr Gln Leu Ile Cys Ala Pro Gly Glu His Ala Gly Leu
                85                  90                  95

Phe Ile Thr Asn Phe Pro Ala Arg Gly Trp Leu Ser Tyr Asp Glu Leu
            100                 105                 110

Lys Arg His Arg Ala Asp Leu Ile Met Val Asn Leu Val Gly Arg Arg
        115                 120                 125

Asp Gly Gly Ser Glu Val Asp Tyr Thr Val Asn Pro Gln Leu Gly Leu
    130                 135                 140

Pro Phe Met Thr Gly Pro Val Thr Thr Pro Asp Val Val Asn His Val
145                 150                 155                 160

Leu Pro Ala Trp Asp Ile Val Thr Gly Gln Met Ile Ala Leu Gly Leu
                165                 170                 175

Leu Ala Ala Glu Arg His Arg Arg Leu Thr Gly Glu Gly Gln Leu Val
            180                 185                 190

Lys Ile Ala Leu Lys Asp Val Gly Leu Ala Met Ile Gly His Leu Gly
        195                 200                 205

Met Ile Ala Glu Val Met Ile Asn Asp Thr Arg Pro Arg Gln Gly
    210                 215                 220

Asn Tyr Leu Tyr Gly Ala Phe Gly Arg Asp Phe Glu Thr Leu Asp Gly
225                 230                 235                 240

Lys Arg Val Met Val Val Gly Leu Thr Asp Leu Gln Trp Lys Ala Leu
                245                 250                 255

Gly Lys Ala Thr Gly Leu Thr Asp Ala Phe Asn Ala Leu Gly Ala Arg
            260                 265                 270

Leu Gly Leu Asn Met Asp Glu Glu Gly Asp Arg Phe Arg Ala Arg His
        275                 280                 285

Glu Ile Ala Ala Leu Leu Glu Pro Trp Phe His Ala Arg Thr Leu Ala

```
                290                 295                 300
Glu Val Arg Arg Ile Phe Glu Gln His Arg Val Thr Trp Ala Pro Tyr
305                 310                 315                 320

Arg Thr Val Arg Glu Ala Ile Ala Gln Asp Pro Asp Cys Ser Thr Asp
                325                 330                 335

Asn Pro Met Phe Ala Met Val Glu Gln Pro Gly Ile Gly Ser Tyr Leu
            340                 345                 350

Met Pro Gly Ser Pro Leu Asp Phe Thr Ala Val Pro Arg Leu Pro Val
        355                 360                 365

Gln Pro Ala Pro Arg Leu Gly Glu His Thr Asp Glu Ile Leu Leu Glu
    370                 375                 380

Val Leu Gly Leu Ser Glu Ala Glu Val Gly Arg Leu His Asp Glu Gly
385                 390                 395                 400

Ile Val Ala Gly Pro Asp Arg Ala Ala
                405

<210> SEQ ID NO 24
<211> LENGTH: 280
<212> TYPE: PRT
<213> ORGANISM: Chloroflexus aurantiacus

<400> SEQUENCE: 24

Met Ser Ser Ala Asp Trp Met Ala Trp Ile Gly Arg Thr Glu Gln Val
1               5                   10                  15

Glu Asp Asp Ile Cys Leu Ala Gln Ala Ile Ala Ala Ala Thr Leu
            20                  25                  30

Glu Pro Pro Ser Gly Ala Pro Thr Ala Asp Ser Pro Leu Pro Pro Leu
        35                  40                  45

Trp His Trp Phe Tyr Phe Leu Pro Arg Ala Pro Gln Ser Gln Leu Ser
    50                  55                  60

Ser Asp Gly His Pro Gln Arg Gly Gly Phe Ile Pro Pro Ile Pro Tyr
65                  70                  75                  80

Pro Arg Arg Met Phe Ala Gly Ala Arg Ile Arg Phe His His Pro Leu
                85                  90                  95

Arg Ile Gly Gln Pro Ala Arg Arg Glu Gly Val Ile Arg Asn Ile Thr
            100                 105                 110

Gln Lys Ser Gly Arg Ser Gly Pro Leu Ala Phe Val Thr Val Gly Tyr
        115                 120                 125

Gln Ile Tyr Gln His Glu Met Leu Cys Ile Glu Glu Glu Gln Asp Ile
    130                 135                 140

Val Tyr Arg Glu Pro Gly Ala Pro Val Pro Ala Pro Thr Pro Val Glu
145                 150                 155                 160

Leu Pro Pro Val His Asp Ala Ile Thr Arg Thr Val Val Pro Asp Pro
                165                 170                 175

Arg Leu Leu Phe Arg Phe Ser Ala Leu Thr Phe Asn Ala His Arg Ile
            180                 185                 190

His Tyr Asp Arg Pro Tyr Ala Gln His Glu Glu Gly Tyr Pro Gly Leu
        195                 200                 205

Val Val His Gly Pro Leu Val Ala Val Leu Met Glu Leu Ala Arg
    210                 215                 220

His His Thr Ser Arg Pro Ile Val Gly Phe Ser Phe Arg Ser Gln Ala
225                 230                 235                 240

Pro Leu Phe Asp Leu Ala Pro Phe Arg Leu Leu Ala Arg Pro Asn Gly
                245                 250                 255
```

Asp Arg Ile Asp Leu Glu Ala Gln Gly Pro Asp Gly Ala Thr Ala Leu
                260                 265                 270

Ser Ala Thr Val Glu Leu Gly Gly
        275                 280

<210> SEQ ID NO 25
<211> LENGTH: 1217
<212> TYPE: PRT
<213> ORGANISM: Erythrobacter sp.

<400> SEQUENCE: 25

Met Ser Lys Glu Gly Asn Ala Ala Lys Gly Arg Leu Glu Gly Lys Val
1               5                   10                  15

Ala Leu Ile Thr Gly Ala Ala Gly Asn Leu Gly Asn Glu Ile Ser Arg
            20                  25                  30

Ala Phe Ala Arg Glu Gly Ala Phe Val Val Met Thr Gly Arg Thr Glu
        35                  40                  45

Glu Arg Ile Ser Ala Ala Arg Glu Gln Leu Ile Ala Asp Thr Gly Val
    50                  55                  60

Ala Pro Glu Arg Ile Asp Thr Ala Val Leu Asp Gly Gly Asn Pro Asp
65                  70                  75                  80

Ser Ile Arg Ala Ala Met Ala Lys Leu Arg Lys Glu Tyr Gly Arg Ile
                85                  90                  95

Asp Ile Leu Ile Asn Asn Ala Gly Ser Ala Gly Pro Lys Gln Pro Leu
            100                 105                 110

His Asn Val Pro Leu Ser Pro Gln Glu Met Glu Ala Cys Gly Asp Thr
        115                 120                 125

Glu Thr Val Arg Asp Ala Met Leu Asn Ile Leu Gly Val Thr Trp Asn
    130                 135                 140

Met Ala Arg Ile Val Ala Pro Met Met Pro Val Gly Gly Ala Met Val
145                 150                 155                 160

Asn Ile Ser Thr Ile Phe Ser His Thr Arg Tyr Tyr Gly Arg Thr Ala
                165                 170                 175

Tyr Val Val Pro Lys Ala Ala Leu Asn Ala Leu Ser Asn Gln Leu Ala
            180                 185                 190

Ser Glu Leu Gly Pro Arg Gly Ile Arg Val Asn Thr Val Phe Pro Gly
        195                 200                 205

Pro Ile Glu Ser Asp Arg Ile Arg Thr Val Phe Ala Ala Met Asp Glu
    210                 215                 220

Val Gln Ser Gln Pro Lys Asp Thr Thr Ala Asn Tyr Phe Thr Gly Arg
225                 230                 235                 240

Met Ala Leu Thr Arg Ser Val Asn Gly Lys Val Asp Gly Lys Pro Leu
                245                 250                 255

Pro Asn Pro Lys Asp Ile Ala Gly Thr Cys Leu Phe Leu Ala Ser Glu
            260                 265                 270

Glu Ala Ala Gly Ile Ala Gly Glu Val Asp Val Thr His Gly Leu
        275                 280                 285

Ser Ala Asn Arg Thr Ser Ala Ser Thr Tyr Met Thr Arg Pro Ser Met
    290                 295                 300

Arg Ser Leu Asp Gly Ala Gly Leu Asn Ile Phe Ile Val Ser Gly Glu
305                 310                 315                 320

Asn Trp Asp Asp Ala Leu Val Ala Ala His Thr Leu Ile Gly Ser Gly
                325                 330                 335

Ala Lys Val Arg Leu Gly Leu Ala Arg Asn Ala Asp Val Ala Gln Ala
            340                 345                 350

```
Asn Ala Arg Leu Lys Ala Gln Gly Ile Gly Glu Glu Leu Thr Val Thr
        355                 360                 365

Arg Phe Asn Arg Ala Glu Pro Asp Ala Met Glu Asp Ala Leu Ala Ala
        370                 375                 380

Phe Ser Gly Asp Val Asp Gly Ala Ile Thr Gly Ala Ile Ile Leu Pro
385                 390                 395                 400

Val Lys Pro Ser Gly His Phe Thr Gly Ser Leu Leu Ala Ala Asp Asp
                405                 410                 415

Asp Thr Val Thr Lys Phe Met Asp Thr Glu Leu Val Gly Ala Ile Ala
                420                 425                 430

Val Ser Arg Ser Leu Ala Arg Tyr Trp His Gly Arg Glu Asp Leu Gln
        435                 440                 445

Ser Pro Pro Arg Cys Val Phe Met Thr Asn Pro Gly Asp Pro Leu Gly
        450                 455                 460

Asn Ser Phe Ala Ser Val Leu Ser Ala Gly Ile Thr Gln Leu Ile Arg
465                 470                 475                 480

Ile Trp Arg Asp Glu Glu Arg Val Gln Ala Gly Asn Gly Ser Thr Glu
                485                 490                 495

His Ala Val Trp Ser Asn Gln Ile Val Arg His Thr Asn Thr Glu Asp
        500                 505                 510

Glu Asn Thr Arg Phe Ala Ser Gly His Ala Thr Arg Val Leu Phe Arg
        515                 520                 525

Glu Gln His Ile Ala Glu Ile Asp Leu Lys Leu Pro Ala Asn Ile Ser
        530                 535                 540

Glu Glu Thr Gly Ser Arg Lys Ala Met Val Gly Phe Ala Glu Asn Ile
545                 550                 555                 560

Thr Gly Leu His Leu Gly Lys Val Ala Phe Ile Thr Gly Gly Ser Ala
                565                 570                 575

Gly Ile Gly Gly Gln Val Ala Arg Leu Leu Ala Leu Ala Gly Ala Lys
                580                 585                 590

Val Met Met Val Ala Arg Arg Glu Ser Glu Leu Val Ala Ala Arg Asp
        595                 600                 605

Arg Ile Val Gly Glu Leu Gln Asp Ile Gly Phe Ala Gly Val Glu Arg
        610                 615                 620

Arg Val Lys Tyr Met Ala Asp Ile Asp Val Ser Asp Phe Ala Ser Leu
625                 630                 635                 640

Asp Lys Ala Val Asp Ala Thr Leu Glu Glu Phe Gly Arg Ile Asp Tyr
                645                 650                 655

Leu Ile Asn Asn Ala Gly Val Ala Gly Ala Glu Asp Met Val Ile Asp
                660                 665                 670

Met Glu Pro Glu Ala Trp Arg Phe Thr Leu Asp Ala Asn Leu Ile Ser
        675                 680                 685

Asn Tyr His Leu Met Gln Arg Val Val Pro Leu Met Lys Glu Gln Gly
        690                 695                 700

Ser Gly Tyr Val Leu Asn Val Ser Ser Tyr Phe Gly Gly Glu Lys Phe
705                 710                 715                 720

Leu Ala Val Ala Tyr Pro Asn Arg Ala Asp Tyr Gly Leu Ser Lys Ala
                725                 730                 735

Gly Gln Arg Ala Met Val Glu Ala Phe Ser Pro Phe Leu Gly Pro Glu
                740                 745                 750

Val Gln Cys Asn Ala Ile Ala Pro Gly Pro Val Asp Gly Asp Arg Leu
        755                 760                 765
```

```
Ser Gly Thr Gly Gly Lys Pro Gly Leu Phe Gln Arg Arg Ala Lys Leu
770                 775                 780
Ile Leu Glu Asn Lys Arg Leu Asn Ala Val Tyr Ser Ala Val Ile His
785                 790                 795                 800
Ala Ile Arg Glu Gly Gly Asp Ala Ala Lys Ile Leu Thr Arg Leu Ser
                805                 810                 815
Arg Asn Ser Thr Ser Thr Leu Ser His Asp Ala Glu Ala Pro Glu Glu
            820                 825                 830
Leu Arg Lys Leu Ala Leu Asp Phe Ala Ser Gln Gly Asp Gly Leu Cys
                835                 840                 845
Thr Trp Asp Gln Tyr Leu Leu Thr Asp Ala Met Ala Gln Arg Leu Leu
850                 855                 860
Val Arg Leu Gln Leu Gly Gly Phe Leu Leu Gly Ser Asn Glu Trp Ala
865                 870                 875                 880
Ser Leu Ser Ser Ser Glu Gln Thr Trp Leu Lys Leu Ser Pro Pro Asp
                885                 890                 895
Asp Lys Pro Phe Leu Pro Ala Ala Gln Val Asp Lys Val Ala Asn Gly
            900                 905                 910
Val Gly Lys Gly Val Ile Ser Gln Leu His Leu Gly Ala Met Pro Thr
            915                 920                 925
Glu Ala Glu Val Ala Gln Ala Thr Val Phe Phe Leu Ala Asp Arg Ala
930                 935                 940
Val Ser Gly Glu Thr Phe Met Pro Ser Gly Gly Leu Arg Val Glu Arg
945                 950                 955                 960
Ser Asn Thr Glu Arg Glu Met Phe Gly Ser Pro Lys Gln Glu Arg Ile
                965                 970                 975
Asp Lys Met Lys Gly Lys Thr Val Trp Ile Ile Gly Glu His Leu Ser
            980                 985                 990
Asp Tyr Val Ala Ala Thr Ile Glu Glu Leu Val Ser Gly Cys Gly Val
            995                 1000                1005
Ala Lys Val Val Leu Ile Ala Lys Asp Lys Ser Gly Glu Lys Ala
        1010                1015                1020
Val Arg Asp Gln Leu Pro Asn Asp Leu Ser Lys Asp Ala Leu Glu
        1025                1030                1035
Val Leu Ile Ala Gly Asp Gly Leu Glu Glu Ala Met Asp Glu Ala
        1040                1045                1050
Leu Gly His Trp Gly Lys Pro Thr Thr Val Leu Ser Met Pro Gly
        1055                1060                1065
Glu Pro Leu Pro Asp His Leu Phe Glu Gly Gly Asn Pro Leu Ser
        1070                1075                1080
Thr Lys Asp Phe Ala His Met Val Glu Ala Asn Ile Thr Arg His
        1085                1090                1095
Tyr Arg Val Thr Arg Lys Ala Ser Leu Tyr Asp Gly Cys Gln Val
        1100                1105                1110
Val Leu Val Ser Pro Asp Val Pro Tyr Gly Ser Asp Gly Pro Gly
        1115                1120                1125
Val Ala Leu Ala Asn Phe Val Lys Thr Ser Leu His Ala Phe Thr
        1130                1135                1140
Ala Thr Val Ala Val Glu Asn Glu Arg Leu Val His Asp Val Pro
        1145                1150                1155
Val Asn Gln Ile Asn Leu Thr Arg Arg Val Ser Ser Glu Glu Pro
        1160                1165                1170
Arg Asp Ala Asp Glu His Ala Glu Glu Leu Arg Arg Phe Thr Arg
```

<210> SEQ ID NO 26
<211> LENGTH: 1850
<212> TYPE: PRT
<213> ORGANISM: Erythrobacter sp.

<400> SEQUENCE: 26

```
Ala Val Leu Leu Val Gly Ala Pro Leu Pro Asp Ala Gln Asp Ser
            1190                1195                1200
Arg Tyr Arg Ser Lys Ile Tyr Arg Gly Thr Ser Met Thr Val
        1205                1210                1215

Met Ile Gly Glu Gly Asp Asp Ile Gly Ser Ser Asn Asn Leu Glu Lys
  1               5                  10                  15
Gln Ser His Gly Leu Arg Ile Ser Asp Arg Asp His Phe Gln Arg Leu
                 20                  25                  30
Arg Glu Glu Cys Arg Ser Asp Pro Gly Glu Phe His Gly Arg Leu Ala
             35                  40                  45
Lys Arg Glu Ile Cys Trp Leu Ile Glu Gly Pro Gly Asn Pro Ala
         50                  55                  60
Trp Ala Phe Tyr Asp Asp Ala Glu Thr Trp Thr Gly Trp Asp Ala
 65                  70                  75                  80
Ser Ser Ala Ala Pro Ile Thr Leu Asp Leu Pro Glu Ser Phe Glu Pro
                 85                  90                  95
Trp Glu Arg Ala Phe Asn Asp Asp Pro Pro Asn Trp Arg Trp Phe
            100                 105                 110
Glu Gly Gly Leu Thr Ser Thr Ala Phe Asn Glu Val Asp Arg His Val
            115                 120                 125
Leu Ser Gly His Gly Asp Glu Ala Ala Met Ile Phe Glu Gly Asp Arg
        130                 135                 140
Trp Asn Met Ala Ser Glu Gly Arg Gly Gly Pro Val Asp Ser Glu
145                 150                 155                 160
Val Ile Ser Arg Arg Lys Leu Leu Leu Glu Ser Ala Lys Cys Ala Leu
                165                 170                 175
Ala Leu Lys Ala Leu Gly Leu Glu Ala Gly Asp Arg Ile Ala Leu Asn
            180                 185                 190
Met Pro Ser Ile Pro Glu Gln Ile Tyr Trp Thr Glu Gly Ala Lys Arg
        195                 200                 205
Met Gly Ile Val Tyr Thr Pro Val Phe Gly Gly Phe Ser Asp Lys Thr
    210                 215                 220
Leu Ser Asp Arg Ile Ala Asp Ala Gly Ala Arg Val Val Val Thr Ala
225                 230                 235                 240
Asp Gly Ser Tyr Arg Asn Ala Gln Met Val Pro Phe Lys Pro Ser Tyr
                245                 250                 255
Thr Asp Pro Ala Leu Asp Asn Phe Ile Ala Val Pro Val Ala Met Glu
            260                 265                 270
Leu Leu Gly Gln Ala Leu Glu Asp Gly Glu Leu Val Val Ala Pro Glu
        275                 280                 285
His Ala Gly Leu Ile Arg Ser Glu Val Ala Gly Leu Leu Asp Gly Glu
    290                 295                 300
Val Thr Val Glu Arg Ser Asp Val Met Arg Gly Val Gly Lys Ala Leu
305                 310                 315                 320
Thr Ala Ile Ala Ser Gly Glu Ala Gly Gly Ala Met Thr Pro Arg
                325                 330                 335
```

-continued

```
Gln Ala Ala Gln Leu Arg Ile Ala Ile Ala Ser Ala Leu Val Asp Ser
            340                 345                 350

Pro Pro Arg Val Asp Ala Val Val Val Lys His Thr Ala Gln Pro
        355                 360                 365

Asp Leu Pro Trp Asn Glu Ala Arg Asp His Trp Ser His Asp Leu Thr
    370                 375                 380

Ala Ala Ala Gly Glu Glu Leu Leu Lys Ala Ala Arg Asp Ala Gly Phe
385                 390                 395                 400

Asp Val Ala Asp Glu Glu Ala Leu Leu Ala Leu Ser Asp Thr Glu Phe
                405                 410                 415

Val Arg Ala Ile Trp Ala Gly Ala Pro Val Leu Ala Val Asp Ala Glu
        420                 425                 430

Tyr Pro Asn Phe Ile Ile Tyr Thr Ser Gly Ser Thr Gly Lys Pro Lys
    435                 440                 445

Gly Val Val His Val His Gly Gly Tyr Ala Ser Gly Val Ala Ala Thr
    450                 455                 460

Met Pro Ala Ala Phe Gly Ala Glu Pro Gly Asp Val Met Tyr Val Val
465                 470                 475                 480

Ala Asp Pro Gly Trp Ile Thr Gly Gln Ser Tyr Gln Ile Ala Ala Ser
                485                 490                 495

Leu Leu Ser Arg Val Thr Thr Val Ile Thr Glu Gly Ser Pro Val Phe
            500                 505                 510

Pro His Ala Gly Arg Phe Ala Ser Ile Ile Glu Arg Tyr Gly Val Asn
        515                 520                 525

Val Phe Lys Ala Gly Val Thr Phe Leu Lys Ser Val Met Gln Asn Pro
    530                 535                 540

Glu Asn Leu Lys Asp Ile Gln Arg Tyr Asp Leu Ser Ser Leu Lys Val
545                 550                 555                 560

Ala Thr Phe Cys Ala Glu Pro Val Ser Pro Ala Val Gln Ala Phe Ala
                565                 570                 575

Met Glu His Ile Thr His Arg Tyr Ile Asn Ser Tyr Trp Ala Thr Glu
            580                 585                 590

His Gly Gly Met Val Trp Thr His Phe Ala Asp Ala Asp Gly Phe Pro
        595                 600                 605

Leu Glu Ala Asp Ala His Thr Tyr Pro Leu Pro Trp Ile Met Gly Asp
    610                 615                 620

Val Trp Val Glu Asp Ala Asp Gly Ser Ser Asn Gly Pro Val Glu Tyr
625                 630                 635                 640

Glu Arg Asp Thr Gly Thr Gly Gly Ala Pro Trp Arg Val Ala Glu Asp
                645                 650                 655

Gly Glu Lys Gly Glu Ile Val Ile Ala Leu Pro Tyr Pro Tyr Leu Thr
            660                 665                 670

Arg Thr Ile Trp Gly Asp Val Glu Asn Phe Thr Val Glu His Val Gly
        675                 680                 685

Asn Leu Ala Arg Val Ala Gly Gly Trp Arg Gly Asp Glu Val Arg Tyr
    690                 695                 700

Ala Asp Thr Tyr Trp Arg Arg Trp Lys Gly Ala Trp Ala Tyr Thr Gln
705                 710                 715                 720

Gly Asp Phe Ala Met Arg His Pro Asp Gly Ser Phe Ser Leu His Gly
                725                 730                 735

Arg Ser Asp Asp Val Ile Asn Val Ser Gly His Arg Ile Gly Thr Glu
            740                 745                 750

Glu Ile Glu Gly Ala Ile Leu Arg Asp Lys Ala Leu Asp Pro Asn Ser
```

```
              755                 760                 765
Pro Val Gly Asn Val Ile Val Ile Gly Ala Pro His Ser Gln Lys Gly
770                 775                 780

Val Thr Pro Ile Ala Phe Val Thr Pro Val Glu Gly Arg Arg Leu Thr
785                 790                 795                 800

Gln Asp Asp Lys Arg Arg Leu Thr Asp Leu Val Arg Thr Glu Lys Gly
                    805                 810                 815

Ala Val Ala Val Pro Gln Asp Phe Ile Glu Leu Ser Glu Phe Pro Glu
            820                 825                 830

Thr Arg Ser Gly Lys Tyr Met Arg Arg Met Val Arg Ala Val Val Glu
                835                 840                 845

Gly Gly Glu Val Gly Asp Ala Ser Thr Leu Arg Asn Pro Glu Ser Leu
850                 855                 860

Asp Glu Leu Ala Arg Ala Val Asp Gly Trp Lys Arg Arg Gln Ser Leu
865                 870                 875                 880

Ser Asp Thr Gln Ala Leu Phe Glu Arg Tyr Arg Phe Phe Thr Ile Gln
                885                 890                 895

Tyr Asn Leu Val Ala Pro Gly Lys Arg Val Ala Thr Val Thr Val Lys
            900                 905                 910

Asn Pro Pro Val Asn Ala Leu Asn Glu Arg Ala Leu Asp Glu Leu Val
            915                 920                 925

Ile Ile Ala Glu His Leu Ala Arg Lys Asp Asp Val Ala Ala Val Val
930                 935                 940

Phe Thr Gly Ser Gly Thr Ala Ser Phe Val Ala Gly Ala Asp Ile Arg
945                 950                 955                 960

Gln Met Leu Glu Glu Val Asn Ser Val Glu Glu Ala Lys Ala Leu Pro
                965                 970                 975

Asp Asn Ala Gln Leu Ala Phe Arg Thr Ile Glu Met Asp Lys Pro
            980                 985                 990

Cys Ile Ala Ala Ile Gln Gly Val  Ala Leu Gly Gly Gly  Met Glu Phe
            995                 1000                1005

Ala Leu Ala Cys His Tyr Arg  Val Ala Glu Pro Lys  Ala Arg Phe
            1010                1015                1020

Gly Gln  Pro Glu Ile Asn Leu  Arg Leu Leu Pro Gly  Tyr Gly Gly
            1025                1030                1035

Thr Gln  Arg Leu Pro Arg Leu  Leu Ala Asp Gly Gly  Gly Glu Thr
            1040                1045                1050

Gly Leu  Arg Asp Ala Leu Asp  Leu Ile Leu Gly Gly  Arg Ala Ile
            1055                1060                1065

Asp Ala  Asp Ala Ala Leu Ala  Val Gly Ala Val Asp  Ala Leu Ala
            1070                1075                1080

Asp Gly  Ser Asp Asn Ala Leu  Ser His Ala His Ala  Met Val Arg
            1085                1090                1095

Glu Phe  Val Arg Ser Gly Asp  Asp Ser Ala Leu Gly  Lys Ala Phe
            1100                1105                1110

Ala Ala  Arg Lys Thr Gln Thr  Gln Ser Trp His Glu  Pro Ala Ser
            1115                1120                1125

Ile Asp  Leu Asp Ala Val Leu  Glu Asp Glu Phe Leu  Gln Arg Ile
            1130                1135                1140

Leu Asn  Gln Leu Glu Trp Ala  Gly Arg Asp Lys Ala  Gly Glu Arg
            1145                1150                1155

Ala Leu  Asp Ala Val Arg Thr  Gly Trp Thr Gln Gly  Met Thr Ala
            1160                1165                1170
```

```
Gly Leu Glu Cys Glu Ala Gln Arg Phe Ala Glu Ala Ile Ile Asp
    1175            1180                1185

Pro Glu Gly Gly Lys Thr Gly Ile Gln Gln Phe Met Asp Lys Gln
    1190            1195                1200

Ser Pro Pro Leu Pro Val Arg Arg Asp Gly Val Trp Glu Asp Asp
    1205            1210                1215

Gln His Glu Ala Thr Lys Thr Ala Leu Ile Glu Ala Gly Asp Leu
    1220            1225                1230

Leu Pro Leu Gly Ala Pro Phe Tyr Pro Gly Val Thr Ala Ile Pro
    1235            1240                1245

Pro Lys Gln Leu Ala Phe Gly Ile Ala Arg Asp Pro Asp Thr Gly
    1250            1255                1260

Ala Pro Arg Phe Gly Pro Pro Glu Thr His Glu Arg Glu Leu Val
    1265            1270                1275

Val Asn Thr Pro Lys Pro Gly Ala Asn Glu Ala Leu Ile Tyr Leu
    1280            1285                1290

Leu Ser Ser Glu Val Asn Phe Asn Asp Ile Trp Ala Leu Thr Gly
    1295            1300                1305

Ile Pro Val Ser Pro Phe Asp Ala His Asp Glu Asp Val Gln Ile
    1310            1315                1320

Thr Gly Ser Gly Gly Leu Ala Leu Val Ala Ala Leu Gly Ser Glu
    1325            1330                1335

Leu Lys Glu Glu Gly Arg Leu Gln Val Gly Asp Leu Val Ser Val
    1340            1345                1350

Tyr Ser Gly Thr Ser Glu Leu Leu Ser Pro Leu Ala Gly Asp Asp
    1355            1360                1365

Pro Met Tyr Ala Gly Phe Ala Ile Gln Gly Tyr Glu Thr Lys Thr
    1370            1375                1380

Gly Ser His Ala Gln Phe Leu Thr Val Gln Gly Pro Gln Leu His
    1385            1390                1395

Arg Pro Pro Ala Asp Leu Thr Leu Glu Gln Ala Gly Ala Tyr Thr
    1400            1405                1410

Leu Asn Leu Gly Thr Val Ala Arg Cys Leu Phe Thr Thr Leu Glu
    1415            1420                1425

Ile Gln Ala Gly Lys Thr Ala Phe Val Glu Gly Ser Ala Thr Gly
    1430            1435                1440

Thr Gly Leu Asp Ala Leu Lys Ser Ser Val Arg Thr Gly Leu Ala
    1445            1450                1455

Val Thr Gly Leu Val Ser Ser Glu Asp Arg Ala Glu Phe Val Lys
    1460            1465                1470

Ser His Gly Ser Val Gly Ala Ile Asn Arg Lys Asp Pro Glu Ile
    1475            1480                1485

Ala Asp Cys Phe Thr Pro Val Pro Asp Asp Pro Asp Glu Ala Arg
    1490            1495                1500

Gln Trp Glu Ala Asp Gly Glu Lys Leu Leu Asp Ala Tyr Arg Glu
    1505            1510                1515

Thr Asn Gly Gly Lys Leu Ala Asp Tyr Val Val Ser His Ala Gly
    1520            1525                1530

Glu Arg Ala Phe Pro Arg Ser Phe Gln Leu Leu Ala Glu Gly Gly
    1535            1540                1545

Arg Leu Ala Phe Tyr Gly Ala Ser Ser Gly Tyr His Phe Ser Phe
    1550            1555                1560
```

```
Met Gly Lys Gly Gly Glu Ala Arg Pro Asp Glu Met Leu Ala Arg
    1565                1570                1575

Ala Asn Leu Arg Gly Gly Glu Ser Val Leu Leu Tyr Tyr Gly Pro
    1580                1585                1590

Gly Ser His Glu Leu Ala Asp Glu Lys Gly Leu Glu Met Val Glu
    1595                1600                1605

Ala Ala Arg Leu Met Lys Ala Arg Met Val Ile Val Thr Thr Ser
    1610                1615                1620

Asp Gly Gln Arg Glu Phe Leu Gln Ser Leu Gly Leu Glu Asp Ala
    1625                1630                1635

Val Glu Gly Ile Val Ser Ile Glu Gly Leu Lys Arg Arg Leu Ser
    1640                1645                1650

Asp Phe His Trp Pro Asp Thr Leu Pro Arg Leu Pro Asp Ala Arg
    1655                1660                1665

Thr Asp Ile Glu Asn Phe Lys Ile Gly Val Arg Ala Tyr Gln Gln
    1670                1675                1680

Asn Thr Met Lys Pro Phe Gly Thr Ala Val Gly Lys Leu Leu Arg
    1685                1690                1695

Ser Pro Gly Asn Pro Arg Gly Val Pro Asp Leu Val Ile Glu Arg
    1700                1705                1710

Ala Gly Gln Asp Thr Leu Gly Val Ser Thr Ser Leu Val Lys Pro
    1715                1720                1725

Phe Gly Gly Arg Val Ile Tyr Ala Glu Glu Met Ala Gly Arg Arg
    1730                1735                1740

Tyr Thr Phe Tyr Ala Pro Gln Val Trp Thr Arg Gln Arg Arg Ile
    1745                1750                1755

Tyr Met Pro Ser Ala Glu Ile Phe Gly Thr His Leu Cys Asn Ala
    1760                1765                1770

Tyr Glu Val Thr Met Met Asn Glu Met Val Ala Ala Gly Leu Leu
    1775                1780                1785

Asp Val Thr Glu Pro Thr Met Val Pro Trp Glu Gly Leu Pro Glu
    1790                1795                1800

Ala His Gln Ala Met Trp Asp Asn Arg His Ser Gly Ala Thr Tyr
    1805                1810                1815

Val Val Asn His Ala Leu Pro Ala Met Gly Leu Thr Thr Lys Asp
    1820                1825                1830

Glu Leu Leu Glu Tyr Trp Val Ala Ala Gln Ser Asp Thr Gly Glu
    1835                1840                1845

Thr Ser
    1850

<210> SEQ ID NO 27
<211> LENGTH: 351
<212> TYPE: PRT
<213> ORGANISM: Candidatus Accumulibacter phosphatis

<400> SEQUENCE: 27

Met Lys Leu Pro Val His Phe Tyr Lys Pro Leu Ala Ile Gly Ala Pro
1               5                   10                  15

Gln Pro Leu Arg Glu Leu Pro Val Arg Pro Glu Arg Met Ile His Phe
                20                  25                  30

Phe Pro Pro His Ile Asp Lys Ile Arg Ala Lys Ala Pro Glu Thr Ala
            35                  40                  45

Arg Gln Cys Asp Val Met Cys Gly Asn Leu Glu Asp Ala Ile Pro Ile
        50                  55                  60
```

Glu Ala Lys Asp Ala Ala Arg Ala Gly Phe Ile Asp Leu Ala Ala
65                  70                  75                  80

His Asp Phe Gly Asp Thr Ala Met Trp Val Arg Val Asn Ala Leu Asn
            85                  90                  95

Ser Pro Trp Val Leu Asp Asp Leu Asn Glu Ile Ile Lys His Val Gly
            100                 105                 110

Asn Lys Val Asp Val Ile Met Ile Pro Lys Val Glu Gly Pro Trp Asp
            115                 120                 125

Ile His Phe Val Asp Gln Tyr Val Ser Leu Leu Glu Ala Lys Tyr Ala
            130                 135                 140

Ile Arg Lys Pro Ile Leu Leu His Ala Leu Leu Glu Thr Ala Gln Gly
145                 150                 155                 160

Val Thr Asn Val Glu Ala Ile Cys Gly Ala Ser Pro Arg Met His Gly
                165                 170                 175

Leu Ser Leu Gly Pro Ala Asp Leu Ala Ala Ser Arg Gly Met Lys Thr
                180                 185                 190

Thr Arg Val Gly Gly His Pro Gly Tyr Gly Val Leu Ala Asp Pro
            195                 200                 205

Glu Ala Gly Gln Asp Gly Gly Glu Lys Gln Arg Ala Phe Phe Gln Gln
210                 215                 220

Asp Leu Trp His Tyr Thr Val Ala Arg Met Val Asp Ala Ala Val Ala
225                 230                 235                 240

His Gly Leu Arg Ser Phe Tyr Gly Pro Phe Gly Asp Leu Lys Asp Glu
                245                 250                 255

Ala Ala Cys Glu Ala Gln Phe Arg Asn Ala Phe Leu Met Gly Cys Ser
                260                 265                 270

Gly Ala Trp Ser Leu Ala Pro Asn Gln Ile Ala Ile Ala Lys Arg Val
                275                 280                 285

Phe Ser Pro Asp Val Lys Glu Val Leu Phe Ala Lys Arg Ile Leu Glu
290                 295                 300

Ala Met Pro Asp Gly Ser Gly Val Ala Thr Ile Asp Gly Lys Met Gln
305                 310                 315                 320

Asp Asp Ala Thr Trp Lys Gln Ala Lys Val Ile Val Asp Leu Ala Arg
                325                 330                 335

Leu Val Ala Arg Arg Asp Pro Glu Leu Ala Ala Tyr Gly Trp
                340                 345                 350

<210> SEQ ID NO 28
<211> LENGTH: 352
<212> TYPE: PRT
<213> ORGANISM: Candidatus Accumulibacter phosphatis

<400> SEQUENCE: 28

Met Ser Glu Lys Thr Arg Leu Gly Asn Phe Phe Glu Asp Phe Gln Ile
1               5                   10                  15

Gly Gln Thr Ile Ala His Ala Thr Pro Arg Thr Ile Ser Glu Gly Asp
                20                  25                  30

Val Ala Leu Tyr Thr Ala Leu Thr Gly Ser Arg Phe Ala Ile Thr Ser
            35                  40                  45

Ser Asp Thr Phe Ala Tyr Ser Leu Gly Phe Pro Arg Ala Pro Val Asp
            50                  55                  60

Asn Leu Leu Ala Phe Asn Val Val Phe Gly Lys Thr Val Pro Asp Ile
65                  70                  75                  80

Ser Leu Asn Ala Val Ala Asn Leu Gly Tyr Ala Ala Gly Arg Phe Gly

```
            85                  90                  95
His Arg Val Phe Val Gly Asp Thr Leu Thr Ala Asp Ser Thr Val Ile
            100                 105                 110

Gly Leu Lys Glu Asn Arg Asp Gly Gln Thr Gly Ile Val Tyr Val Arg
            115                 120                 125

Ser Cys Gly Ile Asn Gln His Gln Gln Ile Ala Leu Asp Tyr Cys Arg
    130                 135                 140

Trp Val Met Val Arg Lys Arg Glu Pro Lys Ser Pro Ala Pro Pro Ala
145                 150                 155                 160

Cys Val Pro Asp Leu Pro Glu Ala Val Ala Ala Gly Asp Leu Ile Val
                165                 170                 175

Pro Ala Gly Ile Arg Val Asp Gln Tyr Asp Cys Thr Leu Ser Gly Asn
            180                 185                 190

Pro Asp Leu Trp Asp Asp Tyr Glu Val Gly Glu Arg Ile Asp His Val
            195                 200                 205

Asp Gly Met Thr Ile Glu Glu Ser Glu His Met Met Ala Thr Arg Leu
    210                 215                 220

Tyr Gln Asn Thr Ala Arg Val His Phe Asn Gln Gln Ala Glu Ser Ala
225                 230                 235                 240

Gly Arg Phe Gly Arg Arg Ile Ile Tyr Gly Gly Cys Ile Ile Ser Leu
                245                 250                 255

Ala Arg Ser Leu Ser Phe Asn Gly Leu Ala Asn Ala Phe Leu Val Ala
            260                 265                 270

Ala Ile Asn Gly Gly Arg His Val Thr Pro Thr Phe Ala Gly Asp Thr
            275                 280                 285

Ile Tyr Ala Trp Ser Glu Val Val Asp Lys Met Val Leu Pro Gly Arg
    290                 295                 300

Asn Asp Leu Gly Ala Leu Arg Leu Arg Thr Val Ala Thr Lys Asp Arg
305                 310                 315                 320

Pro Cys Ala Asp Phe Pro Cys Lys Thr Ala Asp Gly Ser Tyr Asp Pro
                325                 330                 335

Ser Val Val Leu Asp Phe Asp Tyr Thr Thr Leu Ile Pro Arg Arg Ala
            340                 345                 350

<210> SEQ ID NO 29
<211> LENGTH: 406
<212> TYPE: PRT
<213> ORGANISM: Candidatus Accumulibacter phosphatis

<400> SEQUENCE: 29

Met Asp Gly Ile Leu Lys Gly Leu Arg Val Glu Gly Ser Ala Phe
1               5                   10                  15

Val Ala Ala Pro Leu Gly Gly Met Thr Leu Ala Gln Leu Gly Ala Asp
                20                  25                  30

Val Ile Arg Phe Asp Pro Ile Gly Gly Leu Asp Tyr Arg Arg Trp
            35                  40                  45

Pro Leu Thr Leu Asp Gly Arg His Ser Leu Phe Trp Ala Gly Leu Asn
            50                  55                  60

Lys Gly Lys Arg Ser Ile Ala Val Asp Leu Arg Leu Pro Arg Gly Gln
65                  70                  75                  80

Glu Leu Leu Thr Gln Leu Ile Cys Ala Pro Gly Asp His Ala Gly Leu
                85                  90                  95

Phe Ser Thr Asn Phe Pro Ala Lys Gly Trp Leu Ala Tyr Glu Ala Leu
            100                 105                 110
```

-continued

```
Gln Ala His Arg Gln Asp Leu Ile Met Val Asn Leu Thr Gly Arg Arg
            115                 120                 125

Asp Gly Gly Ser Glu Val Asp Tyr Thr Leu Asn Pro Gln Leu Gly Leu
        130                 135                 140

Pro Leu Met Thr Gly Pro Thr Ser Ser Pro Glu Val Val Asn His Val
145                 150                 155                 160

Phe Pro Ala Trp Asp Phe Ile Ser Gly Gln Met Ile Ala Leu Gly Leu
                165                 170                 175

Leu Ala Ala Glu Arg His Arg Arg Leu Thr Gly Glu Gly Gln Leu Val
            180                 185                 190

Arg Leu Ala Leu Lys Asp Val Ala Leu Ala Met Leu Gly Asn Phe Gly
        195                 200                 205

Met Leu Ala Glu Ala Met Val Asn Gly Ala Asp Arg Pro Arg Gln Gly
210                 215                 220

Asn Tyr Leu Tyr Gly Ala Phe Gly Arg Asp Phe Gly Thr Leu Asp Gly
225                 230                 235                 240

Arg Arg Leu Met Val Val Gly Leu Thr Gly Met Gln Trp Arg Arg Leu
                245                 250                 255

Val Lys Ala Thr Gly Leu Arg Glu Pro Ile Ser Glu Leu Ala Ala Arg
            260                 265                 270

Leu Gly Leu Asp Phe Asp Asp Glu Gly Asn Arg Tyr Arg Ala Arg Gln
        275                 280                 285

Glu Ile Ala Arg Leu Phe Glu Pro Trp Phe His Ala Arg Thr Leu Ala
290                 295                 300

Glu Ala Ala Leu Thr Leu Asp Ala His Gly Val Thr Trp Gly Pro Tyr
305                 310                 315                 320

Arg Ser Val Arg Glu Glu Val Ala Ala Asp Pro Asp Cys Ser Thr Asp
                325                 330                 335

Asn Pro Met Phe Thr Leu Thr Glu Gln Pro Gly Ile Gly Arg Tyr Leu
            340                 345                 350

Met Pro Ser Thr Pro Leu Asp Phe Ala Gly Val Pro Arg Leu Pro Ala
        355                 360                 365

Met Pro Ala Pro Arg Leu Gly Glu His Thr Asp Gln Ile Leu Leu Asp
370                 375                 380

Ile Leu Gly Leu Ser Glu Ala Glu Val Gly Arg Leu His Asp Ala Arg
385                 390                 395                 400

Val Val Ala Gly Pro Thr
                405

<210> SEQ ID NO 30
<211> LENGTH: 284
<212> TYPE: PRT
<213> ORGANISM: Candidatus Accumulibacter phosphatis

<400> SEQUENCE: 30

Met Thr Glu Ser Arg Ile Pro Tyr Thr Gln Trp Ile Gly Arg His Glu
1               5                   10                  15

Ile Thr Asp Asp Asp Leu Gly Leu Ala Pro Ala Leu Ala Ala Ala Ala
            20                  25                  30

Thr Phe Asp Asp Thr Val Thr Pro Leu Gly Asn Gly Ser Ala Leu Pro
        35                  40                  45

Pro Leu Trp His Trp Phe Tyr Phe Leu Pro Lys Thr Pro Gln Ala Leu
    50                  55                  60

Leu Gly Val Asp Gly His Pro Gln Arg Gly Phe Met Pro Pro Ile
65                  70                  75                  80
```

Pro Tyr Pro Arg Arg Met Phe Ala Gly Ala Arg Leu Arg Phe His Arg
                85                  90                  95

Pro Leu Ile Ile Gly Gln Pro Ala Arg Arg Glu Ala Val Ile Arg Asp
            100                 105                 110

Ile Lys Glu Lys Ser Gly Arg Ser Gly Ser Leu Ala Phe Val Ser Val
        115                 120                 125

Leu Cys Arg Phe Tyr Gln Asp Gly Ala Leu Cys Ile Glu Glu Glu Gln
    130                 135                 140

Asp Ile Val Tyr Arg Glu Pro Gly Pro Ala Val Ala Cys Pro Arg Val
145                 150                 155                 160

Ile Asp Trp Pro Pro Leu Pro Ser Cys Val Trp Ser Arg Ile Val Glu
                165                 170                 175

Pro Glu Pro Arg Leu Leu Phe Arg Phe Ser Ala Leu Thr Phe Asn Ala
            180                 185                 190

His Arg Ile His Tyr Asp Arg Pro Tyr Ala Ile Asn Glu Glu Gly Tyr
        195                 200                 205

Pro Gly Leu Val Val His Gly Pro Leu Thr Ala Val Leu Leu Met Glu
    210                 215                 220

Leu Leu Arg Arg Glu Thr Ala Gln Ala Val Leu Asp Tyr Ser Phe Arg
225                 230                 235                 240

Gly Leu Ala Pro Leu Phe Asp Leu Ala Pro Phe Arg Leu Val Gly Thr
                245                 250                 255

Leu Val Asp Gly Arg Val Ser Leu Glu Ala Gln Gly Pro Asp Gly Ala
            260                 265                 270

Ala Ala Met Arg Ala Ser Ala Glu Leu Ala Pro Ala
        275                 280

<210> SEQ ID NO 31
<211> LENGTH: 9017
<212> TYPE: DNA
<213> ORGANISM: Artificial sequence
<220> FEATURE:
<223> OTHER INFORMATION: PMS4570 construct

<400> SEQUENCE: 31
gatctcttgg aggaatccat taatgagcgg aacaggacga ctggcaggaa agattgcgtt     60
aattaccggt ggcgccggca atatcggcag tgaattgaca cgtcgctttc tcgcagaggg    120
agcgacggtc attattagtg acggaatcg ggcgaagttg accgcactgg ccgaacggat    180
gcaggcagag gcaggagtgc cggcaaagcg catcgatctc gaagtcatgg atgggagtga    240
tccggtcgcg gtacgtgccg gtatcgaagc gattgtggcc cgtcacggcc agatcgacat    300
tctggtcaac aatgcaggaa gtgccggtgc ccagcgtcgt ctggccgaga ttccactcac    360
tgaagctgaa ttaggccctg cgccgaaga gacgcttcat gccagcatcg ccaatttact    420
tggtatggga tggcatctga tgcgtattgc ggcacctcat atgccggtag aagtgcggt    480 catcaatgtc tcgaccatct tttcacgggc tgagtactac gggcggattc cgtatgtcac    540
ccctaaagct gctcttaatg ctctatctca acttgctgcg cgtgagttag gtgcacgtgg    600
catccgcgtt aatacgatct ttcccggccc gattgaaagt gatcgcatcc gtacagtgtt    660
ccagcgtatg gatcagctca aggggcggcc cgaaggcgac acagcgcacc atttttgaa    720 caccatgcga ttgtgtcgtg ccaacgacca gggcgcgctt gaacgtcggt tcccctccgt    780
cggtgatgtg gcagacgccg ctgtctttct ggccagtgcc gaatccgccg ctctctccgg    840
tgagacgatt gaggttacgc acggaatgga gttgccggcc tgcagtgaga ccagcctgct    900

-continued

| | |
|---|---|
| ggcccgtact gatctgcgca cgattgatgc cagtggccgc acgacgctca tctgcgccgg | 960 |
| cgaccagatt gaagaggtga tggcgctcac cggtatgttg cgtacctgtg ggagtgaagt | 1020 |
| gatcatcggc ttccgttcgg ctgcggcgct ggcccagttc gagcaggcag tcaatgagag | 1080 |
| tcggcggctg gccggcgcag actttacgcc tcccattgcc ttgccactcg atccacgcga | 1140 |
| tccggcaaca attgacgctg tcttcgattg ggggccggc gagaataccg gcgggattca | 1200 |
| tgcagcggtg attctgcctg ctaccagtca cgaaccggca ccgtgcgtga ttgaggttga | 1260 |
| tgatgagcgg gtgctgaatt ttctggccga tgaaatcacc gggacaattg tgattgccag | 1320 |
| tcgcctggcc cgttactggc agtcgcaacg gcttacccc ggcgcacgtg cgcgtgggcc | 1380 |
| gcgtgtcatt tttctctcga cggtgccga tcaaaatggg aatgtttacg gacgcattca | 1440 |
| aagtgccgct atcggtcagc tcattcgtgt gtggcgtcac gaggctgaac ttgactatca | 1500 |
| gcgtgccagc gccgccggtg atcatgtgct gccgccggta tgggccaatc agattgtgcg | 1560 |
| cttcgctaac cgcagccttg aagggttaga atttgcctgt gcctggacag ctcaattgct | 1620 |
| ccatagtcaa cgccatatca atgagattac cctcaacatc cctgccaaca ttagcgccac | 1680 |
| caccggcgca cgcagtgcat cggtcggatg ggcggaaagc ctgatcgggt tgcatttggg | 1740 |
| gaaagttgcc ttgattaccg gtggcagcgc cggtattggt gggcagatcg ggcgcctcct | 1800 |
| ggctttgagt ggcgcgcgcg tgatgctggc agcccgtgat cggcataagc tcgaacagat | 1860 |
| gcaggcgatg atccaatctg agctggctga ggtggggtat accgatgtcg aagatcgcgt | 1920 |
| ccacattgca ccgggctgcg atgtgagtag cgaagcgcag cttgcggatc ttgttgaacg | 1980 |
| taccctgtca gcttttggca ccgtcgatta tctgatcaac aacgccggga tcgccggtgt | 2040 |
| cgaagagatg gttatcgata tgccagttga gggatggcgc catacctct tcgccaatct | 2100 |
| gatcagcaac tactcgttga tgcgcaaact ggcgccgttg atgaaaaaac agggtagcgg | 2160 |
| ttacatcctt aacgtctcat catactttgg cggtgaaaaa gatgcggcca ttccctaccc | 2220 |
| caaccgtgcc gattacgccg tctcgaaggc tggtcagcgg gcaatggccg aagtctttgc | 2280 |
| gcgcttcctt ggcccggaga tacagatcaa tgccattgcg ccgggtccgg tcgaaggtga | 2340 |
| tcgcttgcgc ggtaccggtg aacgtcccgg cctctttgcc cgtcgggcgc ggctgatttt | 2400 |
| ggagaacaag cggctgaatg agcttcacgc tgctcttatc gcggctgcgc gcaccgatga | 2460 |
| gcgatctatg cacgaactgg ttgaactgct cttacccaat gatgtggccg cactagagca | 2520 |
| gaatcccgca gcacctaccg cgttgcgtga actggcacga cgttttcgca gcgaaggcga | 2580 |
| tccggcggca tcatcaagca gtgcgctgct gaaccgttca attgccgcta aattgctggc | 2640 |
| tcgtttgcat aatggtggct atgtgttgcc tgccgacatc tttgcaaacc tgccaaaccc | 2700 |
| gcccgatccc ttcttcaccc gagcccagat tgatcgcgag gctcgcaagg ttcgtgacgg | 2760 |
| catcatgggg atgctctacc tgcaacggat gccgactgag tttgatgtcg caatggccac | 2820 |
| cgtctattac cttgccgacc gcaatgtcag tggtgagaca ttccacccat caggtggttt | 2880 |
| gcgttacgaa cgcacccta ccggtggcga actcttcggc ttgccctcac cggaacggct | 2940 |
| ggcggagctg gtcggaagca cggtctatct gataggtgaa catctgactg aacaccttaa | 3000 |
| cctgcttgcc cgtgcgtacc tcgaacgtta cggggcacgt caggtagtga tgattgttga | 3060 |
| gacagaaacc ggggcagaga caatgcgtcg cttgctccac gatcacgtcg aggctggtcg | 3120 |
| gctgatgact attgtggccg gtgatcagat cgaagccgct atcgaccagg ctatcactcg | 3180 |
| ctacggtcgc ccagggccgg tcgtctgtac ccccttccgg ccactgccga cggtaccact | 3240 |

```
ggtcgggcgt aaagacagtg actggagcac agtgttgagt gaggctgaat tgccgagtt      3300 gtgcgaacac cagctcaccc accatttccg ggtagcgcgc aagattgccc tgagtgatgg      3360
tgccagtctc gcgctggtca ctcccgaaac tacggctacc tcaactaccg agcaatttgc      3420
tctggctaac ttcatcaaaa cgacccttca cgcttttacg gctacgattg tgtcgagag      3480 cgaaagaact gctcagcgca ttctgatcaa tcaagtcgat ctgacccggc gtgcgcgtgc      3540
cgaagagccg cgtgatccgc acgagcgtca acaagaactg gaacgtttta tcgaggcagt      3600
cttgctggtc actgcaccac tcccgcctga agccgatacc cgttacgccg gcggattca      3660 tcgcggacgg gcgattaccg tgtaaggatc tgtttagtgc gatcgcggca ggacttaact      3720
gagcttcaga gaagacgcag ggacttcatc ccaagaagcc actgtccgca attgggcacg      3780
ccagccgttg gcccgctgtt ctggtgtcag attgcgctca aaggactcat ggcagtcgcg      3840
agcctgctgc tcgtcgcaag tcgcaatgca cgagtaaaga atgcccgccg ggtcgaattg      3900
ttcatttacc caaatcactt tgtcggttgc catagggggt tgctcctacg ctcagctgga      3960
tttagcgtct tctaatccag tgtagacagt agttttggct ccgttgagca ctgtagcctt      4020
gggcgatcgc tctaaacatt acataaattc acaaagtttt cgttacataa aaatagtgtc      4080
tacttagcta aaaattaagg gttttttaca ccttttttgac agttaatctc ctagcctaaa      4140
aagcaagagt ttttaactaa gactcttgcc cggatctctt ggaggaatcc attaatgcgc      4200
aagctagctc acaacttcta caaaccgttg gccatcggtg ctccggagcc gatccgcgag      4260
ctgccggttc gcccagagcg ggtcgtccac tttttttccgc cccacgtgga aaagattcgc      4320
gcccgtattc ccgaagtcgc caaacaggtt gatgtgctgt gcggcaatct ggaagacgcg      4380
attccgatgg acgccaaaga ggccgcccgc aacggcttta tcgaggtagt caaagcaacc      4440
gatttcggcg ataccgcgct ctgggtgcgg gtcaatgcgc tcaacagccc atgggtgctc      4500
gacgatattg ccgagattgt ggccgcggtg ggcaataaac tcgatgtgat tatgatcccg      4560
aaggtcgagg ggccgtggga cattcacttc gttgatcagt atctggcgct gctcgaagcc      4620
cgccaccaga tcaaaaagcc gattctgatc catgctctgc tagaaaccgc ccagggcatg      4680
gtcaatctgg aagaaattgc cggtgccagc ccccgcatgc acggcttcag tctgggggcg      4740
gctgatctcg ccgcttcgcg tggcatgaag accacccgtg tcggcggtgg gcaccccttc      4800 tacgcgtgc tggccgaccc gcaagaaggt caggccgagc ggccattcta tcagcaagac      4860
ctctggcact acacgattgc gcggatggtt gatgtggcag ttgcccatgg cctgcgcgcc      4920
ttctacggcc ccttcggcga catcaaggat gaagccgcct gcgaagccca attccgcaac      4980
gccttcctcc tcggctgcac cggtgcgtgg tcgctcgcgc ccaaccagat tcccatcgcc      5040
aagcgcgtct tcagcccgga cgtgaacgag gtgctcttcg ccaaacgcat cctgaaggcg      5100
atgcccgatg gttcgggggt ggcgatgatt gacggcaaga tgcaagacga tgcgacctgg      5160
aagcaggcga aggtgatcgt tgatctggcg cggatgattg cgaagaaaga ccccgacctg      5220
gcccaggcgt atggtctgtg aggatctctt ggaggaatcc attaatgagc gctaaaacca      5280
atcccggcaa cttcttcgag gattttcggc ttggtcagac gattgtccac gccacgccgc      5340
gcacgattac cgaaggcgac gttgccctct acacgtcgct gtacggttcc cgcttttgcgc      5400 ttacctcatc aaccccctttt gcgcaatcgt tggggctgga gcgagcgccg attgatagcc      5460
tgctggtgtt tcatatcgtc ttcggtaaga cggtacccga catctcgctc aacgcgattg      5520
ccaatctcgg ctacgccggt ggacgctttg gcgcagtggg ctaccccggc gacacccttt      5580
ccaccacttc aaaggtgatc ggtttgcgcc agaacaaaga cggcaaaacc ggtgtggtgt      5640
```

```
atgtccactc ggtggggtg aaccaatggg acgaggtcgt gctcgaatac atccgctggg    5700
tgatggtgcg gaagcgcgac ccgaacgcac cggcaccgga gacggttgtc cccgacctgc    5760
ccgactcggt accggtcacc gatttgaccg tcccgtacac cgtatcggcg gcgaactaca    5820
atctggccca cgccggcagc aactacctct gggacgatta cgaggtgggt gagaagatcg    5880
atcacgtgga cggggtcacg attgaggagg ccgagcacat gcaggcgacc cggctctacc    5940
agaacacagc gcgggtccac ttcaacctcc acgttgagcg ggaagggcgg tttggccggc    6000
ggatcgtgta cggcggccac atcatcagcc tggcgcgttc gttgtcgttc aacgggctgg    6060
ccaatgcgct gagcattgcg gccatcaaca gcgggcgcca caccaacccc agctttgccg    6120
gcgacacgat ctacgcctgg tcagagattc ttgccaagat ggcgattccg ggccgcaccg    6180
atattggcgc cttgcgggta cgtaccgtcg ccaccaaaga tcgcccgtgt cacgattttc    6240
cctaccgtga cgcggagggg aactacgatc cggcggtggt gcttgatttt gattacacag    6300
tattgatgcc gcgtcgggga tgaggatctc tcaacaggcc tgctggtaat cgcaggcctt    6360
tttttttgga tctgtttagt gcgatcgcgg caggacttaa ctgagcttca gagaagacgc    6420
agggacttca tcccaagaag ccactgtccg caattgggca cgccagccgt tggcccgctg    6480
ttctggtgtc agattgcgct caaaggactc atggcagtcg cgagcctgct gctcgtcgca    6540
agtcgcaatg cacgagtaaa gaatgcccgc cgggtcgaat tgttcattta cccaaatcac    6600
tttgtcggtt gccatagggg gttgctccta cgctcagctg gatttagcgt cttctaatcc    6660
agtgtagaca gtagttttgg ctccgttgag cactgtagcc ttgggcgatc gctctaaaca    6720
ttacataaat tcacaaagtt tcgttacat aaaaatagtg tctacttagc taaaaattaa    6780
gggttttta cacctttttg acagttaatc tcctagccta aaagcaaga gtttttaact    6840
aagactcttg cccggatctc ttggaggaat ccattaatga agggtattct ccacggattg    6900
cgtgtagtgg agggatcggc cttgttgcc gcaccgctgg ggggcatgac gctcgcgcag    6960
ttgggggccg atgtgattcg cttcgaccct atcggcggcg gtctcgatta taaacgctgg    7020
ccggttacgc tcgacggtaa gcatagtctg ttttgggccg gtctcaacaa gggcaaacgt    7080
tcgattgcga ttgatattcg ccatccacgc gggcaggagt tgctgacgca gcttatctgc    7140
gcacccggcg agcatgccgg tctctttatt accaattttc cggcgcgcgg ttggttgagt    7200
tacgatgagc tgaagcgtca ccgcgccgac ctgattatgg tcaatctggt cgggcggcgc    7260
gatggcgggt cagaggtgga ttacaccgtt aacccgcagt tggggctgcc gtttatgacc    7320
ggcccggtca cgacgcctga tgtggttaat cacgtgctgc cggcctggga tattgtgacc    7380
gggcagatga ttgcgctcgg tctgctggct gccgagcgtc accgtcggct gaccggtgag    7440
gggcaactgg tgaagattgc gctgaaggat gtcgggctgg cgatgatcgg ccatctgggg    7500
atgattgccg aggtgatgat caacgatacc gaccgtccac ggcaggggaa ttatctctac    7560
ggggcgttcg ggcgcgattt cgagaccctc gatgggaagc gggtgatggt ggttggtttg    7620
accgatttgc agtggaaggc gctgggcaag gcgaccggtc tgacggatgc gttcaatgcg    7680
ctcggtgcgc ggctggggct gaatatggac gaggaaggcg accgcttccg tgcccgccac    7740
gagatcgctg cgctgcttga accctggttc cacgcccgca cgctgccga ggtacgacgc    7800
atctttgaac agcaccgcgt cacctgggcg ccgtaccgca cggtacggga agcgattgcc    7860
caggaccccg actgctccac cgataacccg atgtttgcga tggtcgagca gcccggcatt    7920
gggagctacc tgatgccggg ttcgccgctg gatttcactg ccgtcccgcg tctgcctgtc    7980
```

```
cagcctgcgc cccggctcgg cgagcacacc gatgagattt tgctggaggt gctgggcttg    8040
agtgaagctg aagtcggtcg cttgcacgat gaagggattg tggccgggcc agatcgggca    8100
gcgtagggat ctcttggagg aatccattaa tgagcagcgc ggattggatg gcctggattg    8160
ggcgtactga gcaggtggaa gatgatattt gtctggccca ggcgattgcc gcagccgcaa    8220
cgcttgagcc gccgtcggga gcaccaactg cggatagtcc gctccctccg ctctggcact    8280
ggttttactt tctgccccgt gccccacagt cgcagctcag cagtgatggt catccgcagc    8340
gcggcggctt tatcccaccg ataccctatc cacgccgcat gtttgccggt gcccgcatcc    8400
gctttcatca cccgctgcgc atcggccaac cggcgcgtcg tgaaggtgtg atccgcaaca    8460
tcactcaaaa aagcggtcgc agcgggccgc tggcatttgt gacggtcggc taccagatat    8520
accaacatga gatgctttgt atcgaagaag agcaagacat cgtgtaccgt gagccggggg    8580
caccggtgcc ggcccccaca ccggtagagt taccaccggt acacgatgca atcacccgta    8640
ctgttgtgcc cgatccgcgt ctgctctttc gcttctcagc cctcaccttc aatgcgcatc    8700
ggattcacta cgaccggcca tacgctcagc acgaagaggg ctatccgggc ctggtcgtgc    8760 atggcccccct ggtagcagtc ctgctaatgg aactggcccg tcaccataca tcccgcccga    8820
ttgttggctt ttcgttccgc agccaggcgc cactcttcga tctggccccc ttccgcctgc    8880
tggcccgccc caacggcgac cgcatcgatc tggaagcaca gggacctgac ggggcaacgg    8940
cgctcagcgc gacggttgag ttgggggat gaggatctct caacaggcct gctggtaatc    9000
gcaggccttt ttttttg                                                 9017
```

<210> SEQ ID NO 32
<211> LENGTH: 10244
<212> TYPE: DNA
<213> ORGANISM: Artificial sequence
<220> FEATURE:
<223> OTHER INFORMATION: PMS4591 construct

<400> SEQUENCE: 32

```
gatctatgga tggcattctg aagggtttgc gtgtcgtgga aggttcggcg ttcgtcgctg      60
caccgctcgg ggggatgact ttggcacagt tgggagctga tgtgattcgc tttgatccta     120
tcggcggtgg actggattac cgcagatggc cactcactct tgatggccgc catagtttgt     180
tctgggcggg gctcaataag ggcaaaagat caattgctgt cgatctgcgg ttgcctcgcg     240
gtcaagaact gttgacgcag ctcatctgtg cgccgggtga tcatgctgga ctgttttcta     300
ccaacttccc cgctaagggc tggcttgctt acgaggccct gcaagcacac cgccaggatt     360
tgattatggt caatctcact ggtcgtcggg atggggcag cgaagttgat tatacactca     420
accctcaact cgggcttcca ctgatgacag gcccgacgtc tagccccgag gttgtgaatc     480 atgtgttcc agcctgggat tcatttctg gtcaaatgat cgcactggga ctccttgctg     540
ccgaaagaca ccgcagactc acgggagagg gacagcttgt tcgtttggcc ctcaaggatg     600
tggctcttgc catgctgggt aactttggaa tgctggcaga agcgatggtt aatgggcgg     660 atcgtccgcg gcagggtaac tacttgtatg gggcttttgg ccgcgatttc gggacccttg     720
atggccgtcg gctgatggtc gttggtttga cgggaatgca gtggcgcaga ctggtgaaag     780
ctaccggttt gagagaaccc attagtgagt tggcagcgcg tcttggactg gatttcgatg     840
atgaaggcaa tcgctataga gcccgtcagg aaatcgcacg gttgtttgag ccttggttcc     900 atgccccgcac cctcgcagag gctgcctga ctctcgatgc ccacggtgtc acatgggac      960 catacagatc ggtgcgtgaa gaggtcgcag ctgatcctga ttgctccact gataacccca    1020
```

```
tgtttacctt gactgaacaa cctgggatcg gccgctatct catgccgtcg acaccccttg   1080
atttcgcagg agttcctaga ctgccagcaa tgcctgctcc aagattggga gagcacacag   1140
atcagattct gttggatatc ctcggactca gcgaggcaga agttgggcgg ctccatgatg   1200
cgagagtggt ggcaggtccg acataaggat ctcttggagg aatccattaa tgagcggaac   1260
aggacgactg gcaggaaaga ttgcgttaat taccggtggc gccggcaata tcggcagtga   1320
attgacacgt cgctttctcg cagagggagc gacggtcatt attagtggac ggaatcgggc   1380
gaagttgacc gcactggccg aacggatgca ggcagaggca ggagtgccgg caaagcgcat   1440
cgatctcgaa gtcatggatg ggagtgatcc ggtcgcggta cgtgccggta tcgaagcgat   1500
tgtggcccgt cacggccaga tcgacattct ggtcaacaat gcaggaagtg ccggtgccca   1560
gcgtcgtctg gccgagattc cactcactga agctgaatta ggccctggcg ccgaagagac   1620
gcttcatgcc agcatcgcca atttacttgg tatgggatgg catctgatgc gtattgcggc   1680
acctcatatg ccggtaggaa gtgcggtcat caatgtctcg accatctttt cacgggctga   1740
gtactacggg cggattccgt atgtcacccc taaagctgct cttaatgctc tatctcaact   1800
tgctgcgcgt gagttaggtg cacgtggcat ccgcgttaat acgatctttc ccggcccgat   1860
tgaaagtgat cgcatccgta cagtgttcca gcgtatggat cagctcaagg ggcggcccga   1920
aggcgacaca gcgcaccatt ttttgaacac catgcgattg tgtcgtgcca acgaccaggg   1980
cgcgcttgaa cgtcggttcc cctccgtcgg tgatgtggca gacgccgctg tctttctggc   2040
cagtgccgaa tccgccgctc tctccggtga gacgattgag gttacgcacg gaatggagtt   2100
gccggcctgc agtgagacca gcctgctggc ccgtactgat ctgcgcacga ttgatgccag   2160
tggccgcacg acgctcatct gcgccggcga ccagattgaa gaggtgatgg cgctcaccgg   2220
tatgttgcgt acctgtggga gtgaagtgat catcggcttc cgttcggctg cggcgctggc   2280
ccagttcgag caggcagtca atgagagtcg gcggctggcc ggcgcagact ttacgcctcc   2340
cattgccttg ccactcgatc cacgcgatcc ggcaacaatt gacgctgtct tcgattgggg   2400
ggccggcgag aataccggcg ggattcatgc agcggtgatt ctgcctgcta ccagtcacga   2460
accggcaccg tgcgtgattg aggttgatga tgagcgggtg ctgaattttc tggccgatga   2520
aatcaccggg acaattgtga ttgccagtcg cctggcccgt tactggcagt cgcaacggct   2580
tacccccggc gcacgtgcgc gtgggccgcg tgtcattttt ctctcgaacg gtgccgatca   2640
aaatgggaat gtttacggac gcattcaaag tgccgctatc ggtcagctca ttcgtgtgtg   2700
gcgtcacgag gctgaacttg actatcagcg tgccagcgcc gccggtgatc atgtgctgcc   2760
gccggtatgg gccaatcaga ttgtgcgctt cgctaaccgc agccttgaag ggttagaatt   2820
tgcctgtgcc tggacagctc aattgctcca tagtcaacgc catatcaatg agattaccct   2880
caacatccct gccaacatta gcgccaccac cggcgcacgc agtgcatcgg tcggatgggc   2940
ggaaagcctg atcgggttgc atttggggaa agttgccttg attaccggtg gcagcgccgg   3000
tattggtggg cagatcgggc gcctcctggc tttgagtggc gcgcgcgtga tgctggcagc   3060
ccgtgatcgg cataagctcg aacagatgca ggcgatgatc caatctgagc tggctgaggt   3120
ggggtatacc gatgtcgaag atcgcgtcca cattgcaccg gctgcgatg tgagtagcga   3180 agcgcagctt gcggatcttg ttgaacgtac cctgtcagct tttggcaccg tcgattatct   3240
gatcaacaac gccgggatcg ccggtgtcga agagatggtt atcgatatgc cagttgaggg   3300
atggcgccat accctcttcg ccaatctgat cagcaactac tcgttgatgc gcaaactggc   3360
```

```
gccgttgatg aaaaaacagg gtagcggtta catccttaac gtctcatcat actttggcgg    3420
tgaaaaagat gcggccattc cctacccaa  ccgtgccgat tacgccgtct cgaaggctgg    3480
tcagcgggca atggccgaag tctttgcgcg cttccttggc ccggagatac agatcaatgc    3540
cattgcgccg ggtccggtcg aaggtgatcg cttgcgcgt  accggtgaac gtcccggcct    3600
ctttgcccgt cgggcgcggc tgattttgga gaacaagcgg ctgaatgagc ttcacgctgc    3660
tcttatcgcg gctgcgcgca ccgatgagcg atctatgcac gaactggttg aactgctctt    3720
acccaatgat gtggccgcac tagagcagaa tcccgcagca cctaccgcgt tgcgtgaact    3780
ggcacgacgt tttcgcagcg aaggcgatcc ggcggcatca tcaagcagtg cgctgctgaa    3840
ccgttcaatt gccgctaaat tgctggctcg tttgcataat ggtggctatg tgttgcctgc    3900
cgacatcttt gcaaacctgc caaacccgcc cgatcccttc ttcacccgag cccagattga    3960
tcgcgaggct cgcaaggttc gtgacggcat catggggatg ctctacctgc aacggatgcc    4020
gactgagttt gatgtcgcaa tggccaccgt ctattacctt gccgaccgca atgtcagtgg    4080
tgagacattc cacccatcag gtggtttgcg ttacgaacgc acccctaccg gtggcgaact    4140
cttcggcttg ccctcaccgg aacggctggc ggagctggtc ggaagcacgg tctatctgat    4200
aggtgaacat ctgactgaac accttaacct gcttgcccgt gcgtacctcg aacgttacgg    4260
ggcacgtcag gtagtgatga ttgttgagac agaaaccggg gcagagacaa tgcgtcgctt    4320
gctccacgat cacgtcgagg ctggtcggct gatgactatt gtggccggtg atcagatcga    4380
agccgctatc gaccaggcta tcactcgcta cggtcgccca gggccggtcg tctgtacccc    4440
cttccggcca ctgccgacgg taccactggt cgggcgtaaa gacagtgact ggagcacagt    4500
gttgagtgag gctgaatttg ccgagttgtg cgaacaccag ctcacccacc atttccgggt    4560
agcgcgcaag attgccctga gtgatggtgc cagtctcgcg ctggtcactc ccgaaactac    4620
ggctacctca actaccgagc aatttgctct ggctaacttc atcaaaacga cccttcacgc    4680
ttttacgget acgattggtg tcgagagcga aagaactgct cagcgcattc tgatcaatca    4740
agtcgatctg accggcgtg  cgcgtgccga agagccgcgt gatccgcacg agcgtcaaca    4800
agaactggaa cgttttatcg aggcagtctt gctggtcact gcaccactcc cgcctgaagc    4860
cgataccegt tacgccgggc ggattcatcg cggacgggcg attaccgtgt aaggatctgt    4920
ttagtgcgat cgcggcagga cttaactgag cttcagagaa gacgcaggga cttcatccca    4980
agaagccact gtccgcaatt gggcacgcca gccgttggcc cgctgttctg tgtgtcagatt   5040
gcgctcaaag gactcatggc agtcgcgagc ctgctgctcg tcgcaagtcg caatgcacga    5100
gtaaagaatg cccgccgggt cgaattgttc atttacccaa atcactttgt cggttgccat    5160
aggggggttgc tcctacgctc agctggattt agcgtcttct aatccagtgt agacagtagt   5220
tttggctccg ttgagcactg tagccttggg cgatcgctct aaacattaca taaattcaca    5280
aagttttcgt tacataaaaa tagtgtctac ttagctaaaa attaagggtt ttttacacct    5340
ttttgacagt taatctccta gcctaaaaag caagagtttt taactaagac tcttgcccgg    5400
atctcttgga ggaatccatt aatgcgcaag ctagctcaca acttctacaa accgttggcc    5460
atcggtgctc cggagccgat ccgcgagctg ccggttcgcc cagagcgggt cgtccacttt    5520
tttccgcccc acgtggaaaa gattcgcgcc cgtattcccg aagtcgccaa acaggttgat    5580
gtgctgtgcg gcaatctgga agacgcgatt ccgatggacg ccaaagaggc cgcccgcaac    5640
ggctttatcg aggtagtcaa agcaaccgat ttcggcgata ccgcgctctg ggtgcgggtc    5700
aatgcgctca acagcccatg ggtgctcgac gatattgccg agattgtggc cgcggtgggc    5760
```

```
aataaactcg atgtgattat gatcccgaag gtcgaggggc cgtgggacat tcacttcgtt    5820
gatcagtatc tggcgctgct cgaagcccgc caccagatca aaaagccgat tctgatccat    5880
gctctgctag aaaccgccca gggcatggtc aatctggaag aaattgccgg tgccagcccc    5940
cgcatgcacg gcttcagtct ggggccggct gatctcgccg cttcgcgtgg catgaagacc    6000
acccgtgtcg gcggtgggca ccccttctac ggcgtgctgg ccgacccgca agaaggtcag    6060
gccgagcggc cattctatca gcaagacctc tggcactaca cgattgcgcg gatggttgat    6120
gtggcagttg cccatggcct gcgcgccttc tacggcccct tcggcgacat caaggatgaa    6180
gccgcctgcg aagcccaatt ccgcaacgcc ttcctcctcg gctgcaccgg tgcgtggtcg    6240
ctcgcgccca accagattcc catcgccaag cgcgtcttca gcccggacgt gaacgaggtg    6300
ctcttcgcca aacgcatcct ggaggcgatg cccgatggtt cggggggtggc gatgattgac    6360
ggcaagatgc aagacgatgc gacctggaag caggcgaagg tgatcgttga tctggcgcgg    6420
atgattgcga gaaagaccc cgacctggcc caggcgtatg gtctgtgagg atctcttgga    6480
ggaatccatt aatgagcgct aaaaccaatc ccggcaactt cttcgaggat tttcggcttg    6540
gtcagacgat tgtccacgcc acgccgcgca cgattaccga aggcgacgtt gccctctaca    6600
cgtcgctgta cggttcccgc tttgcgctta cctcatcaac cccctttgcg caatcgttgg    6660
ggctggagcg agcgccgatt gatagcctgc tggtgtttca tatcgtcttc ggtaagacgg    6720
tacccgacat ctcgctcaac gcgattgcca atctcggcta cgccggtgga cgctttggcg    6780
cagtggtcta ccccggcgac acccttttcca ccacttcaaa ggtgatcggt ttgcgccaga    6840
acaaagacgg caaaaccggt gtggtgtatg tccactcggt gggggtgaac caatgggacg    6900
aggtcgtgct cgaatacatc cgctgggtga tggtgcggaa gcgcgacccg aacgcaccgg    6960
caccggagac ggttgtcccc gacctgcccg actcggtacc ggtcaccgat ttgaccgtcc    7020
cgtacaccgt atcggcggcg aactacaatc tggcccacgc cggcagcaac tacctctggg    7080
acgattacga ggtgggtgag aagatcgatc acgtggacgg ggtcacgatt gaggaggccg    7140
agcacatgca ggcgacccgg ctctaccaga acacagcgcg ggtccacttc aacctccacg    7200
ttgagcggga agggcggttt ggccggcgga tcgtgtacgg cggccacatc atcagcctgg    7260
cgcgttcgtt gtcgttcaac gggctggcca atgcgctgag cattgcggcc atcaacagcg    7320
gcgccacac caaccccagc tttgccggcg acacgatcta cgcctggtca gagattcttg    7380
ccaagatggc gattccgggc cgcaccgata ttggcgcctt gcgggtacgt accgtcgcca    7440
ccaaagatcg cccgtgtcac gatttttccct accgtgacgc ggagggggaac tacgatccgg    7500
cggtggtgct tgattttgat tacacagtat tgatgccgcg tcggggatga ggatctctca    7560
acaggcctgc tggtaatcgc aggccttttt ttttggatct gtttagtgcg atcgcggcag    7620
gacttaactg agcttcagag aagacgcagg gacttcatcc caagaagcca ctgtccgcaa    7680
ttgggcacgc cagccgttgg cccgctgttc tggtgtcaga ttgcgctcaa aggactcatg    7740
gcagtcgcga gcctgctgct cgtcgcaagt cgcaatgcac gagtaaagaa tgcccgccgg    7800
gtcgaattgt tcatttaccc aaatcacttt gtcggttgcc ataggggggtt gctcctacgc    7860
tcagctggat ttagcgtctt ctaatccagt gtagacagta gttttggctc cgttgagcac    7920
tgtagccttg ggcgatcgct ctaaacatta cataaattca caaagttttc gttacataaa    7980
aatagtgtct acttagctaa aaattaaggg ttttttacac cttttgaca gttaatctcc    8040
tagcctaaaa agcaagagtt tttaactaag actcttgccc ggatctcttg gaggaatcca    8100
```

| | | | | |
|---|---|---|---|---|
| ttaatgaagg | gtattctcca | cggattgcgt | gtagtggagg | gatcggcctt tgttgccgca | 8160 |
| ccgctggggg | gcatgacgct | cgcgcagttg | ggggccgatg | tgattcgctt cgaccctatc | 8220 |
| ggcggcggtc | tcgattataa | acgctggccg | gttacgctcg | acggtaagca tagtctgttt | 8280 |
| tgggccggtc | tcaacaaggg | caaacgttcg | attgcgattg | atattcgcca tccacgcggg | 8340 |
| caggagttgc | tgacgcagct | tatctgcgca | cccggcgagc | atgccggtct ctttattacc | 8400 |
| aattttccgg | cgcgcggttg | gttgagttac | gatgagctga | agcgtcaccg cgccgacctg | 8460 |
| attatggtca | atctggtcgg | gcggcgcgat | ggcgggtcag | aggtggatta caccgttaac | 8520 |
| ccgcagttgg | ggctgccgtt | tatgaccggc | ccggtcacga | cgcctgatgt ggttaatcac | 8580 |
| gtgctgccgg | cctgggatat | tgtgaccggg | cagatgattg | cgctcggtct gctggctgcc | 8640 |
| gagcgtcacc | gtcggctgac | cggtgagggg | caactggtga | agattgcgct gaaggatgtc | 8700 |
| gggctggcga | tgatcggcca | tctggggatg | attgccgagg | tgatgatcaa cgataccgac | 8760 |
| cgtccacggc | aggggaatta | tctctacggg | gcgttcgggc | gcgatttcga ccccctcgat | 8820 |
| gggaagcggg | tgatggtggt | tggtttgacc | gatttgcagt | ggaaggcgct gggcaaggcg | 8880 |
| accggtctga | cggatgcgtt | caatgcgctc | ggtgcgcggc | tggggctgaa tatggacgag | 8940 |
| gaaggcgacc | gcttccgtgc | cgccacgag | atcgctgcgc | tgcttgaacc ctggttccac | 9000 |
| gcccgcacgc | tggccgaggt | acgacgcatc | tttgaacagc | accgcgtcac ctgggcgccg | 9060 |
| taccgcacgg | tacgggaagc | gattgcccag | gaccccgact | gctccaccga taacccgatg | 9120 |
| tttgcgatgg | tcgagcagcc | cggcattggg | agctacctga | tgccgggttc gccgctggat | 9180 |
| ttcactgccg | tcccgcgtct | gcctgtccag | cctgcgcccc | ggctcggcga gcacaccgat | 9240 |
| gagattttgc | tggaggtgct | gggcttgagt | gaagctgaag | tcggtcgctt gcacgatgaa | 9300 |
| gggattgtgg | ccgggccaga | tcgggcagcg | tagggatctc | ttggaggaat ccattaatga | 9360 |
| gcagcgcgga | ttggatggcc | tggattgggc | gtactgagca | ggtggaagat gatatttgtc | 9420 |
| tggcccaggc | gattgccgca | gccgcaacgc | ttgagccgcc | gtcgggagca ccaactgcgg | 9480 |
| atagtccgct | ccctccgctc | tggcactggt | tttactttct | gccccgtgcc ccacagtcgc | 9540 |
| agctcagcag | tgatggtcat | ccgcagcgcg | gcggctttat | cccaccgata ccctatccac | 9600 |
| gccgcatgtt | tgccggtgcc | cgcatccgct | ttcatcaccc | gctgcgcatc ggccaaccgg | 9660 |
| cgcgtcgtga | aggtgtgatc | cgcaacatca | ctcaaaaaag | cggtcgcagc gggccgctgg | 9720 |
| catttgtgac | ggtcggctac | cagatatacc | aacatgagat | gctttgtatc gaagaagagc | 9780 |
| aagacatcgt | gtaccgtgag | ccgggggcac | cggtgccggc | ccccacaccg gtagagttac | 9840 |
| caccggtaca | cgatgcaatc | acccgtactg | ttgtgcccga | tccgcgtctg ctctttcgct | 9900 |
| tctcagccct | caccttcaat | gcgcatcgga | ttcactacga | ccggccatac gctcagcacg | 9960 |
| aagagggcta | tccgggcctg | gtcgtgcatg | gcccccctggt | agcagtcctg ctaatggaac | 10020 |
| tggcccgtca | ccatacatcc | cgcccgattg | ttggcttttc | gttccgcagc caggcgccac | 10080 |
| tcttcgatct | ggcccccttc | cgcctgctgg | cccgccccaa | cggcgaccgc atcgatctgg | 10140 |
| aagcacaggg | acctgacggg | gcaacggcgc | tcagcgcgac | ggttgagttg gggggatgag | 10200 |
| gatctctcaa | caggcctgct | ggtaatcgca | ggccttttt | tttg | 10244 |

<210> SEQ ID NO 33
<211> LENGTH: 10253
<212> TYPE: DNA
<213> ORGANISM: Artificial sequence
<220> FEATURE:
<223> OTHER INFORMATION: PMS4749 construct

<400> SEQUENCE: 33

```
gatctatgaa gggtattctc cacggattgc gtgtagtgga gggatcggcc tttgttgccg      60
caccgctggg gggcatgacg ctcgcgcagt tgggggccga tgtgattcgc ttcgacccta     120
tcggcggcgg tctcgattat aaacgctggc cggttacgct cgacggtaag catagtctgt     180
tttgggccgg tctcaacaag ggcaaacgtt cgattgcgat tgatattcgc catccacgcg     240
ggcaggagtt gctgacgcag cttatctgcg cacccggcga gcatgccggt ctctttatta     300
ccaattttcc ggcgcgcggt tggttgagtt acgatgagct gaagcgtcac cgcgccgacc     360
tgattatggt caatctggtc gggcggcgcg atggcgggtc agaggtggat tacaccgtta     420
acccgcagtt ggggctgccg tttatgaccg gcccggtcac gacgcctgat gtggttaatc     480
acgtgctgcc ggcctgggat attgtgaccg ggcagatgat tgcgctcggt ctgctggctg     540
ccgagcgtca ccgtcggctg accggtgagg ggcaactggt gaagattgcg ctgaaggatg     600
tcgggctggc gatgatcggc catctgggga tgattgccga ggtgatgatc aacgataccg     660
accgtccacg gcagggggaat tatctctacg gggcgttcgg gcgcgatttc gagaccctcg     720
atgggaagcg ggtgatggtg gttggtttga ccgatttgca gtggaaggcg ctgggcaagg     780
cgaccggtct gacggatgcg ttcaatgcgc tcggtgcgcg gctggggctg aatatggacg     840
aggaaggcga ccgcttccgt gcccgccacg agatcgctgc gctgcttgaa ccctggttcc     900
acgcccgcac gctggccgag gtacgacgca tctttgaaca gcaccgcgtc acctgggcgc     960
cgtaccgcac ggtacgggaa gcgattgccc aggaccccga ctgctccacc gataacccga    1020
tgtttgcgat ggtcgagcag cccggcattg ggagctacct gatgccgggt tcgccgctgg    1080
atttcactgc cgtcccgcgt ctgcctgtcc agcctgcgcc ccggctcggc gagcacaccg    1140
atgagatttt gctggaggtg ctgggcttga gtgaagctga agtcggtcgc ttgcacgatg    1200
aagggattgt ggccgggcca gatcgggcag cgtagggatc tcttggagga atccattaat    1260
gagcggaaca ggacgactgg caggaaagat tgcgttaatt accggtggcg ccggcaatat    1320
cggcagtgaa ttgacacgtc gctttctcgc agagggagcg acggtcatta ttagtggacg    1380
gaatcgggcg aagttgaccg cactggccga acgatgcag gcagaggcag gagtgccggc    1440
aaagcgcatc gatctcgaag tcatggatgg gagtgatccg gtcgcggtac gtgccggtat    1500
cgaagcgatt gtggcccgtc acggccagat cgacattctg gtcaacaatg caggaagtgc    1560
cggtgcccag cgtcgtctgg ccgagattcc actcactgaa gctgaattag ccctggcgc     1620
cgaagagacg cttcatgcca gcatcgccaa tttacttggt atgggatggc atctgatgcg    1680
tattgcggca cctcatatgc cggtaggaag tgcggtcatc aatgtctcga ccatcttttc    1740
acgggctgag tactacgggc ggattccgta tgtcaccccct aaagctgctc ttaatgctct    1800
atctcaactt gctgcgcgtg agttaggtgc acgtggcatc cgcgttaata cgatcttttcc   1860
cggcccgatt gaaagtgatc gcatccgtac agtgttccag cgtatggatc agctcaaggg    1920
gcggcccgaa ggcgacacag cgcaccattt tttgaacacc atgcgattgt gtcgtgccaa    1980
cgaccagggc gcgcttgaac gtcggttccc ctccgtcggt gatgtggcag acgccgctgt    2040
ctttctggcc agtgccgaat ccgccgctct ctccggtgag acgattgagg ttacgcacgg    2100
aatggagttg ccggcctgca gtgagaccag cctgctggcc cgtactgatc tgcgcacgat    2160
tgatgccagt ggccgcacga cgctcatctg cgccggcgac cagattgaag aggtgatggc    2220
gctcaccggt atgttgcgta cctgtgggag tgaagtgatc atcggcttcc gttcggctgc    2280
```

```
ggcgctggcc cagttcgagc aggcagtcaa tgagagtcgg cggctggccg gcgcagactt    2340
tacgcctccc attgccttgc cactcgatcc acgcgatccg gcaacaattg acgctgtctt    2400
cgattggggg gccggcgaga ataccggcgg gattcatgca gcggtgattc tgcctgctac    2460
cagtcacgaa ccggcaccgt gcgtgattga ggttgatgat gagcgggtgc tgaattttct    2520
ggccgatgaa atcaccggga caattgtgat tgccagtcgc ctggcccgtt actggcagtc    2580
gcaacggctt accccggcg cacgtgcgcg tgggccgcgt gtcattttc tctcgaacgg    2640
tgccgatcaa aatgggaatg tttacggacg cattcaaagt gccgctatcg gtcagctcat    2700
tcgtgtgtgg cgtcacgagg ctgaacttga ctatcagcgt gccagcgccg ccggtgatca    2760
tgtgctgccg ccggtatggg ccaatcagat tgtgcgcttc gctaaccgca gccttgaagg    2820
gttagaattt gcctgtgcct ggacagctca attgctccat agtcaacgcc atatcaatga    2880
gattaccctc aacatccctg ccaacattag cgccaccacc ggcgcacgca gtgcatcggt    2940
cggatgggcg gaaagcctga tcgggttgca tttggggaaa gttgccttga ttaccggtgg    3000
cagcgccggt attggtgggc agatcggcg cctcctggct tgagtggcg cgcgcgtgat    3060
gctggcagcc cgtgatcggc ataagctcga acagatgcag gcgatgatcc aatctgagct    3120
ggctgaggtg gggtataccg atgtcgaaga tcgcgtccac attgcaccgg gctgcgatgt    3180
gagtagcgaa gcgcagcttg cggatcttgt tgaacgtacc ctgtcagctt ttggcaccgt    3240
cgattatctg atcaacaacg ccgggatcgc cggtgtcgaa gagatggtta tcgatatgcc    3300
agttgaggga tggcgccata ccctcttcgc caatctgatc agcaactact cgttgatgcg    3360
caaactggcg ccgttgatga aaaaacaggg tagcggttac atccttaacg tctcatcata    3420
ctttggcggt gaaaaagatg cggccattcc ctaccccaac cgtgccgatt acgccgtctc    3480
gaaggctggt cagcgggcaa tggccgaagt ctttgcgcgc ttccttggcc cggagataca    3540
gatcaatgcc attgcgccgg gtccggtcga aggtgatcgc ttgcgcggta ccggtgaacg    3600
tcccggcctc tttgcccgtc gggcgcggct gattttggag aacaagcggc tgaatgagct    3660
tcacgctgct cttatcgcgg ctgcgcgcac cgatgagcga tctatgcacg aactggttga    3720
actgctctta cccaatgatg tggccgcact agagcagaat cccgcagcac ctaccgcgtt    3780
gcgtgaactg gcacgacgtt ttcgcagcga aggcgatccg gcggcatcat caagcagtgc    3840
gctgctgaac cgttcaattg ccgctaaatt gctggctcgt ttgcataatg gtggctatgt    3900
gttgcctgcc gacatctttg caaacctgcc aaacccgccc gatcccttct tcacccgagc    3960
ccagattgat cgcgaggctc gcaaggttcg tgacggcatc atggggatgc tctacctgca    4020
acggatgccg actgagtttg atgtcgcaat ggccaccgtc tattaccttg ccgaccgcaa    4080
tgtcagtggt gagacattcc acccatcagg tggtttgcgt tacgaacgca ccctaccgg    4140
tggcgaactc ttcggcttgc cctcaccgga acggctggcg gagctggtcg aagcacggt    4200
ctatctgata ggtgaacatc tgactgaaca ccttaacctg cttgcccgtg cgtacctcga    4260
acgttacggg gcacgtcagg tagtgatgat tgttgagaca gaaaccgggg cagagacaat    4320
gcgtcgcttg ctccacgatc acgtcgaggc tggtcggctg atgactattg tggccggtga    4380
tcagatcgaa gccgctatcg accaggctat cactcgctac ggtcgcccag gccggtcgt    4440
ctgtaccccc ttccggccac tgccgacggt accactggtc gggcgtaaag acagtgactg    4500
gagcacagtg ttgagtgagg ctgaatttgc cgagttgtgc gaacaccagc tcacccacca    4560
tttccgggta gcgcgcaaga ttgccctgag tgatggtgcc agtctcgcgc tggtcactcc    4620
cgaaactacg gctacctcaa ctaccgagca atttgctctg gctaacttca tcaaaacgac    4680
```

```
ccttcacgct tttacggcta cgattggtgt cgagagcgaa agaactgctc agcgcattct   4740
gatcaatcaa gtcgatctga cccggcgtgc gcgtgccgaa gagccgcgtg atccgcacga   4800
gcgtcaacaa gaactggaac gttttatcga ggcagtcttg ctggtcactg caccactccc   4860
gcctgaagcc gatacccgtt acgccgggcg gattcatcgc ggacgggcga ttaccgtgta   4920
aggatctgtt tagtgcgatc gcggcaggac ttaactgagc ttcagagaag acgcagggac   4980
ttcatcccaa gaagccactg tccgcaattg ggcacgccag ccgttggccc gctgttctgg   5040
tgtcagattg cgctcaaagg actcatggca gtcgcgagcc tgctgctcgt cgcaagtcgc   5100
aatgcacgag taaagaatgc ccgccgggtc gaattgttca tttacccaaa tcactttgtc   5160
ggttgccata gggggttgct cctacgctca gctggattta gcgtcttcta atccagtgta   5220
gacagtagtt ttggctccgt tgagcactgt agccttgggc gatcgctcta acattacat   5280 aaattcacaa agttttcgtt acataaaaat agtgtctact tagctaaaaa ttaagggttt   5340
tttacacctt tttgacagtt aatctcctag cctaaaaagc aagagttttt aactaagact   5400
cttgcccgga tctcttggag gaatccatta atgcgcaagc tagctcacaa cttctacaaa   5460
ccgttggcca tcggtgctcc ggagccgatc cgcgagctgc cggttcgccc agagcgggtc   5520
gtccactttt ttccgcccca cgtggaaaag attcgcgccc gtattcccga agtcgccaaa   5580
caggttgatg tgctgtgcgg caatctggaa gacgcgattc cgatgacgc caaagaggcc   5640 gcccgcaacg gctttatcga ggtagtcaaa gcaaccgatt tcggcgatac cgcgctctgg   5700
gtgcgggtca atgcgctcaa cagcccatgg gtgctcgacg atattgccga gattgtggcc   5760
gcggtgggca ataaactcga tgtgattatg atcccgaagg tcgaggggcc gtgggacatt   5820
cacttcgttg atcagtatct ggcgctgctc gaagcccgcc accagatcaa aaagccgatt   5880
ctgatccatg ctctgctaga aaccgcccag ggcatggtca atctggaaga aattgccggt   5940
gccagccccc gcatgcacgg cttcagtctg gggccggctg atctcgccgc ttcgcgtggc   6000
atgaagacca cccgtgtcgg cggtgggcac cccttctacg gcgtgctggc cgacccgcaa   6060
gaaggtcagg ccgagcggcc attctatcag caagacctct ggcactacac gattgcgcgg   6120
atggttgatg tggcagttgc ccatggcctg cgcgccttct acggcccctt cggcgacatc   6180
aaggatgaag ccgcctgcga agcccaattc cgcaacgcct tcctcctcgg ctgcaccggt   6240
gcgtggtcgc tcgcgcccaa ccagattccc atcgccaagc gcgtcttcag cccggacgtg   6300
aacgaggtgc tcttcgccaa acgcatcctg gaggcgatgc ccgatggttc ggggtggcg    6360 atgattgacg gcaagatgca agacgatgcg acctggaagc aggcgaaggt gatcgttgat   6420
ctggcgcgga tgattgcgaa gaaagacccc gacctggccc aggcgtatgg tctgtgagga   6480
tctcttggag gaatccatta atgagcgcta aaaccaatcc cggcaacttc ttcgaggatt   6540
ttcggcttgg tcagacgatt gtccacgcca cgccgcgcac gattaccgaa ggcgacgttg   6600
ccctctacac gtcgctgtac ggttcccgct ttgcgcttac ctcatcaacc ccctttgcgc   6660
aatcgttggg gctggagcga gcgccgattg atagcctgct ggtgtttcat atcgtcttcg   6720
gtaagacggt acccgacatc tcgctcaacg cgattgccaa tctcggctac gccggtggac   6780
gctttggcgc agtggtctac cccggcgaca cccttttccac cacttcaaag gtgatcggtt   6840
tgcgccagaa caaagacggc aaaaccggtg tggtgtatgt ccactcggtg ggggtgaacc   6900
aatgggacga ggtcgtgctc gaatacatcc gctgggtgat ggtgcggaag cgcgacccga   6960
acgcaccggc accggagacg gttgtccccg acctgcccga ctcggtaccg gtcaccgatt   7020
```

-continued

```
tgaccgtccc gtacaccgta tcggcggcga actacaatct ggcccacgcc ggcagcaact      7080
acctctggga cgattacgag gtgggtgaga agatcgatca cgtggacggg gtcacgattg      7140
aggaggccga gcacatgcag gcgacccggc tctaccagaa cacagcgcgg gtccacttca      7200
acctccacgt tgagcgggaa gggcggtttg ccggcggat cgtgtacggc ggccacatca       7260
tcagcctggc gcgttcgttg tcgttcaacg ggctggccaa tgcgctgagc attgcggcca      7320
tcaacagcgg gcgccacacc aaccccagct ttgccggcga cacgatctac gcctggtcag      7380
agattcttgc caagatggcg attccgggcc gcaccgatat tggcgccttg cgggtacgta      7440
ccgtcgccac caaagatcgc ccgtgtcacg attttcccta ccgtgacgcg agggggaact      7500
acgatccggc ggtggtgctt gattttgatt acacagtatt gatgccgcgt cggggatgag      7560
gatctctcaa caggcctgct ggtaatcgca ggcctttttt tttggatctg tttagtgcga      7620
tcgcggcagg acttaactga gcttcagaga agacgcaggg acttcatccc aagaagccac      7680
tgtccgcaat tgggcacgcc agccgttggc ccgctgttct ggtgtcagat tgcgctcaaa      7740
ggactcatgg cagtcgcgag cctgctgctc gtcgcaagtc gcaatgcacg agtaaagaat      7800
gcccgccggg tcgaattgtt catttaccca aatcactttg tcggttgcca taggggttg      7860 ctcctacgct cagctggatt tagcgtcttc taatccagtg tagacagtag ttttggctcc      7920
gttgagcact gtagccttgg gcgatcgctc taaacattac ataaattcac aaagttttcg      7980
ttacataaaa atagtgtcta cttagctaaa aattaagggt ttttacacc tttttgacag      8040 ttaatctcct agcctaaaaa gcaagagttt ttaactaaga ctcttgcccg gatctcttgg      8100
aggaatccat taatgaaggg tattctccac ggattgcgtg tagtggaggg atcggccttt      8160
gttgccgcac cgctgggggg catgacgctc gcgcagttgg gggccgatgt gattcgcttc      8220 gacccctatcg gcgcggtct cgattataaa cgctggccgg ttacgctcga cggtaagcat      8280
agtctgtttt gggccggtct caacaagggc aaacgttcga ttgcgattga tattcgccat      8340
ccacgcgggc aggagttgct gacgcagctt atctgcgcac ccggcgagca tgccggtctc      8400
tttattacca attttccggc gcgcggttgg ttgagttacg atgagctgaa gcgtcaccgc      8460
gccgacctga ttatggtcaa tctggtcggg cggcgcgatg gcgggtcaga ggtggattac      8520
accgttaacc cgcagttggg gctgccgttt atgaccggcc cggtcacgac gcctgatgtg      8580
gttaatcacg tgctgccggc ctgggatatt gtgaccgggc agatgattgc gctcggtctg      8640
ctggctgccg agcgtcaccg tcggctgacc ggtgagggc aactggtgaa gattgcgctg       8700
aaggatgtcg ggctggcgat gatcggccat ctggggatga ttgccgaggt gatgatcaac      8760
gataccgacc gtccacggca ggggaattat ctctacgggg cgttcgggcg cgatttcgag      8820
accctcgatg ggaagcgggt gatggtggtt ggtttgaccg atttgcagtg gaaggcgctg      8880
ggcaaggcga ccggtctgac ggatgcgttc aatgcgctcg gtgcgcggct ggggctgaat      8940
atggacgagg aaggcgaccg cttccgtgcc cgccacgaga tcgctgcgct gcttgaaccc      9000
tggttccacg cccgcacgct ggccgaggta cgacgcatct ttgaacagca ccgcgtcacc      9060
tgggcgccgt accgcacggt acgggaagcg attgcccagg accccgactg ctccaccgat      9120
aacccgatgt ttgcgatggt cgagcagccc ggcattggga gctacctgat gccgggttcg      9180
ccgctggatt tcactgccgt cccgcgtctg cctgtccagc ctgcgccccg gctcggcgag      9240
cacaccgatg agattttgct ggaggtgctg ggcttgagtg aagctgaagt cggtcgcttg      9300
cacgatgaag ggattgtggc cgggccagat cgggcagcgt agggatctct tggaggaatc      9360
cattaatgag cagcgcggat tggatggcct ggattgggcg tactgagcag gtggaagatg      9420
```

```
atatttgtct ggcccaggcg attgccgcag ccgcaacgct tgagccgccg tcgggagcac    9480
caactgcgga tagtccgctc cctccgctct ggcactggtt ttactttctg ccccgtgccc    9540
cacagtcgca gctcagcagt gatggtcatc cgcagcgcgg cggctttatc ccaccgatac    9600
cctatccacg ccgcatgttt gccggtgccc gcatccgctt tcatcacccg ctgcgcatcg    9660
gccaaccggc gcgtcgtgaa ggtgtgatcc gcaacatcac tcaaaaaagc ggtcgcagcg    9720
ggccgctggc atttgtgacg gtcggctacc agatatacca acatgagatg ctttgtatcg    9780
aagaagagca agacatcgtg taccgtgagc cgggggcacc ggtgccggcc cccacaccgg    9840
tagagttacc accggtacac gatgcaatca cccgtactgt tgtgcccgat ccgcgtctgc    9900
tctttcgctt ctcagccctc accttcaatg cgcatcggat tcactacgac cggccatacg    9960
ctcagcacga agagggctat ccgggcctgg tcgtgcatgg ccccctggta gcagtcctgc   10020
taatggaact ggcccgtcac catacatccc gcccgattgt tggcttttcg ttccgcagcc   10080
aggcgccact cttcgatctg gccccttcc gcctgctggc ccgccccaac ggcgaccgca   10140
tcgatctgga agcacaggga cctgacgggg caacggcgct cagcgcgacg gttgagttgg   10200
ggggatgagg atctctcaac aggcctgctg gtaatcgcag gcctttttt ttg           10253
```

`<210>` SEQ ID NO 34
`<211>` LENGTH: 5492
`<212>` TYPE: DNA
`<213>` ORGANISM: Artificial sequence
`<220>` FEATURE:
`<223>` OTHER INFORMATION: PCS construct

`<400>` SEQUENCE: 34

```
gatctcttgg aggaatccat taatgatcga cactgcgccc cttgccccac cacgggcgcc      60
ccgctctaat ccgattcggg atcgagttga ttgggaagct cagcgcgctg ctgcgctggc     120
agatcccggt gccttttcatg gcgcgattgc ccggacagtt atccactggt acgacccaca    180
acaccattgc tggattcgct tcaacgagtc tagtcagcgt tgggaagggc tggatgccgc    240
taccggtgcc cctgtaacgg tagactatcc cgccgattat cagccctggc aacaggcgtt    300
tgatgatagt gaagcgccgt tttaccgctg gtttagtggt gggttgacaa atgcctgctt    360
taatgaagta gaccggcatg tcacgatggg ctatggcgac gaggtggcct actactttga    420
aggtgaccgc tgggataact cgctcaacaa tggtcgtggt ggtccggttg tccaggagac    480
aatcacgcgg cggcgcctgt tggtggaggt ggtgaaggct gcgcaggtgt tgcgtgatct    540
gggcctgaag aagggtgatc ggattgctct gaatatgccg aatattatgc cgcagattta    600
ttatacggaa gcggcaaaac gactgggtat tctgtacacg ccggtcttcg gtggcttctc    660
ggacaagact ctttccgacc gtattcacaa tgccggtgca cgagtggtga ttacctctga    720
tggtgcgtac cgcaacgcgc aggtggtgcc ctacaaagaa gcgtataccg atcaggcgct    780
cgataagtat attccggttg agacggcgca ggcgattgtt cgcagaccc tggccaccttt    840 gccctgact gagtcgcagc gccagacgat catcaccgaa gtggaggccg cactggccgg    900
tgagattacg gttgagcgct cggacgtgat gcgtggggtt ggttctgccc tcgcaaagct    960
ccgcgatctt gatgcaagcg tgcaggcaaa ggtgcgtaca gtactggcgc aggcgctggt   1020
cgagtcgccg ccgcgggttg aagctgtggt ggttgtgcgt cataccggtc aggagatttt   1080
gtggaacgag gggcgagatc gctggagtca cgacttgctg gatgctgcgc tggcgaagat   1140
tctggccaat gcgcgtgctg ccggctttga tgtgcacagt gagaatgatc tgctcaatct   1200
```

```
ccccgatgac cagcttatcc gtgcgctcta cgccagtatt ccctgtgaac cggttgatgc    1260
tgaatatccg atgtttatca tttacacatc gggtagcacc ggtaagccca agggtgtgat    1320
ccacgttcac ggcggttatg tcgccggtgt ggtgcacacc ttgcgggtca gttttgacgc    1380
cgagccgggt gatacgatat atgtgatcgc cgatccgggc tggatcaccg gtcagagcta    1440
tatgctcaca gccacaatgg ccggtcggct gaccggggtg attgccgagg atcaccgct    1500 cttcccctca gccgggcgtt atgccagcat catcgagcgc tatggggtgc agatctttaa    1560
ggcgggtgtg accttcctca agacagtgat gtccaatccg cagaatgttg aagatgtgcg    1620
actctatgat atgcactcgc tgcgggttgc aaccttctgc gccgagccgg tcagtccggc    1680
ggtgcagcag tttggtatgc agatcatgac cccgcagtat atcaattcgt actgggcgac    1740
cgagcacggt ggaattgtct ggacgcattt ctacggtaat caggacttcc cgcttcgtcc    1800
cgatgcccat acctatccct gccctgggt gatgggtgat gtctgggtgg ccgaaactga    1860
tgagagcggg acgacgcgct atcgggtcgc tgatttcgat gagaagggcg agattgtgat    1920
taccgccccg tatccctacc tgaccccgcac actctggggt gatgtgcccg gtttcgaggc    1980
gtacctgcgc ggtgagattc cgctgcgggc ctggaagggt gatgccgagc gtttcgtcaa    2040
gacctactgg cgacgtgggc aaacggtga atggggctat atccagggtg attttgccat    2100
caagtacccc gatggtagct tcacgctcca cggacgctct gacgatgtga tcaatgtgtc    2160
gggccaccgt atgggcaccg aggagattga gggtgccatt ttgcgtgacc gccagatcac    2220
gcccgactcg cccgtcggta attgtattgt ggtcggtgcg ccgcaccgtg agaagggtct    2280
gaccccggtt gccttcattc aacctgcgcc tggccgtcat ctgaccggcg ccgaccggcg    2340
ccgtctcgat gagctggtgc gtaccgagaa ggggcggtc agtgtcccag aggattacat    2400
cgaggtcagt gcctttcccg aaacccgcag cgggaagtat atgcggcgct ttttgcgcaa    2460
tatgatgctc gatgaaccac tgggtgatac gacgacgttg cgcaatcctg aagtgctcga    2520
agagattgca gccaagatcg ctgagtggaa acgccgtcag cgtatggccg aagagcagca    2580
gatcatcgaa cgctatcgct acttccggat cgagtatcac ccaccaacgg ccagtgcggg    2640
taaactcgcg gtagtgacgg tgacaaatcc gccggtgaac gcactgaatg agcgtgcgct    2700
cgatgagttg aacacaattg ttgaccaccct ggcccgtcgt caggatgttg ccgcaattgt    2760
cttcaccgga cagggcgcca ggagttttgt cgccggcgct gatattcgcc agttgctcga    2820
agagattcat acggttgaag aggcaatggc cctgccgaat aacgcccatc ttgctttccg    2880
caagattgag cgtatgaata agccgtgtat cgcggcgatc aacggtgtgg cgctcggtgg    2940
tggtctggaa ttcgccatgg cctgccatta ccgggttgcc gatgtctatg ccgaattcgg    3000
tcagccagag attaatctgc gcttgctacc tggttatggt ggcacgcagc gcttgccgcg    3060
cctgttgtac aagcgcaaca cggcaccgg tctgctccga gcgctggaga tgattctggg    3120
tgggcgtagc gtaccggctg atgaggcgct ggagctgggt ctgatcgatg ccattgctac    3180
cggcgatcag gactcactgt cgctggcatg cgcgttagcc cgtgccgcaa tcggcgccga    3240
tggtcagttg atcgagtcgg ctgcggtgac ccaggctttc cgccatcgcc acgagcagct    3300
tgacgagtgg cgcaaaccag acccgcgctt gccgatgac gaactgcgct cgattatcgc    3360
ccatccacgt atcgagcgga ttatccggca ggcccatacc gttgggcgcg atgcggcagt    3420
gcatcgggca ctggatgcaa tccgctatgg cattatccac ggcttcgagg ccggtctgga    3480
gcacgaggcg aagctctttg ccgaggcagt ggttgacccg aacggtggca agcgtggtat    3540
tcgcgagttc ctcgaccgcc agagtgcgcc gttgccaacc cgccgaccat tgattacacc    3600
```

```
tgaacaggag caactcttgc gcgatcagaa agaactgttg ccggttggtt caccctctt    3660
ccccggtgtt gaccggattc cgaagtggca gtacgcgcag gcggttattc gtgatccgga    3720
caccggtgcg gcggctcacg gcgatcccat cgtggctgaa aagcagatta ttgtgccggt    3780
ggaacgcccc cgcgccaatc aggcgctgat ctatgttctg gcctcggagg tgaacttcaa    3840
cgatatctgg gcgattaccg gtattccggt gtcacggttt gatgagcacg accgcgactg    3900
gcacgttacc ggttcaggtg gcatcggcct gatcgttgcg ctgggtgaag aggcgcgacg    3960
cgaaggccgg ctgaaggtgg gtgatctggt ggcgatctac tccgggcagt cggatctgct    4020
ctcaccgctg atgggccttg atccgatggc cgccgatttc gtcatccagg gaacgacac    4080
gccagatgga tcgcatcagc aatttatgct ggcccaggcc ccgcagtgtc tgcccatccc    4140
aaccgatatg tctatcgagg cagccggcag ctacatcctc aatctcggta cgatctatcg    4200
cgccctcttt acgacgttgc aaatcaaggc cggacgcacc atctttatcg agggtgcggc    4260
gaccggtacc ggtctggacg cagcgcgctc ggcggcccgg aatggtctgc gcgtaattgg    4320
aatggtcagt tcgtcgtcac gtgcgtctac gctgctggct gcgggtgccc acggtgcgat    4380
taaccgtaaa gacccggagg ttgccgattg tttcacgcgc gtgcccgaag atccatcagc    4440
ctgggcagcc tgggaagccg ccggtcagcc gttgctggcg atgttccggg cgcagaacga    4500
cgggcgactg gccgattatg tggtctcgca cgcgggcgag acggccttcc cgcgcagttt    4560
ccagcttctc ggcgagccac gcgatggtca cattccgacg ctcacattct acggtgccac    4620
cagtggctac cacttcacct tcctgggtaa gccagggtca gcttcgccga ccagatgct    4680
gcggcgggcc aatctccgcg ccggtgaggc ggtgttgatc tactacgggg ttgggagcga    4740
tgacctggta gataccggcg gtctggaggc tatcgaggcg gcgcggcaaa tgggagcgcg    4800
gatcgtcgtc gttaccgtca gcgatgcgca acgcgagttt gtcctctcgt tgggcttcgg    4860
ggctgcccta cgtggtgtcg tcagcctggc ggaactcaaa cggcgcttcg gcgatgagtt    4920
tgagtggccg cgcacgatgc cgccgttgcc gaacgcccgc caggaccgcc agggtctgaa    4980
agaggctgtc cgccgcttca cgatctggt cttcaagccg ctaggaagcg cggtcggtgt    5040
cttcttgcgg agtgccgaca atccgcgtgg ctaccccgat ctgatcatcg agcgggctgc    5100
ccacgatgca ctggcggtga gcgcgatgct gatcaagccc ttcaccggac ggattgtcta    5160
cttcgaggac attggtgggc ggcgttactc cttcttcgca ccgcaaatct gggtgcgcca    5220
gcgccgcatc tacatgccga cggcacagat cttggtacg cacctctcaa atgcgtatga    5280
aattctgcgt ctgaatgatg agatcagcgc cggtctgctg acgattaccg agccggcagt    5340
ggtgccgtgg gatgaactac ccgaagcaca tcaggcgatg tgggaaaatc gccacacggc    5400
ggccacttat gtggtgaatc atgccttacc acgtctcggc ctaaagaaca gggacgagct    5460
gtacgaggcg tggacggccg gcgagcggta gg                                  5492
```

<210> SEQ ID NO 35
<211> LENGTH: 8370
<212> TYPE: DNA
<213> ORGANISM: Artificial sequence
<220> FEATURE:
<223> OTHER INFORMATION: pAM1573PMS construct

<400> SEQUENCE: 35

```
gatccgggag tttgtagaaa cgcaaaaagg ccatccgtca ggatggcctt ctgcttaatt      60
tgatgcctgg cagtttatgg cgggcgtcct gcccgccacc ctccgggccg ttgcttcgca     120
```

```
acgttcaaat ccgctcccgg cggatttgtc ctactcagga gagcgttcac cgacaaacaa    180
cagataaaac gaaaggccca gtctttcgac tgagcctttc gttttatttg atgcctggca    240
gttccctact ctcgcatggg gagaccccac actaccatcg gcgctacggc gtttcacttc    300
tgagttcggc atggggtcag gtgggaccac cgcgctactg ccgccaggca aattctgttt    360
tattgagccg ttaccccacc tactagctaa tcccatctgg gcacatccga tggcaagagg    420
cccgaaggtc cccctctttg gtcttgcgac gttatgcggt attagctacc gtttccagta    480
gttatccccc tccatcaggc agtttcccag acattactca cccgtccgcc actcgtcagc    540
aaagaagcaa gcttagatcc gtcacacggg ataataccgc gccacatagc agaactttaa    600
aagtgctcat cattggaaaa cgttcttcgg ggcgaaaact ctcaaggatc ttaccgctgt    660
tgagatccag ttcgatgtaa cccactcgtg cacccaactg atcttcagca tcttttactt    720
tcaccagcgt ttctgggtga gcaaaaacag gaaggcaaaa tgccgcaaaa aagggaataa    780
gggcgacacg gaaatgttga atactcatac tcttcctttt tcaatattat tgaagcattt    840
atcagggtta ttgtctcatg agcggataca tatttgaatg tatttagaaa aataaacaaa    900
taggggttcc gcgcacattt ccccgaaaag tgccacctga cgtctaagaa accattatta    960
tcatgacatt aacctataaa aataggcgta tcacgaggcc ctttcgtctt cgaataaata   1020
cctgtgacgg aagatcactt cgcagaataa ataaatcctg gtgtccctgt tgataccggg   1080
aagccctggg ccaacttttg gcgaaaatga gacgttgatc ggcacgtaag aggttccaac   1140
tttcaccata atgaaataag atcactaccg ggcgtatttt ttgagttatc gagattttca   1200
ggagctaagg aagctaaaat ggagaaaaaa atcactggat ataccaccgt tgatatatcc   1260
caatggcatc gtaaagaaca ttttgaggca tttcagtcag ttgctcaatg tacctataac   1320
cagaccgttc agctggatat tacggccttt ttaaagaccg taaagaaaaa taagcacaag   1380
ttttatccgg cctttattca cattcttgcc cgcctgatga atgctcatcc ggagttccgt   1440
atggcaatga agacggtga gctggtgata tgggatagtg ttcacccttg ttacaccgtt   1500
ttccatgagc aaactgaaac gttttcatcg ctctggagtg aataccacga cgatttccgg   1560
cagtttctac acatatattc gcaagatgtg gcgtgttacg gtgaaaacct ggcctatttc   1620
cctaaagggt ttattgagaa tatgtttttc gtctcagcca atccctgggt gagtttcacc   1680
agttttgatt taaacgtggc caatatggac aacttcttcg cccccgtttt caccatgggc   1740
aaatattata cgcaaggcga caaggtgctg atgccgctgg cgattcaggt tcatcatgcc   1800
gtttgtgatg gcttccatgt cggcagaatg cttaatgaat tacaacagta ctgcgatgag   1860
tggcagggcg gggcgtaatt ttttaaggc agttattggt gcccttaaac gcctggtgct   1920
acgcctgaat aagtgataat aagcggatga atggcagaaa ttcgaaagca aattcgaccc   1980
ggtcgtcggt tcagggcagg gtcgttaaat agccgcttat gtctattgct ggtttaccgg   2040
tttattgact accggaagca gtgtgaccgt gtgcttctca aatgcctgag gccagtttgc   2100
tcaggctctc cccgtggagg taataattga cgatatgatc gacggatctg gtaacccag    2160 cgcggttgct accaagtagt gacccgcttc gtgatgcaaa atccgctgac gatattcggg   2220
cgatcgctgc tgaatgccat cgagcagtaa cgtggcaccc cgccctgcc aagtcaccgc    2280 atccagactg aacagcacca agaggctaaa acccaatccc gccggtagca gcggagaact   2340
acccagcatt ggtcccacca aagctaatgc cgtcgtggta aaaatcgcga tcgccgtcag   2400
actcaagccc agttcgctca tgcttcctca tctaggtcac agtcttcggc gatcgcatcg   2460
atctgatgct gcagcaagcg ttttccatac cggcgatcgc gccgtcgccc tttcgctgcc   2520
```

```
gtggcccgct tacgagctcg tttatcgacc acgatcgcat ccaaatccgc gatcgcttcc   2580
cagtccggca attcagtctg gggcgtccgt ttcattaatc ctgatcaggc acgaaattgc   2640
tgtgcgtagt atcgcgcata gcggccagcc tctgccaaca gcgcatcgtg attgcctgcc   2700
tcaacaatct ggccgcgctc catcaccaag atgcggctgg cattacgaac cgtagccaga   2760
cggtgagcaa tgataaagac cgtccgtccc tgcatcaccc gttctagggc ctcttgcacc   2820
aaggtttcgg actcggaatc aagcgccgaa gtcgcctcat ccagaattaa aatgcgtgaa   2880
tcctctacgc cggacgcatc gtggccggca tcaccggcgc cacaggtgcg gttgctggcg   2940
cctatatcgc cgacatcacc gatggggaag atcgggctcg ccacttcggg ctcatgagcg   3000
cttgtttcgg cgtgggtatg gtggcaggcc ccgtggccgg gggactgttg ggcgccatct   3060
ccttgcatgc accattcctt gcggcggcgg tgctcaacgg cctcaaccta ctactgggct   3120
gcttcctaat gcaggagtcg cataagggag agcgtcgatc gaccgatgcc cttgagagcc   3180
ttcaacccag tcagctcctt ccggtgggcg cggggcatga ctatcgtcgc cgcacttatg   3240
actgtcttct ttatcatgca actcgtagga caggtgccgg cagcgctctg ggtcattttc   3300
ggcgaggacc gctttcgctg gagcgcgacg atgatcggcc tgtcgcttgc ggtattcgga   3360
atcttgcacg ccctcgctca agccttcgtc actggtcccg ccaccaaacg tttcggcgag   3420
aagcaggcca ttatcgccgg catggcggcc gacgcgctgg gctacgtctt gctggcgttc   3480
gcgacgcgag gctggatggc cttccccatt atgattcttc tcgcttccgg cggcatcggg   3540
atgcccgcgt tgcaggccat gctgtccagg caggtagatg acgaccatca gggacagctt   3600
caaggatcgc tcgcggctct taccagccta acttcgatca ctggaccgct gatcgtcacg   3660
gcgatttatg ccgcctcggc gagcacatgg aacgggttgg catggattgt aggcgccgcc   3720
ctataccttg tctgcctccc cgcgttgcgt cgcggtgcat ggagccgggc cacctcgacc   3780
tgaatggaag ccggcggcac ctcgctaacg gattcaccac tccaagaatt ggagccaatc   3840
aattcttgcg gagaactgtg aatgcgcaaa ccaaccccttg gcagaacata tccatcgcgt   3900
ccgccatctc cagcagccgc acgcggcgca tctcgggcag cgttgggtcc tggccacggg   3960
tgcgcatgat cgtgctcctg tcgttgagga cccggctagg ctggcggggt tgccttactg   4020
gttagcagaa tgaatcaccg atacgcgagc gaacgtgaag cgactgctgc tgcaaaacgt   4080
ctgcgacctg agcaacaaca tgaatggtct tcggtttccg tgtttcgtaa agtctggaaa   4140
cgcggaagtc agcgccctgc accattatgt tccggatctg catcgcagga tgctgctggc   4200
taccctgtgg aacacctaca tctgtattaa cgaagcgctg gcattgaccc tgagtgattt   4260
ttctctggtc ccgccgcatc cataccgcca gttgtttacc ctcacaacgt tccagtaacc   4320
gggcatgttc atcatcagta acccgtatcg tgagcatcct ctctcgtttc atcggtatca   4380 ttaccccccat gaacagaaat ccccccttaca cggaggcatc agtgaccaaa caggaaaaaa   4440
ccgcccttaa catggcccgc tttatcagaa gccagacatt aacgcttctg gagaaactca   4500
acgagctgga cgcggatgaa caggcagaca tctgtgaatc gcttcacgac cacgctgatg   4560
agctttaccg cagctgcctc gcgcgtttcg gtgatgacgg tgaaaacctc tgacacatgc   4620
agctcccgga gacggtcaca gcttgtctgt aagcggatgc cgggagcaga caagcccgtc   4680
agggcgcgtc agcgggtgtt ggcgggtgtc ggggcgcagc catgacccag tcacgtagcg   4740
atagcggagt gtatactggc ttaactatgc ggcatcagag cagattgtac tgagagtgca   4800
ccatatgcgg tgtgaaatac cgcacagatg cgtaaggaga aaataccgca tcaggcgctc   4860
```

```
ttccgcttcc tcgctcactg actcgctgcg ctcggtcgtt cggctgcggc gagcggtatc    4920
agctcactca aaggcggtaa tacgttatc cacagaatca ggggataacg caggaaagaa     4980
catgtgagca aaaggccagc aaaaggccag gaaccgtaaa aaggccgcgt tgctggcgtt    5040
tttccatagg ctccgccccc ctgacgagca tcacaaaaat cgacgctcaa gtcagaggtg    5100
gcgaaacccg acaggactat aaagatacca ggcgtttccc cctggaagct ccctcgtgcg    5160
ctctcctgtt ccgaccctgc cgcttaccgg atacctgtcc gcctttctcc cttcgggaag    5220
cgtggcgctt tctcatagct cacgctgtag gtatctcagt tcggtgtagg tcgttcgctc    5280
caagctgggc tgtgtgcacg aaccccccgt tcagcccgac cgctgcgcct tatccggtaa    5340
ctatcgtctt gagtccaacc cggtaagaca cgacttatcg ccactggcag cagccactgg    5400
taacaggatt agcagagcga ggtatgtagg cggtgctaca gagttcttga agtggtggcc    5460
taactacggc tacactagaa ggacagtatt tggtatctgc gctctgctga agccagttac    5520
cttcggaaaa agagttggta gctcttgatc cggcaaacaa accaccgctg gtagcggtgg    5580
tttttttgtt tgcaagcagc agattacgcg cagaaaaaaa ggatctcaag aagatccttt    5640
gatcttttct acggggtctg acgctcagtg gaacgaaaac tcacgttaag ggattttggt    5700
catgagatta tcaaaaagga tcttcaccta gatcctttta aattaaaaat gaagttttaa    5760
atcaatctaa agtatatatg agtaaacttg gtctgacagt taccaatgct taatcagtga    5820
ggcacctatc tcagcgatct gtctatttcg ttcatccata gttgcctgac tccccgtcgt    5880
gtagataact acgatacggg agggcttacc atctggcccc agtgctgcaa tgataccgcg    5940
agacccacgc tcaccggctc cagatttatc agcaataaac cagccagccg aagggccga    6000 gcgcagaagt ggtcctgcaa ctttatccgc ctccatccag tctattaatt gttgccggga    6060
agctagagta agtagttcgc cagttaatag tttgcgcaac gttgttgcca ttgctgcagg    6120
catcgtggtg tcacgctcgt cgtttggtat ggcttcattc agctccggtt cccaacgatc    6180
aaggcgagtt acatgatccc ccatgttgtg caaaaaagcg gttagctcct tcggtcctcc    6240
gatcgttgtc agaagtaagt tggccgcagt gttatcactc atggttatgg cagcactgca    6300
taattctctt actgtcatgc catccgtaag atgcttttct gtgactggtg agtactcaac    6360
caagtcattc tgagaatagt gtatgcggcg accgagttgc tcttgcccgg cgtcaacacg    6420
ggataatacc gcgccacata gcagaacttt aaaagtgctc atcattggaa acgttcttc     6480 ggggcgaaaa ctctcaagga tcttaccgct gttgagatcc agttcgatgt aacccactcg    6540
tgcacccaac tgatcttcag catcttttac tttcaccagc gtttctgggt gagcaaaaac    6600
aggaaggcaa aatgccgcaa aaaagggaat aagggcgaca cggaaatgtt gaatactcat    6660
actcttcctt tttcaatatt attgaagcat ttatcagggt tattgtctca tgagcggata    6720
catatttgaa tgtatttaga aaaataaaca ataggggtt ccgcgcacat ttccccgaaa     6780
agtgccacct gacgtctaag aaaccattat tatcatgaca ttaacctata aaaataggcg    6840
tatcacgagg ccctttcgtc ttcaagaatt agcttgtcat ctgccggatg aggcaaaacc    6900
ctgcctacgg cgcgattaca tcgtcccagc gcgatcgctc ttactgttga tggctcgtgc    6960
ttaaaaacaa tgcaaacttc accgtttcag ctggtgattt tcgactgtga tggtgtgctt    7020
gttgatagcg gaacgcatca ctaatcgcgt ctttgcagac atgctcaatg aactgggtct    7080
gttggtgact ttggatgaca tgtttgagca gtttgtgggt cattccatgg ctgactgtct    7140
caaactaatt gagcgacggt taggcaatcc tccaccccct gactttgttc agcactatca    7200
acgccgtacc cgtatcgcgt tagaaacgca tctacaagcc gttcctgggg ttgaagaggc    7260
```

```
tttggatgct cttgaattgc cctactgtgt tgcgtccagt ggtgatcatc aaaagatgcg      7320
aaccacactg agcctgacga agctctggcc acgatttgag ggacgaatct tcagcgtgac      7380
tgaagtacct cgcggcaagc catttcccga tgtcttttg ttggccgccg atcgcttcgg       7440
ggttaatcct acggcctgcg ctgtgatcga agacaccccc ttgggagtag cggcaggcgt      7500
ggcggcagga atgcaagtgt ttggctacgc gggttccatg cccgcttggc gtctgcaaga      7560
agccggtgcc catctcattt tgacgatat gcgactgctg cccagtctgc tccaatcgtc       7620
gccaaaagat aactccacag cattgcccaa tccctaaccc ctgctcgcgc cgcaactaca      7680
cactaaaccg ttcctgcgcg atcgctctta ctgttgatgg ctcgtgctta aaaacaatgc      7740
aaccctaacc gtttcagctg gtgattttcg gacgatttgg cttacaggga taactgagag      7800
tcaacagcct ctgtccgtca ttgcacaccc atccatgcac tggggacttg actcatgctg      7860
aatcacattt cccttgtcca ttgggcgaga ggggagggga atcttctgga ctcttcacta      7920
agcggcgatc gcaggttctt ctacccaagc agtggcgatc gcttgattgc agtcttcaat      7980
gctggcctct gcagccatcg ccgccaccaa agcatcgtag gcgggacgtt gttgctccag      8040
taaagtcttc gcccgtaaca atccccagcg actgcgtaaa tccgcttcgg caggattgcg      8100
atcgagttgc cgccacagtt gtttccactg ggcgcgatcg tcagctcccc cttccacgtt      8160
gccgtagacc agttgctctg ccgctgcacc ggccatcaac acctgacacc actgttccag      8220
cgatcgctga ctgagttgcc cctgtgcggc ttcggcttct agcgcagctg cttggaactg      8280 cacaccccg cgaccaggtt gtccttggcg cagcgcttcc cacgctgaga gggtgtagcc       8340
cgtcacgggt aaccgatatc gaattcatga                                        8370

<210> SEQ ID NO 36
<211> LENGTH: 5954
<212> TYPE: DNA
<213> ORGANISM: Artificial sequence
<220> FEATURE:
<223> OTHER INFORMATION: pNS3 construct

<400> SEQUENCE: 36
cggagtgtat actggcttac tatgttggca ctgatgaggg tgtcagtgaa gtgcttcatg        60
tggcaggaga aaaaaggctg caccggtgcg tcagcagaat atgtgataca ggatatattc       120
cgcttcctcg ctcactgact cgctacgctc ggtcgttcga ctgcggcgag cggaaatggc       180
ttacgaacgg ggcggagatt tcctggaaga tgccaggaag atacttaaca gggaagtgag       240
agggccgcgg caaagccgtt tttccatagg ctccgccccc ctgacaagca tcacgaaatc       300
tgacgctcaa atcagtggtg gcgaaacccg acaggactat aaagatacca ggcgtttccc       360
cctggcggct ccctcgtgcg ctctcctgtt cctgcctttc ggtttaccgg tgtcattccg       420
ctgttatggc cgcgtttgtc tcattccacg cctgacactc agttccgggt aggcagttcg       480
ctccaagctg gactgtatgc acgaaccccc cgttcagtcc gaccgctgcg ccttatccgg       540
taactatcgt cttgagtcca acccggaaag acatgcaaaa gcaccactgg cagcagccac       600
tggtaattga tttagaggag ttagtcttga agtcatgcgc cggttaaggc taaactgaaa       660
ggacaagttt tggtgactgc gctcctccaa gccagttacc tcggttcaaa gagttggtag       720
ctcagagaac cttcgaaaaa ccgccctgca aggcggtttt ttcgttttca gagcaagaga       780
ttacgcgcag accaaaacga tctcaagaag atcatcttat taatcagata aaatatttct       840
tttctacggg gtctgacgct cagtctagtt cagccagctc gtcgtgatgt cgaaacccaa       900
```

```
gccaccctca gaggtgaagg ccgcttcgag cacatcggga agcgtgtcga cgacggtgct    960
cggtgcctcg ggtaagagcc agatagatgc ggtgacgttc accgtcgcga tcgtggcggg   1020
aaccacggtc actgcgtccg ttacaactcg cacgtcgtcg gccagcacga ctgactcgac   1080
ggcttcgatt agcccgggag aggcaaggcc atcaggctcg gtagacagaa tgctgattaa   1140
cacctcgccg ggagcagggc tgctcacagc cgcgtccttc acccgtgggt cagccgtcag   1200
cgcttgatag cggtaccagg ccgcaccgcc tgcggtcgag ctgcccttga tccgctcgat   1260
ggtgcgatcg cgaagctcgc catccggctc attcggctgc cgcaccacgc cgtagaacgc   1320
ggcaaggttg tcgaggtcgg ggccgtttga gtagcgaagc agtgtcgcaa gaagtgcgtc   1380
gttgatccgc tgacgcagga tcagctcgcg ggctgcgcag acctccagca gcttgatgac   1440
cgggtcggat tcgaggatgg cggtgtagct ggcgtcacgc gatcgcaggt cgtcgatcaa   1500
gtcctgcagg atcagttcaa agtccagcgc ttcgatgatg gtgggcgcgg aatcgtagc    1560
aaagtcaaga acggtcatga gacgactaag ccctccagcg tgatacgcct gccctcgggg   1620
atgtagtagc cgatcaggtt cagctcgact tgaccagctg cgctggctga gacgatgcga   1680
accttctcca gcttcagccg tggctcccag cgatcgagcg cttcagctgt ggccgccacc   1740
aggtcaacga tgagggactg gttgatcggt ctagtcatca aataaaacga aaggctcagt   1800
cgaaagactg ggcctttcgt tttatctgtt gtttgtcggt gaacgctctc ctgagtagga   1860
caaatccgcc gggagcggat ttgaacgttg cgaagcaacg gcccgagggg tggcgggcag   1920
gacgcccgcc ataaactgcc aggcatcaaa ttaagcagaa ggccatcctg acggatggcc   1980
tttttgcgtt tctactctag ttttcgaaa ccccaggctt gacactttat gcttccggct    2040
cgtataatgt gtggaattgt gagcggataa caatttcaca caaggaggaa aaacatatgt   2100
ccagagaccg aaagtgaaac gtgatttcat gcgtcatttt gaacattttg taaatcttat   2160
ttaataatgt gtgcggcaat tcacatttaa tttatgaatg ttttcttaac atcgcggcaa   2220
ctcaagaaac ggcaggttcg gatcttagct actagagaaa gaggagaaat actagatgcg   2280
taaaggcgaa gagctgttca ctggtgtcgt ccctattctg gtggaactgg atggtgatgt   2340
caacggtcat aagttttccg tgcgtggcga gggtgaaggt gacgcaacta atggtaaact   2400
gacgctgaag ttcatctgta ctactggtaa actgccggta ccttggccga ctctggtaac   2460
gacgctgact tatggtgttc agtgctttgc tcgttatccg gaccatatga agcagcatga   2520
cttcttcaag tccgccatgc cggaaggcta tgtgcaggaa cgcacgattt cctttaagga   2580
tgacggcacg tacaaaacgc gtgcggaagt gaaatttgaa ggcgataccc tggtaaaccg   2640
cattgagctg aaaggcattg actttaaaga agacggcaat atcctgggcc ataagctgga   2700
atacaatttt aacagccaca atgtttacat caccgccgat aaacaaaaaa atggcattaa   2760
agcgaatttt aaaattcgcc acaacgtgga ggatggcagc gtgcagctgg ctgatcacta   2820
ccagcaaaac actccaatcg gtgatggtcc tgttctgctg ccagacaatc actatctgag   2880
cacgcaaagc gttctgtcta agatccgaa cgagaaacgc gatcatatgg ttctgctgga   2940
gttcgtaacc gcagcgggca tcacgcatgg tatggatgaa ctgtacaaat gaggtctcta   3000
gcggatcggc acgtaagagg ttccaacttt caccataatg aaataagatc actaccgggc   3060
gtattttttg agttatcgag attttcagga gctaaggaag ctaaaatgga gaaaaaaatc   3120
actggatata ccaccgttga tatatcccaa tggcatcgta agaacatttt gaggcatttt   3180
cagtcagttg ctcaatgtac ctataaccag accgttcagc tggatattac ggcctttta    3240
aagaccgtaa agaaaaataa gcacaagttt tatccggcct ttattcacat tcttgcccgc   3300
```

```
ctgatgaatg ctcatccgga gttccgtatg gcaatgaaag acggtgagct ggtgatatgg    3360
gatagtgttc acccttgtta caccgttttc catgagcaaa ctgaaacgtt ttcatcgctc    3420
tggagtgaat accacgacga tttccggcag tttctacaca tatattcgca agatgtggcg    3480
tgttacggtg aaaacctggc ctatttccct aaagggttta ttgagaatat gtttttcgtc    3540
tcagccaatc cctgggtgag tttcaccagt tttgatttaa acgtggccaa tatggacaac    3600
ttcttcgccc ccgttttcac tatgggcaaa tattatacgc aaggcgacaa ggtgctgatg    3660
ccgctggcga ttcaggttca tcatgccgtc tgtgatggct ccatgtcgg cagaatgctt     3720 aatgaattac aacagtactg cgatgagtgg cagggcgggg cgtaattttt ttaaggcagt    3780
tattggtgcc cttgaattcc tactagtcga agcggcatgc atttacgttg acaccatcga    3840
atggtgcaaa accttcgcg gtatggcatg atagcgcccg gaagagagtc aattcagggt      3900
ggtgaatgtg aaaccagtaa cgttatacga tgtcgcagag tatgccggtg tctcttatca    3960
gaccgtttcc cgcgtggtga accaggccag ccacgtttct gcgaaaacgc gggaaaaagt    4020
ggaagcggcg atggcggagc tgaattacat tcccaaccgc gtggcacaac aactggcggg    4080
caaacagtcg ttgctgattg gcgttgccac ctccagtctg gccctgcacg cgccgtcgca    4140
aattgtcgcg gcgattaaat ctcgcgccga tcaactgggt gccagcgtgg tggtgtcgat    4200
ggtagaacga agcggcgtcg aagcctgtaa agcggcggtg cacaatcttc tcgcgcaacg    4260
cgtcagtggg ctgatcatta actatccgct ggatgaccag gatgccattg ctgtggaagc    4320
tgcctgcact aatgttccgg cgttatttct tgatgtctct gaccagacac ccatcaacag    4380
tattattttc tcccatgaag acggtacgcg actgggcgtg gagcatctgg tcgcattggg    4440
tcaccagcaa atcgcgctgt tagcgggccc attaagttct gtctcggcgc gtctgcgtct    4500
ggctggctgg cataaatatc tcactcgcaa tcaaattcag ccgatagcgg aacgggaagg    4560
cgactggagt gccatgtccg ttttcaaca aaccatgcaa atgctgaatg agggcatcgt    4620
tcccactgcg atgctggttg ccaacgatca gatggcgctg gcgcaatgc gcgccattac    4680 cgagtccggg ctgcgcgttg gtgcggatat ctcggtagtg ggatacgacg ataccgaaga    4740
cagctcatgt tatatcccgc cgttaaccac catcaaacag gattttcgcc tgctggggca    4800
aaccagcgtg gaccgcttgc tgcaactctc tcagggccag gcggtgaagg gcaatcagct    4860
gttgcccgtc tcactggtga aaagaaaaac caccctggcg cccaatacgc aaaccgcctc    4920
tccccgcgcg ttggccgatt cattaatgca gctggcacga caggtttccc gactggaaag    4980
cgggcagtga tcccacagcc gccagttccg ctggcggcat tttaactttc tttaatgaat    5040
ctagtgacaa gccggggcag acgtgagccg tagtcccgtc gccagacgcg ggtgcccacg    5100
ggcgtcgtca ggatgtccgt aattgactgc cggaggtggt caatgccctt cagctccttg    5160
ccactgtcac ggctcatgcc tcgggtcatt agtcgcccgc tccggtatct tcactggctt    5220
cgatgattgc cgccccgcag ctgcagaggt caccgatccg agcagtcggc ctctggttgg    5280
taaagaccgt gcgactgccg gtgatgatcg tgttcaagcc atgcaggggg caggcgtgaa    5340
ggtcatcctt tcgggccacg gggcggctgt tgacgaaggt gtcgtcgctc ccggtgatga    5400
tgatcccgcc gtgatcggtc acgtcgttta gtcgagcgat gcctggcgtc gtagtcacgg    5460
gtttaggtca atacgacttg cggtcactgt aacgttgccc tcggcggtca cgttaacgtc    5520
gccttgggct tcgacttgcg cctcctgcac aaggatcaca atccgtcctt gggctgcggt    5580
gaggtcgatc ttgtactcat gcgcttcgcg gtcgtactgg atgattgagt catcctcgaa    5640
```

-continued

```
ctgcgtcttt tggatcgttt ctttgtcctc gatctggggg tagtcagtcg agaacgcgcc    5700
gggcatcgcg aagccctgac tgatctcgcc ggaggggggcc atcacgacga cggcctcacc    5760
gacctcgggc gcccaccaga accgatcctt gcccgctcgc tgcgtgagcc acggaatcca    5820
gtcagtgagg agcagcgcct cgccgctctc ctcgtcttcc tcgatcgcga cacggatcag    5880 cccttggga tagtcagcct cggctaccct gcctacgcgg agcaagttgc cgtgacgccg    5940
actgtctcga gtat                                                      5954
```